(12) United States Patent
Potter et al.

(10) Patent No.: US 8,124,614 B2
(45) Date of Patent: *Feb. 28, 2012

(54) STEROIDAL COMPOUNDS FOR INHIBITING STEROID SULPHATASE

(75) Inventors: Barry Victor Lloyd Potter, Slough (GB); Michael John Reed, Slough (GB); Lok Wai Lawrence Woo, Slough (GB)

(73) Assignee: Sterix Limited, Berkshire (GB)

( * ) Notice: Subject to any disclaimer, the term of this patent is extended or adjusted under 35 U.S.C. 154(b) by 858 days.

This patent is subject to a terminal disclaimer.

(21) Appl. No.: 11/855,603

(22) Filed: Sep. 14, 2007

(65) Prior Publication Data

US 2008/0312266 A1 Dec. 18, 2008

Related U.S. Application Data

(60) Division of application No. 11/329,982, filed on Jan. 11, 2006, now Pat. No. 7,276,513, which is a division of application No. 10/825,758, filed on Apr. 16, 2004, now Pat. No. 7,098,218, which is a continuation-in-part of application No. PCT/GB02/04686, filed on Oct. 17, 2002.

(30) Foreign Application Priority Data

Oct. 18, 2001 (GB) .................................. 0125073.7
Oct. 18, 2001 (WO) ...................... PCT/GB01/04645
Apr. 23, 2002 (GB) .................................. 0209274.0

(51) Int. Cl.
*A61K 31/473* (2006.01)
*C07D 221/18* (2006.01)
(52) U.S. Cl. ........................... 514/284; 546/77; 435/184
(58) Field of Classification Search .................. 514/284; 546/77; 435/184
See application file for complete search history.

(56) References Cited

U.S. PATENT DOCUMENTS

| 3,972,884 A | 8/1976 | Chamberlin |
| 4,039,547 A | 8/1977 | Jones |
| 7,098,218 B2 * | 8/2006 | Potter et al. .................... 514/284 |
| 7,276,513 B2 * | 10/2007 | Potter et al. .................... 514/284 |

FOREIGN PATENT DOCUMENTS

| EP | 0 478 910 A2 | 4/1992 |
| FR | 2 109 619 | 5/1972 |
| GB | 1350397 | 4/1974 |
| GB | 2 003 479 A | 3/1979 |
| WO | WO 93/05064 | 3/1993 |
| WO | WO 02/32409 A2 | 4/2002 |

OTHER PUBLICATIONS

Gupta et al., Indian J. of Chem. Soc. B, vol. 38B, (5) p. 563-571, 1999.

* cited by examiner

*Primary Examiner* — Charanjit Aulakh
(74) *Attorney, Agent, or Firm* — Frommer Lawrence & Haug LLP; Sandra Kuzmich; Russell A. German

(57) ABSTRACT

There is provided a compound having Formula (I) wherein G is H or a substituent, and wherein $R^1$ is any one of a sulphamate group, a phosphonate group, a thiophosphonate group, a sulphonate group or a sulphonamide group, capable of inhibiting steroid sulphatase.

34 Claims, 3 Drawing Sheets

STEROIDAL COMPOUNDS FOR INHIBITING STEROID SULPHATASE

REFERENCE TO RELATED APPLICATIONS

This application is a divisional of U.S. patent application Ser. No. 11/329,982, filed Jan. 11, 2006, now U.S. Pat. No. 7,276,513, issued Oct. 2, 2007, which is a divisional of U.S. patent application Ser. No. 10/825,758, filed Apr. 16, 2004, now U.S. Pat. No. 7,098,218 issued Aug. 29, 2006, which is continuation-in-part of International Application PCT/GB02/04686 filed Oct. 17, 2002 and published as WO 03/033518 on Apr. 24, 2003, which claims priority from Great Britain Patent Application 0209274.0 filed Apr. 23, 2002, which claims priority from Great Britain Patent Application 0125073.7 and International Patent Application PCT/GB01/04645, both of which were filed on Oct. 18, 2001. International Patent Application PCT/GB01/04645 was published as WO 02/32409 on Apr. 25, 2002. Each of the above applications, and each document cited in this text and in each of the above applications ("application cited documents") and each document cited or referenced in each of the application cited documents, and any manufacturer's specifications or instructions for any products mentioned in this text and in any document incorporated into this text, are hereby incorporated herein by reference; and, technology in each of the documents incorporated herein by reference can be used in the practice of this invention.

It is noted that in this disclosure, terms such as "comprises", "comprised", "comprising", "contains", "containing" and the like can have the meaning attributed to them in U.S. patent law; e.g., they can mean "includes", "included", "including" and the like. Terms such as "consisting essentially of" and "consists essentially of" have the meaning attributed to them in U.S. patent law, e.g., they allow for the inclusion of additional ingredients or steps that do not detract from the novel or basic characteristics of the invention, i.e., they exclude additional unrecited ingredients or steps that detract from novel or basic characteristics of the invention, and they exclude ingredients or steps of the prior art, such as documents in the art that are cited herein or are incorporated by reference herein, especially as it is a goal of this document to define embodiments that are patentable, e.g., novel, non-obvious, inventive, over the prior art, e.g., over documents cited herein or incorporated by reference herein. And, the terms "consists of" and "consisting of" have the meaning ascribed to them in U.S. patent law; namely, that these terms are closed ended.

FIELD OF INVENTION

The present invention relates to a compound. In particular the present invention provides compounds capable of inhibiting steroid sulphatase.

BACKGROUND TO THE INVENTION

Breast cancer is a devastating disease which remains to be a major cause of death for women in most Western countries. It is estimated to affect approximately 1 million women per year across the globe.[1]

Britain has one of the highest mortality rate for breast cancer in the world with over 35,000 women diagnosed each year accounting for nearly one in five of all cancer cases. It is estimated that 1 in 10 women living to the age of 85 in Britain will develop breast cancer during the course of her life. Although modern methods of treatment as well as an earlier detection of the disease have greatly improved survival rates, breast cancer remains the leading cause of death for women aged between 35-54.[2]

All women are at risk of breast cancer although a number of risk factors have been identified, most of them being related to women's hormonal and reproductive history as well as their family background of the disease. Women at higher risk are generally those with a strong family history of the disease, early onset of menarche, late onset of menopause or a first full-term pregnancy after the age of 30.[2]

In the earliest stages of a breast cancer, surgery appears to be the treatment of choice. In most of the cases, breast conserving surgical techniques, such as local incision of lump(s) in the breast(s), are involved rather than mastectomy. To prevent any recurrence of the disease, radiotherapy is often prescribed, particularly if breast conserving techniques have been involved.[3] It is also used to reduce large tumours to an operable size so that conservational surgery can be carried out.[4]

For advanced breast cancers, when the tumour has spread or recurred, the aim in the treatment is no longer to cure but to reach a palliative control. This is the case when metastases of the tumour have reached locations such as bones, skin, lymph, node or brain. The treatment varies depending on the hormonal status of the patient (whether it is a pre- or post-menopausal woman to be treated) and depending on the type of tumour. Certain tumours have indeed been proven to rely on estrogens for their growth and development, leading to what is called a Hormone Dependent Breast Cancer (HDBC, see I-1). While non HDBC are treated with chemotherapy, where the aim is to kill differentially tumour cells using a combination of cytotoxic agents,[5] HDBC are expected to respond to endocrine therapy.

The concept of hormone dependent tumours appeared in the early 1960s, when the model of estrogens action was first introduced.[6] In order for estrogens to regulate cell growth and function in humans, a specific protein, called the human Oestrogen Receptor (hER), must be present.[7] This protein, localised in the nucleus, interacts with estrogens resulting in the formation of a binding complex. This acts as a transcription factor by activating production of m-RNA from specific genes, one or more of which are probably essential for efficient tumour cell growth.

Patients with a measurable level of receptor protein are classified as oestrogen-receptor-positive (ER+) with opposition to oestrogen-receptor-negative (ER−). About 50% of pre-menopausal women and 75% of post-menopausal women fall into the ER+ group[8] where the development of breast cancers can be directly linked to the presence of estrogens. Endocrine therapy, where the use of drugs results in a deprivation of estrogenic stimulation to cells, has proven to be an effective approach to the treatment of HDBC. Originally, two classes of drugs, responding to different strategies, were developed: anti-oestrogens and aromatase inhibitors.

Anti-oestrogens, as antagonists of the oestrogen receptor, have been one of the first treatment considered for HDBC. Their action rely on their ability to bind competitively to the specific receptor protein hER, thus preventing access of endogenous estrogens to their specific binding site. Consequently, the natural hormone is unable to maintain tumour growth.

Of the anti-oestrogens commonly used in breast cancer therapy, tamoxifen (below) is the most widely used because of the very low toxicity profile of the molecule. Despite its non-steroidal skeleton, tamoxifen possesses a mixed agonist-antagonist activity that limits its therapeutic potential.[9] In addition, some form of drug resistance has been reported in patients after long-term tamoxifen treatment.[10]

Novel pure anti-oestrogenic drugs, such as ICI 164384 (below), have since been discovered but the loss of potency compared with that of tamoxifen suggested the need to design more highly potent targets.[11]

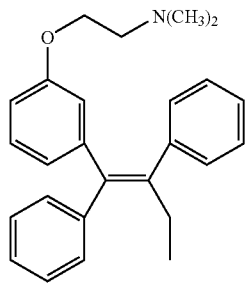

Tamoxifen

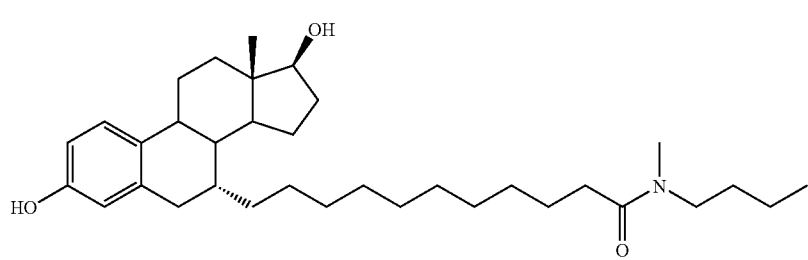

ICI 164384

For some years now, a new type of anti-oestrogen has emerged, combining oestrogen agonism on target tissues such as bone or liver and antagonism and/or minimal agonism in reproductive tissues such as breasts or uterus.[12] These compounds, designed as Selective Oestrogen Receptor Modulators (SERMs), are not only potentially effective in reducing a patient's risk of breast carcinoma but they have also been shown to increase bone mineral density and prevent osteoporosis in post-menopausal women. Raloxifen is the first of this class of compounds to be used clinically.[13] More SERMs are currently in clinical trials and these molecules might one day replace tamoxifen as the first line treatment for women with HDBC.

The use of therapeutic agents that inhibit one or several enzyme of the steroid biosynthesis pathway represents another important strategy to control of the development of oestrogen-dependent tumours.[14] The enzyme aromatase, which converts androgenic C19 steroids to estrogenic C18 steroids, has been the prime target for reducing oestrogen levels. This enzyme complex, which contains a cytochrome P450 haemoprotein, catalyses the aromatisation of the androgen A-ring with the subsequent loss of the C19 methyl group to yield estrogens.

Aminoglutethimide (below) was the first aromatase inhibitor used for the treatment of breast cancer. It however showed a number of undesirable side effects given its wide spectrum of inhibitory effects on other P450-dependant enzymes, and attempts to improve on the original structure have led to a number of non-steroidal compounds entering clinical trials.[15] The last generation developed compounds such as letrozole, which combine high potency and high selectivity for the enzyme, and are also better tolerated.

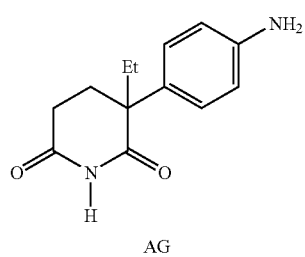

AG

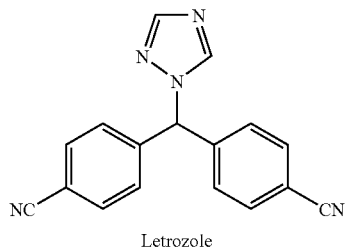

Letrozole

Structure of different types of aromatase inhibitors. Generation I: aminoglutethimide, AG; generation III, letrozole.

Traditionally, aromatase inhibitors are reserved as second line treatment for advanced HDBC patients whose diseases are no longer controlled by tamoxifen. However, because of the extreme good toxicity profile of some of the latest aromatase inhibitors, recent clinical trials have been conducted to assess their suitability as first line treatment for HDBC.

Strong evidence has emerged over the past decade, both biochemically and clinically, that the sole inhibition of the enzyme aromatase cannot afford an effective reduction of estrogenic stimulation to HDBC, the reason being that other pathways are involved in oestrogen biosynthesis. The sulphatase pathway is now considered to be the major route for breast tumour oestrogen synthesis since sulphatase activity was found to provide 10 fold more oestrone than the aromatase activity.[16]

In the sulphatase pathway, estrogens are synthesised from the highly available precursor oestrone-sulphate, via two enzymes (scheme below): oestrone sulphatase (STS) which hydrolyses oestrone-sulphate into oestrone, and 17β-hydroxysteroid dehydrogenase (17β-HSD) which reduces oestrone into oestradiol. These two enzymes represent the latest targets for oestrogen deprivation strategies.

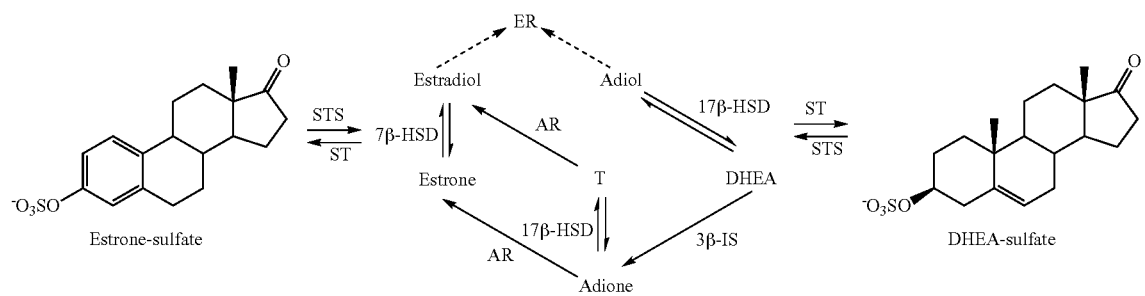

Origin of estrogens in normal and tumoral breast cells. AR, aromatase; ST: steroid sulfotransferase; STS, steroid sulphatase; 17β-HSD, 17β-hydroxysteroid dehydrogenase; 3β-IS, 3β-hydroxysteroid dehydrogenase $\Delta^5,\Delta^4$-isomerase; ER, oestrogen receptor.

Several potent inhibitors have been identified for oestrone sulphatase. They all share the common structural feature of an aromatic ring bearing a substituent that mimics the phenolic A-ring of the enzyme substrate, oestrone-sulphate. On the development of steroidal inhibitors, a wide variety of chemical groups have been introduced at C3, of which the 3-O-sulfamate was found to be the most potent for the oestrone molecule. The resulting compound, estrone-3-O-sulfamate (below) led to the identification of the aryl-O-sulphamate structure as an active pharmacophore required for potent inhibition of STS. EMATE was shown to inhibit steroid sulphatase activity in a time- and concentration-dependent manner[17] and was active in vivo on oral administration.[18] It was however revealed to be highly estrogenic which raised the need to design STS inhibitors devoid of agonist activity on hER.

To avoid the problems linked to an active steroid nucleus, non steroid-based inhibitors have been synthesised. Coumarin sulphamate such as 4-methylcoumarin-7-O-sulfamate (COUMATE, below), where the active pharmacophore is conserved, have been among the first inhibitors of that type to be identified.[19] Although COUMATE is less potent than EMATE, it has the advantage of being non estrogenic.[20] Some tricyclic coumarin-based sulphamates have also been developed and turned out to be much more potent than COUMATE, while retaining its non estrogenic characteristic.[21] 667COUMATE, which is some 3 times more potent than EMATE in vitro is now in pre-clinical development for clinical trials.[22]

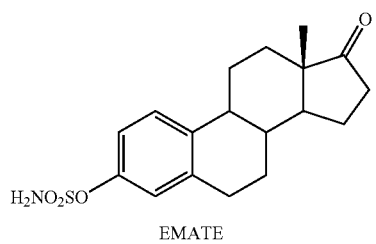

EMATE

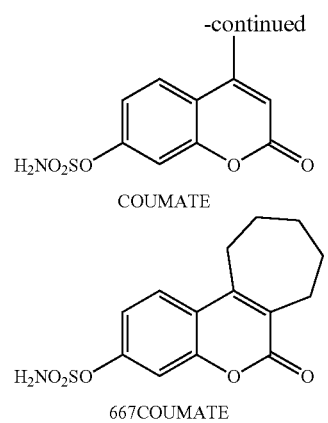

COUMATE

667COUMATE

Structures of the steroid sulphatase inhibitors EMATE, COUMATE and 667COUMATE.

PCT/GB92/01587 teaches novel steroid sulphatase inhibitors and pharmaceutical compositions containing them for use in the treatment of oestrone dependent tumours, especially breast cancer. These steroid sulphatase inhibitors are sulphamate esters, such as N,N-dimethyl oestrone-3-sulphamate and, preferably, oestrone-3-sulphamate (EMATE). It is known that EMATE is a potent E1-STS inhibitor as it displays more than 99% inhibition of E1-STS activity in intact MCF-7 cells at 0.1 mM. EMATE also inhibits the E1-STS enzyme in a time- and concentration-dependent manner, indicating that it acts as an active site-directed inactivator. Although EMATE was originally designed for the inhibition of E1-STS, it also inhibits dehydroepiandrosterone sulphatase (DHA-STS), which is an enzyme that is believed to have a pivotal role in regulating the biosynthesis of the oestrogenic steroid androstenediol. Also, there is now evidence to suggest that androstenediol may be of even greater importance as a promoter of breast tumour growth. EMATE is also active in vivo as almost complete inhibition of rat liver E1-STS (99%) and DHA-STS (99%) activities resulted when it is administered either orally or subcutaneously. In addition, EMATE has been shown to have a memory enhancing effect in rats. Studies in mice have suggested an association between DHA-STS activity and the regulation of part of the immune response. It is thought that this may also occur in humans. The bridging O-atom of the sulphamate moiety in EMATE is important for inhibitory activity. Thus, when the 3-O-atom is replaced by other heteroatoms as in oestrone-3-N-sulphamate and oestrone-3-S-sulphamate, these analogues are weaker non-time-dependent inactivators.

Although optimal potency for inhibition of E1-STS may have been attained in EMATE, it is possible that oestrone may be released during sulphatase inhibition and that EMATE and its oestradiol congener may possess oestrogenic activity. 17β-HSD, which catalyses the final step in estrogens and androgens biosynthesis, also appeared as a target for oestrogen deprivation strategies. This enzyme is responsible for the interconversion of the oxidised form (less active) and the reduced form (more active) of steroids. Its activity directly supports the growth and development of oestrogen dependent tumours since it preferably reduces oestrone into estradiol[25] and in a minor extend, via the conversion of the androgen DHEA into androstenediol (Adiol), which has recently been proven to have estrogenic properties and to be able to bind to the oestrogen receptor.[26]

17β-HSD belongs to a family of isoenzymes, 11 of which have been so far identified and cloned.[27] Each type has a selective substrate affinity and directional activity which means that selectivity of drug action has to be achieved. 17β-HSD type 1 is the isotype that catalyses the interconversion of oestrone and oestradiol.

Unlike STS inhibitors, only few 17β-HSD inhibitors have been reported. Most of the steroidal inhibitors for 17β-HSD type 1 have in common a D-ring modified structure. Oestradiol derivatives which contain a side-chain with a good leaving group at the 16α-position have been shown to be a potent class of inhibitors. In particular, 16α-(bromoalkyl)-estradiol[28] where the side-chains exhibit high reactivity towards nucleophilic amino-acids residues in the active site of the enzyme were found to be promising irreversible inhibitors. Analogues containing short bromoalkyl moieties at position 16 exhibited the highest activity with 16α-(Bromopropyl)-oestradiol, followed by 16α-(Bromobutyl)-oestradiol, the most potent of the series (3 and 4). They, however, turned out to be pure agonists of the oestrogen receptor.

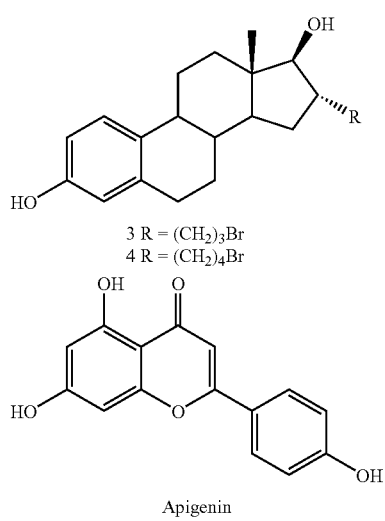

3 R = (CH$_2$)$_3$Br
4 R = (CH$_2$)$_4$Br

Apigenin

17β-HSD type 1 inhibitors: 16α-(bromopropyl)-oestradiol, 3;
16α-(bromopropyl)-oestradiol, 4 and a flavone derivative, apigenin.

In an attempt to eliminate the intrinsic oestrogenicity of potent inhibitors and possibly at the same time engineer anti-oestrogenic properties into the molecule, several 16α-(broadly)-oestradiol derivatives bearing the C7α-alkylamide side chain of the known anti-oestrogen ICI 164384 were synthesised.[29] However, rather poor inhibition of 17β-HSD type 1 was obtained, with estrogenic and anti-oestrogenic properties not completely abolished or introduced respectively.

In parallel, non-steroidal inhibitors of 17β-HSD type 1 have been designed. Flavonoids, which are structurally similar to estrogens, are able to bind to the oestrogen receptor with estrogenic or anti-estrogenic activities.[30] Their action on aromatase activity is well documented and in recent studies, they were found to reduce the conversion of oestrone into oestradiol catalysed by 17β-HSD type 1.[31] Flavone derivatives, such as apigenin (FIG. 6) emerged from a SAR study as a promising compounds with some inhibitory activity on 17β-HSD type 1 without being estrogenic at the inhibitory concentration.[32]

Ahmed et al (Biochem Biophys Res Commun 1999 Jan. 27; 254(3):811-5) report on a structure-activity relationship study of steroidal and nonsteroidal inhibitors of STS.

Steroid dehydrogenases (DH) such as oestradiol 17β-hydroxysteroid dehydrogenases (E2HSD) have pivotal roles in regulating the availability of ligands to interact with the oestrogen receptor. E2HSD Type I reduces oestrone (E1) to the biologically active oestrogen, oestradiol (E2), while E2HSD Type II inactivates E2 by catalysing its oxidation to E1. Thus the identification of compounds having DH inhibitory activity, in particular, inhibitors of E2HSD Type I, could be of therapeutic value in inhibiting the formation of E2.

SUMMARY ASPECTS OF THE PRESENT INVENTION

The present invention provides novel compounds which are capable of acting as effective steroid sulphatase inhibitors. The present invention identifies that the compounds of the present application are effective steroid sulphatase inhibitors.

FIG. 1 shows some of the enzymes involved in the in situ synthesis of oestrone from oestrone sulphate, and oestradiol. "STS" denotes Oestrone Sulphatase, "E2DH Type I" denotes Oestradiol 17β-hydroxysteroid dehydrogenase Type I or Oestradiol 17β-hydroxysteroid dehydrogenase Type 1, 3, 5 and/or 7 and "E2DH Type II" denotes Oestradiol 17β-hydroxysteroid dehydrogenase Type II or Oestradiol 17β-hydroxysteroid dehydrogenase Type 2 and/or 8.

As can be seen, two enzymes that are involved in the peripheral synthesis of oestrogens are the enzyme Oestradiol 17β-hydroxysteroid dehydrogenase and the enzyme oestrone sulphatase.

In situ synthesis of oestrogen is thought to make an important contribution to the high levels of oestrogens in tumours and therefore specific inhibitors of oestrogen biosynthesis are of potential value for the treatment of endocrine-dependent tumours.

Moreover, even though oestrogen formation in malignant breast and endometrial tissues via the sulphatase pathway makes a major contribution to the high concentration of oestrogens, there are still other enzymatic pathways that contribute to in vivo synthesis of oestrogen.

Thus, there is an urgent need to develop new therapies for the treatment of these cancers.

The present invention therefore seeks to overcome one or more of the problems associated with the prior art methods of treating breast and endometrial cancers.

In one aspect, therefore, the present invention provides a use of a compound for the preparation of a medicament that can affect, such as substantially inhibit, the oestrone sulphatase pathway—which pathway converts oestrone to and from oestradiol—and/or affect, such as substantially inhibit, the steroid dehydrogenase pathway—which pathway converts oestrone to and from oestradiol.

This aspect of the present invention is advantageous because by the administration of one type of compound it is possible to block the synthesis of oestradiol from oestrone or E1S. Hence, the present invention provides compounds that have considerable therapeutic advantages, particularly for treating breast and endometrial cancers.

The compounds of the present invention may comprise other substituents. These other substituents may, for example, further increase the activity of the compounds of the present invention and/or increase stability (ex vivo and/or in vivo).

BRIEF DESCRIPTION OF THE DRAWINGS

The following Detailed Description, given by way of example, but not intended to limit the invention to specific embodiments described, may be understood in conjunction with the accompanying Figures, incorporated herein by reference, in which.

DETAILED ASPECTS OF THE PRESENT INVENTION

Figure 1:
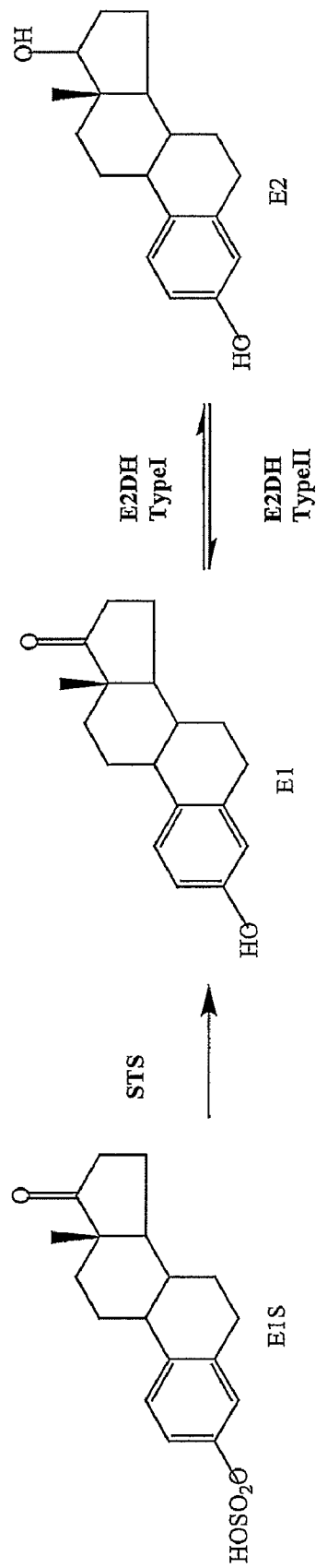
FIG. 1 shows some of the enzymes involved in in situ synthesis of oestrone from oestrone sulphate, and oestradiol. "STS" denotes Steroid Sulphatase, "E2DH Type I" denotes oestradiol 17β-hydroxysteroid dehydrogenase Type I or oestradiol 17β-hydroxysteroid dehydrogenase Type 1, 3, 5 and/or 7 and "E2DH Type II" denotes oestradiol 17β-hydroxysteroid dehydrogenase Type II or ocstradiol 17β-hydroxysteroid dehydrogenase Type 2 and/or 8.

According to one aspect of the present invention, there is provided a compound having Formula I

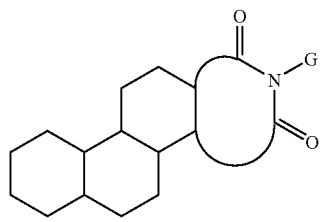

Formula I wherein G is H or a substituent.

According to one aspect of the present invention, there is provided a pharmaceutical composition comprising a compound having Formula I

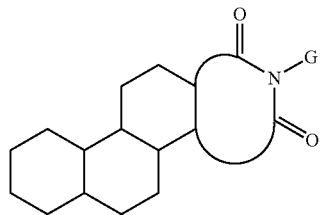

Formula I wherein G is H or a substituent, admixed with a pharmaceutically acceptable carrier, diluent, excipient or adjuvant.

According to one aspect of the present invention, there is provided a compound having Formula I

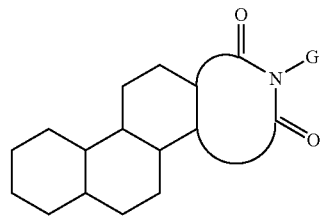

Formula I wherein G is H or a substituent, for use in medicine.

According to one aspect of the present invention, there is provided use of a compound a compound having Formula I

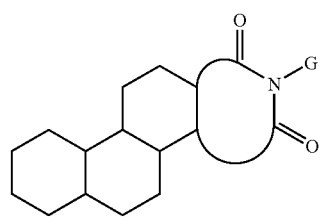

Formula I wherein G is H or a substituent, in the manufacture of a medicament for use in the therapy of a condition or disease associated with steroid sulphatase (STS).

According to one aspect of the present invention, there is provided use of a compound having Formula I

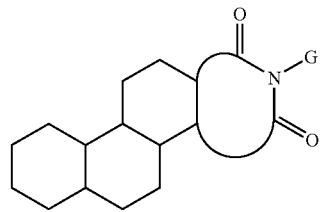

Formula I wherein G is H or a substituent, in the manufacture of a medicament for use in the therapy of a condition or disease associated with adverse STS levels.

According to one aspect of the present invention, there is provided use of a compound having Formula I

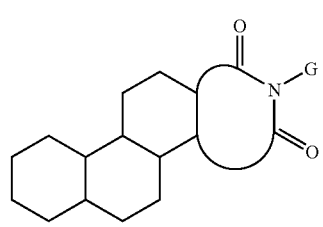

Formula I wherein G is H or a substituent, in the manufacture of a pharmaceutical for inhibiting steroid sulphatase (STS) activity.

According to one aspect of the present invention, there is provided a method of inhibiting steroid sulphatase (STS) activity in a subject in need of same, the method comprising administering a compound a compound having Formula I

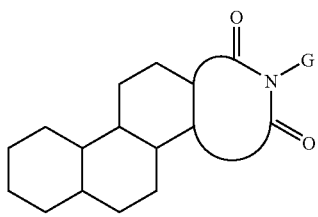

Formula I wherein G is H or a substituent.

According to one aspect of the present invention, there is provided use of a compound having Formula I

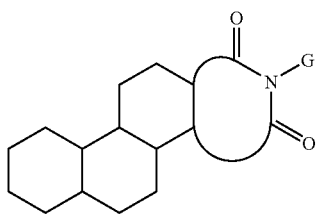

Formula I wherein G is H or a substituent, in the manufacture of a pharmaceutical for modulating and/or arresting and/or inhibiting cell cycling and/or for modulating and/or inducing apoptosis.

For ease of reference, these and further aspects of the present invention are now discussed under appropriate section headings. However, the teachings under each section are not necessarily limited to each particular section.

Preferable Aspects

Ring System

In some aspects of the present invention, preferably the compound has Formula II

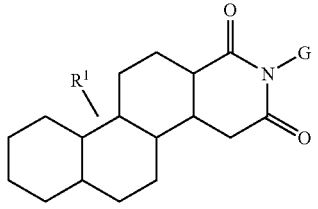

Formula II wherein G is H or a substituent, and wherein $R^1$ is any one of a sulphamate group, a phosphonate group, a thiophosphonate group, a sulphonate group or a sulphonamide group.

In some aspects of the present invention, preferably the compound has Formula III

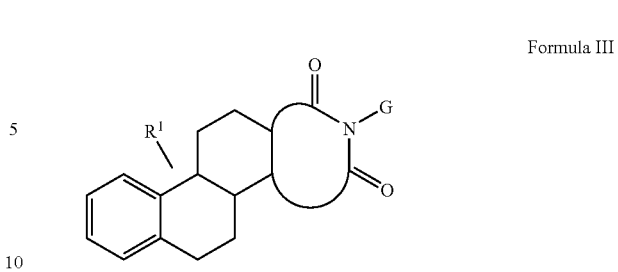

Formula III wherein G is H or a substituent, and wherein $R^1$ is any one of a sulphamate group, a phosphonate group, a thiophosphonate group, a sulphonate group or a sulphonamide group.

In some aspects of the present invention, preferably the compound has Formula IV

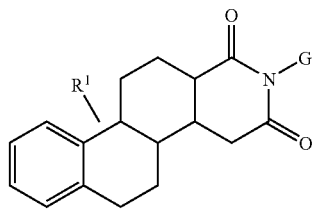

Formula IV wherein G is H or a substituent, and wherein $R^1$ is any one of a sulphamate group, a phosphonate group, a thiophosphonate group, a sulphonate group or a sulphonamide group.

In some aspects of the present invention, preferably the compound has Formula V

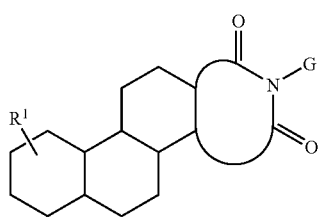

Formula V wherein G is H or a substituent, and wherein $R^1$ is any one of a sulphamate group, a phosphonate group, a thiophosphonate group, a sulphonate group or a sulphonamide group.

In some aspects of the present invention, preferably the compound has Formula VI

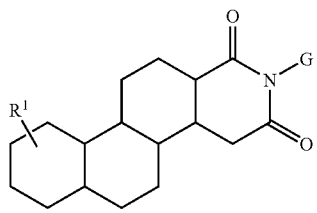

Formula VI wherein G is H or a substituent, and wherein $R^1$ is any one of a sulphamate group, a phosphonate group, a thiophosphonate group, a sulphonate group or a sulphonamide group.

In some aspects of the present invention, preferably the compound has Formula VII Formula VII

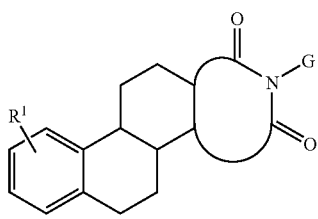

wherein G is H or a substituent, and wherein $R^1$ is any one of a sulphamate group, a phosphonate group, a thiophosphonate group, a sulphonate group or a sulphonamide group.

In some aspects of the present invention, preferably the compound has Formula VIII Formula VIII

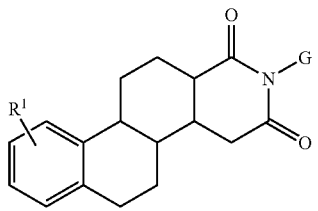

wherein G is H or a substituent, and wherein $R^1$ is any one of a sulphamate group, a phosphonate group, a thiophosphonate group, a sulphonate group or a sulphonamide group.

In some aspects of the present invention, preferably the compound has Formula IX Formula IX

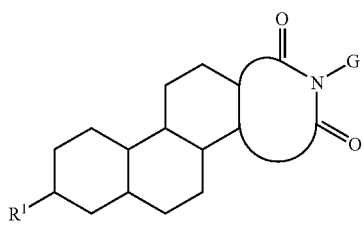

wherein G is H or a substituent, and wherein $R^1$ is any one of a sulphamate group, a phosphonate group, a thiophosphonate group, a sulphonate group or a sulphonamide group.

In some aspects of the present invention, preferably the compound has Formula X

Formula X

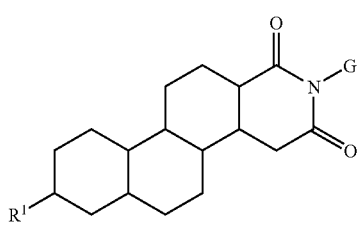

wherein G is H or a substituent, and wherein $R^1$ is any one of a sulphamate group, a phosphonate group, a thiophosphonate group, a sulphonate group or a sulphonamide group.

In some aspects of the present invention, preferably the compound has Formula XI Formula XI

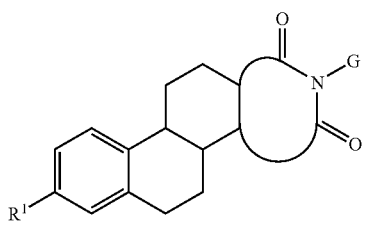

wherein G is H or a substituent, and wherein $R^1$ is any one of a sulphamate group, a phosphonate group, a thiophosphonate group, a sulphonate group or a sulphonamide group.

In some aspects of the present invention, preferably the compound has Formula XII Formula XII

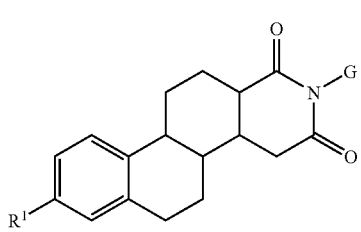

wherein G is H or a substituent, and wherein $R^1$ is any one of a sulphamate group, a phosphonate group, a thiophosphonate group, a sulphonate group or a sulphonamide group.

As it is well known in the art, a classical steroidal ring structure has the generic formula of:

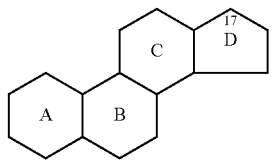

In the above formula, the rings have been labelled in the conventional manner.

An example of a bio-isostere is when any one or more of rings A, B, C and D is a heterocyclic ring and/or when any one or more of rings A, B, C and D has been substituted and/or when any one or more of rings A, B, C and D has been modified; but wherein the bio-isostere has steroidal properties.

In this regard, the ring system of the present invention is analogous to a steroidal ring structure and may be a bio-isostere of a steroidal ring structure.

The structure of a present polycyclic structure can be presented as:

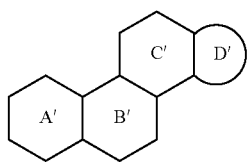

wherein each ring A', B', and C' independently represents a heterocyclic ring or a non-heterocyclic ring, and wherein each ring may be independently substituted or unsubstituted, saturated or unsaturated.

By way of example, any one or more of rings A', B', C' and D' may be independently substituted with suitable groups—such as an alkyl group, an aryl group, a hydroxy group, a halo group, a hydrocarbyl group, an oxyhydrocarbyl group etc.

At least one of A', B', and C' may be a heterocyclic group (a heterocycle) or a non-heterocyclic group.

At least one of A', B', C' and D' may be a saturated ring structure or an unsaturated ring structure (such as an aryl group).

Preferably, at least one of A', B', C' and D' is an aryl ring.

Preferably the compound will contain, inclusive of all substituents, no more than 50 about carbon atoms, more usually no more than about 30 to 40 carbon atoms.

An example of D' is a five or six membered ring.

Preferred steroidal nuclei rings A'-D' on which the compounds of the present invention may be based include rings A-D of:

Oestrones and Substituted Oestrones, viz:

| | |
|---|---|
| oestrone | 16β-OH-oestrone |
| 4-OH-oestrone | 17-deoxyoestrone |
| 6α-OH-oestrone | 2-OH-oestrone |
| 7α-OH-oestrone | 2-MeO-oestrone |
| 16α-OH-oestrone | oestrone |

Oestradiols and Substituted Oestradiols, viz:

| | |
|---|---|
| 4-OH-17β-oestradiol | 16β-OH-17β-oestradiol |
| 6α-OH-17β-oestradiol | 17α-oestradiol |
| 7α-OH-17β-oestradiol | 17β-oestradiol |
| 4-OH-17α-oestradiol | 17α-ethinyl-17β-oestradiol |
| 6α-OH-17α-oestradiol | 17β-ethinyl-17α-oestradiol |
| 7α-OH-17α-oestradiol | 17-deoxyoestradiol |
| 16α-OH-17α-oestradiol | 2-OH-17α-oestradiol |
| 16α-OH-17β-oestradiol | 2-OH-17β-oestradiol |
| 16β-OH-17α-oestradiol | 2-MeO-17α-oestradiol |
| | 2-MeO-17β-oestradiol |

Oestriols and Substituted Oestriols, viz:

| | |
|---|---|
| oestriol | 17-deoxyoestriol |
| 4-OH-oestriol | 2-OH-oestriol |
| 6α-OH-oestriol | 2-MeO-oestriol |
| 7α-OH-oestriol | |

Dehydroepiandrosterones and Substituted Dehydroepiandrosterones, viz:

| | |
|---|---|
| dehydroepiandrosterones | 16α-OH-dehydroepiandrosterone |
| 6α-OH-dehydroepiandrosterone | 16β-OH-dehydroepiandrosterone |
| 7α-OH-dehydroepiandrosterone | 5-androstenediol |

Group G

In some aspects of the present invention, preferably G is selected from H, OH and a hydrocarbyl group.

In some aspects of the present invention, preferably G or the hydrocarbyl group is an optionally substituted hydrocarbon group. In other words G is an optionally substituted hydrocarbon group or is selected from H, OH and an optionally substituted hydrocarbon group.

In some aspects of the present invention, preferably G or the hydrocarbyl group is selected from optionally substituted alkyl group, optionally substituted haloalkyl group, aryl group, alkylaryl group, alkylarylakyl group, and an alkene group.

In some aspects of the present invention, preferably G or the hydrocarbyl group is an optionally substituted alkyl group.

In some aspects of the present invention, preferably G or the hydrocarbyl group is selected from $C_1$-$C_{10}$ alkyl group, such as $C_1$-$C_6$ alkyl group, and $C_1$-$C_3$ alkyl group. Typical alkyl groups include $C_1$ alkyl, $C_2$ alkyl, $C_3$ alkyl, $C_4$ alkyl, $C_5$ alkyl, $C_7$ alkyl, and $C_8$ alkyl.

In some aspects of the present invention, preferably G or the hydrocarbyl group is selected from $C_1$-$C_{10}$ haloalkyl group, $C_1$-$C_6$ haloalkyl group, $C_1$-$C_3$ haloalkyl group, $C_1$-$C_{10}$ bromoalkyl group, $C_1$-$C_6$ bromoalkyl group, and $C_1$-$C_3$ bromoalkyl group. Typical haloalkyl groups include $C_1$ haloalkyl, $C_2$ haloalkyl, $C_3$ haloalkyl, $C_4$ haloalkyl, $C_5$ haloalkyl, $C_7$ haloalkyl, $C_8$ haloalkyl, $C_1$ bromoalkyl, $C_2$ bromoalkyl, $C_3$ bromoalkyl, $C_4$ bromoalkyl, $C_5$ bromoalkyl, $C_7$ bromoalkyl, and $C_8$ bromoalkyl.

In some aspects of the present invention, preferably G or the hydrocarbyl group is selected from aryl groups, alkylaryl groups, alkylarylakyl groups, —$(CH_2)_{1-10}$-aryl, —$(CH_2)_{1-10}$-Ph, $(CH_2)_{1-10}$-Ph-$C_{1-10}$ alkyl, —$(CH_2)_{1-5}$-Ph, $(CH_2)_{1-5}$-Ph-$C_{1-5}$ alkyl, —$(CH_2)_{1-3}$-Ph, $(CH_2)_{1-3}$-Ph-$C_{1-3}$ alkyl, —$CH_2$-Ph, and —$CH_2$-Ph-$C(CH_3)_3$.

When G or the hydrocarbyl group is or contains an aryl group, the aryl group or one or more of the aryl groups may contain a hetero atom. Thus the aryl group or one or more of the aryl groups may be carbocyclic or more may heterocyclic. Typical hetero atoms include O, N and S, in particular N.

In some aspects of the present invention, preferably G or the hydrocarbyl group is selected from —$(CH_2)_{1-10}$-cycloalkyl, —$(CH_2)_{1-10}$—$C_{3-10}$cycloalkyl, —$(CH_2)_{1-7}$—$C_{3-7}$cycloalkyl, —$(CH_2)_{1-5}$—$C_{3-5}$cycloalkyl, —$(CH_2)_{1-3}$—$C_{3-5}$cycloalkyl, and —$CH_2$—$C_3$cycloalkyl.

In some aspects of the present invention, preferably G or the hydrocarbyl group is an alkene group. Typical alkene groups include $C_1$-$C_{10}$ alkene group, $C_1$-$C_6$ alkene group, $C_1$-$C_3$ alkene group, such as $C_1$, $C_2$, $C_3$, $C_4$, $C_5$, $C_6$, or $C_7$ alkene group. In a preferred aspect the alkene group contains 1, 2 or 3 C=C bonds. In a preferred aspect the alkene group contains 1 C=C bond. In some preferred aspect at least one C=C bond or the only C=C bond is to the terminal C of the alkene chain, that is the bond is at the distal end of the chain to the ring system.

In some aspects of the present invention, preferably G is H.

$R^1$ Group

Group $R^1$ of the compounds of the present invention is any one of a sulphamate group, a phosphonate group, a thiophosphonate group, a sulphonate group or a sulphonamide group.

In one preferred aspect $R^1$ is preferably a sulphamate group.

$R^1$ or the sulphamate group may be a sulphamate group of the formula

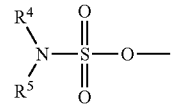

wherein $R^4$ and $R^5$ are independently selected from H, alkyl, cycloalkyl, alkenyl and aryl, or combinations thereof, or together represent alkylene, wherein the or each alkyl or cycloalkyl or alkenyl or optionally contain one or more hetero atoms or groups.

In some aspects of the present invention, preferably at least one of $R^4$ and $R^5$ is H.

In some aspects of the present invention, preferably $R^4$ and $R^5$ are H.

Substituents

The compound of the present invention may have substituents other than those of the ring systems show herein. Furthermore the ring systems herein are given as general formulae and should be interpreted as such. The absence of any specifically shown substituents on a given ring member indicates that the ring member may substituted with any moiety of which H is only one example. The ring system may contain one or more degrees of unsaturation, for example is some aspects one or more rings of the ring system is aromatic. The ring system may be carbocyclic or may contain one or more hetero atoms.

The compound of the invention, in particular the ring system compound of the invention of the present invention may contain substituents other than those show herein. By way of example, these other substituents may be one or more of: one or more sulphamate group(s), one or more phosphonate group(s), one or more thiophosphonate group(s), one or more sulphonate group(s), one or more sulphonamide group(s), one or more halo groups, one or more O groups, one or more hydroxy groups, one or more amino groups, one or more sulphur containing group(s), one or more hydrocarbyl group(s)—such as an oxyhydrocarbyl group.

In general terms the ring system A'B'C'D' of the present compounds may contain a variety of non-interfering substituents. In particular, the ring system A'B'C'D' may contain one or more hydroxy, alkyl especially lower ($C_1$-$C_6$) alkyl, e.g. methyl, ethyl, n-propyl, isopropyl, n-butyl, sec-butyl, tert-butyl, n-pentyl and other pentyl isomers, and n-hexyl and other hexyl isomers, alkoxy especially lower ($C_1$-$C_6$) alkoxy, e.g. methoxy, ethoxy, propoxy etc., alkinyl, e.g. ethinyl, or halogen, e.g. fluoro substituents.

For some compounds of the present invention, it is preferred that the ring system is substituted with a hydrocarbylsulphanyl group. More preferably the A' ring of the ring system is substituted with a hydrocarbylsulphanyl group. The term "hydrocarbylsulphanyl" means a group that comprises at least hydrocarbyl group (as herein defined) and sulphur, preferably —S-hydrocarbyl, more preferably —S-hydrocarbon. That sulphur group may be optionally oxidised.

For some compounds of the present invention, it is highly preferred that at least the 2 position of the A' ring of the ring system is substituted with a hydrocarbylsulphanyl group.

Preferably the hydrocarbylsulphanyl group is —S—$C_{1-10}$ alkyl, more preferably —S—$C_{1-5}$ alkyl, more preferably —S—$C_{1-3}$ alkyl, more preferably —S—$CH_2CH_2CH_3$, —S—$CH_2CH_3$ or —$SCH_3$ For some compounds of the present invention, it is highly preferred that the A' ring of the ring system is substituted with an alkoxy group.

For some compounds of the present invention, it is highly preferred that at least the 2 position of the A' ring of the ring system is substituted with an alkoxy group.

Preferably the alkoxy group is methoxy.

For some compounds of the present invention, it is highly preferred that the A' ring of the ring system is substituted with an hydrocarbyl group.

For some compounds of the present invention, it is highly preferred that at least the 2 position of the A' ring of the ring system is substituted with an alkyl group.

Preferably the alkyl group is ethyl.

For some compounds of the present invention, it is highly preferred that the compound comprises at least two or more of sulphamate group, a phosphonate group, a thiophosphonate group, a sulphonate group or a sulphonamide group.

For some compounds of the present invention, it is highly preferred that the compound comprises at least two sulphamate groups.

For some compounds of the present invention, it is highly preferred that the compound comprises at least two sulphamate groups, wherein said sulphamate groups are not on the same ring.

For some compounds of the present invention, it is highly preferred that the A' ring of the ring system comprises at least one sulphamate group and wherein the D' ring of the ring system comprises at least one sulphamate group.

In some aspects of the present invention, preferably the A' ring contain one or more of an alkoxy substituent and an alkyl substituent. Thus according to one aspect of the present invention, there is provided a compound having Formula XIII

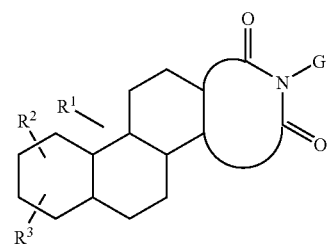

Formula XIII wherein $R^2$ and $R^3$ are independently selected from H and hydrocarbyl groups, wherein at least one of $R^2$ and $R^3$ is a hydrocarbyl group.

In preferred aspects of the present invention, there is provided a compound selected from compounds having Formula XIV to XIX

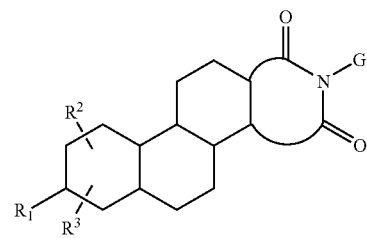

Formula XIV

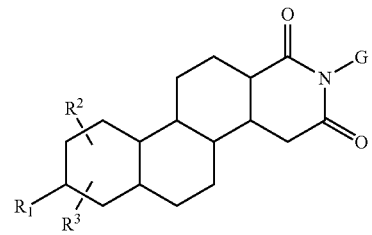

Formula XV

Formula XVI

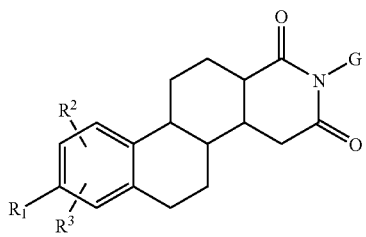

Formula XVII

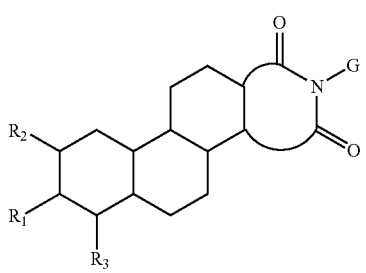

Formula XVIII

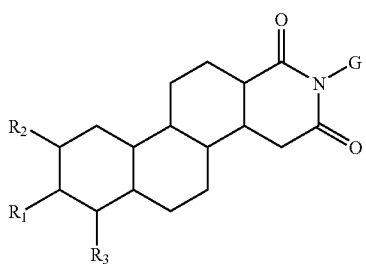

Formula XIX

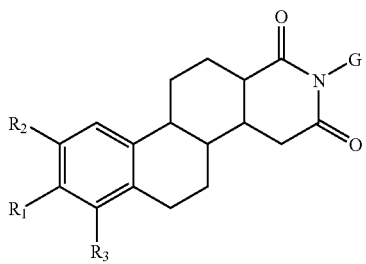

wherein $R^2$ and $R^3$ are independently selected from H and hydrocarbyl groups, wherein at least one of $R^2$ and $R^3$ is a hydrocarbyl group.

Preferably at least one of $R^2$ and $R^3$ is an alkyl group. Preferably at least one of $R^2$ and $R^3$ is $C_1$-$C_{10}$ alkyl group, preferably $C_1$-$C_6$ alkyl group, preferably $C_1$-$C_3$ alkyl group. Preferably at least one of $R^2$ and $R^3$ is —$CH_3$ or —$CH_2CH_3$.

In one aspect preferably $R^2$ is a hydrocarbyl group and $R^3$ is H.

In another preferred aspect, at least one of $R^2$ and $R^3$ is an alkoxy group. Preferably at least one of $R^2$ and $R^3$ is methoxy.

Highly preferred compounds of the present invention may be selected from

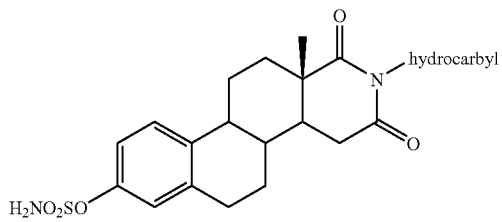

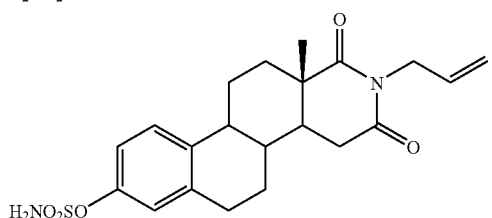

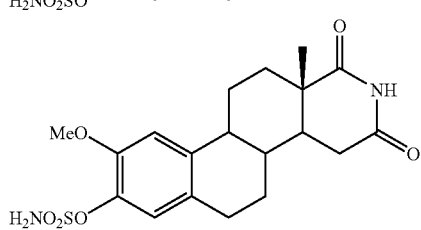

wherein

R = $CH_3$                and  $R_2$ = H
R = $CH_2CH_3$                 $R_2$ = OMe
R = $(CH_2)_2CH_3$             $R_2$ = —S—Me
R = $CH_2CHCH_2$
R = $(CH_2)_3CH_3$
R = $(CH_2)_4CH_3$
R = $(CH_2)_5CH_3$
R = $(CH_2)_3Br$
R = $CH_2$—△

R = $CH_2$—[pyridyl]

R = $CH_2$—[C6H4]—$C(CH_3)_3$

R = $CH_2$—[phenyl]

Further Aspects

According to a further aspect of the present invention there is provided a method comprising (a) performing a steroid sulphatase assay with one or more candidate compounds having the formula as defined herein; (b) determining whether one or more of said candidate compounds is/are capable of modulating STS activity; and (c) selecting one or more of said candidate compounds that is/are capable of modulating STS activity.

According to a further aspect of the present invention there is provided a method comprising (a) performing a steroid sulphatase assay with one or more candidate compounds having the formula as defined herein; (b) determining whether one or more of said candidate compounds is/are capable of inhibiting STS activity; and (c) selecting one or more of said candidate compounds that is/are capable of inhibiting STS activity.

In any one of the methods of the present invention, one or more additional steps may be present. For example, the method may also include the step of modifying the identified candidate compound (such as by chemical and/or enzymatic techniques) and the optional additional step of testing that modified compound for STS inhibition effects (which may be to see if the effect is greater or different). By way of further example, the method may also include the step of determining the structure (such as by use of crystallographic techniques) of the identified candidate compound and then performing computer modelling studies—such as to further increase its STS inhibitory action. Thus, the present invention also encompasses a computer having a dataset (such as the crystallographic co-ordinates) for said identified candidate compound. The present invention also encompasses that identified candidate compound when presented on a computer screen for the analysis thereof—such as protein binding studies.

According to one aspect of the present invention, there is provided a compound identified by the method of the present invention.

According to one aspect of the present invention, there is provided a compound according to the present invention for use in medicine.

According to one aspect of the present invention, there is provided a pharmaceutical composition comprising the compound according to the present invention optionally admixed with a pharmaceutically acceptable carrier, diluent, excipient or adjuvant.

According to one aspect of the present invention, there is provided the use of a compound according to the present invention in the manufacture of a medicament for use in the therapy of a condition or disease associated with STS According to one aspect of the present invention, there is provided the use of a compound according to the present invention in the manufacture of a medicament for use in the therapy of a condition or disease associated with adverse STS levels.

For some applications, preferably the compounds have no, or a minimal, oestrogenic effect.

For some applications, preferably the compounds have an oestrogenic effect.

For some applications, preferably the compounds have a reversible action.

For some applications, preferably the compounds have an irreversible action.

In one embodiment, the compounds of the present invention are useful for the treatment of breast cancer.

The compounds of the present invention may be in the form of a salt.

The present invention also covers novel intermediates that are useful to prepare the compounds of the present invention. For example, the present invention covers novel alcohol precursors for the compounds. By way of further example, the present invention covers bis protected precursors for the compounds. Examples of each of these precursors are presented herein. The present invention also encompasses a process comprising each or both of those precursors for the synthesis of the compounds of the present invention.

We have also identified that in some aspects of the present invention the present compounds may also inhibit the activity of steroid dehydrogenase (HSD).

By steroid dehydrogenase or HSD it is meant 17β hydroxy steroid dehydrogenase. In one aspect the 17β hydroxy steroid dehydrogenase is EC 1.1.1.62

Preferably the HSD is of Type 1, 3, 5 and/or 7. Preferably the HSD converts oestrone (ketone) to oestradiol (hydroxy).

Preferably the HSD is of Type 2 and/or 8. Preferably the HSD converts oestradiol (hydroxy) to oestrone (ketone).

Thus in further aspects the present invention provides

Use of a compound of the present invention in the manufacture of a medicament for use in the therapy of a condition or disease associated with steroid dehydrogenase.

Use of a compound of the present invention in the manufacture of a medicament for use in the therapy of a condition or disease associated with adverse steroid dehydrogenase levels.

Use of a compound of the present invention in the manufacture of a pharmaceutical for inhibiting steroid dehydrogenase activity.

Use of a compound of the present invention in the manufacture of a pharmaceutical for inhibiting steroid dehydrogenase activity.

A method comprising (a) performing a steroid dehydrogenase assay with one or more candidate compounds of the present invention; (b) determining whether one or more of said candidate compounds is/are capable of modulating steroid dehydrogenase activity; and (c) selecting one or more of said candidate compounds that is/are capable of modulating steroid dehydrogenase activity.

A method comprising (a) performing a steroid dehydrogenase assay with one or more candidate compounds of the present invention; (b) determining whether one or more of said candidate compounds is/are capable of inhibiting steroid dehydrogenase activity; and (c) selecting one or more of said candidate compounds that is/are capable of inhibiting steroid dehydrogenase activity.

A compound identified by the above methods, their use in medicine and pharmaceutical composition comprising the compounds optionally admixed with a pharmaceutically acceptable carrier, diluent, excipient or adjuvant.

In some aspects of the present invention, it is preferred that the steroid dehydrogenase is steroid dehydrogenase Type I.

In some aspects of the present invention, it is preferred that the steroid dehydrogenase is steroid dehydrogenase Type II Preferably the HSD is of Type 1, 3, 5 and/or 7. Preferably the HSD converts oestrone (ketone) to oestradiol (hydroxy).

Preferably the HSD is of Type 2 and/or 8. Preferably the HSD converts oestradiol (hydroxy) to oestrone (ketone).

We have also identified that in some aspects it is not necessary for the compounds of the present invention to be substituted with one of a sulphamate group, a phosphonate group, a thiophosphonate group, a sulphonate group or a sulphonamide group, to inhibit the activity of steroid dehydrogenase (HSD). Thus in some aspects the present invention provides a compound as defined herein wherein R1 is any substituent. In this aspect preferably R1 is H, OH or a hydrocarbyl group, more preferably OH.

Data confirming this finding are given in Table 2 below

TABLE 2

| STX No. | Structure | % Inhibition * $E_1 \to E_2 \pm SD$ (HSD Type I) | % Inhibition * $E_2 \to E_1 \pm SD$ (HSD Type II) |
| --- | --- | --- | --- |
| 187 | 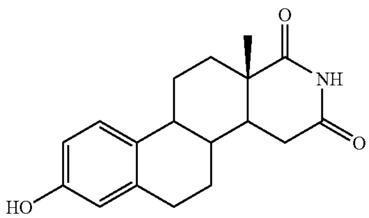 | 25.27 ± 2.20 | −15.40 ± 0.41 |
| 188 | 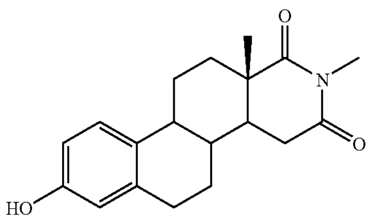 | 32.99 ± 1.79 | −3.51 ± 2.44 |
| 189 | 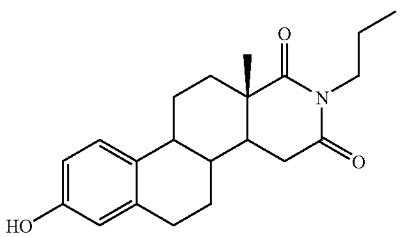 | 16.96 ± 3.25 | 5.05 ± 2.31 |
| 190 | 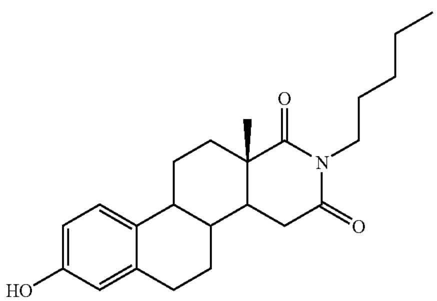 | 24.08 ± 4.59 | 0.48 ± 4.76 |
| 213 | 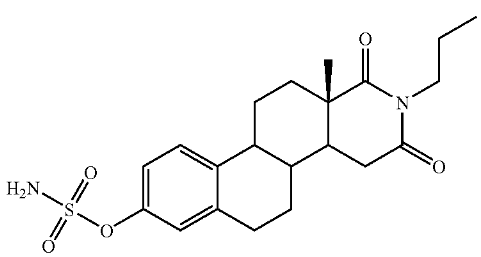 | 22.50 ± 1.62 | 14.30 ± 14.84 |
| 233 | 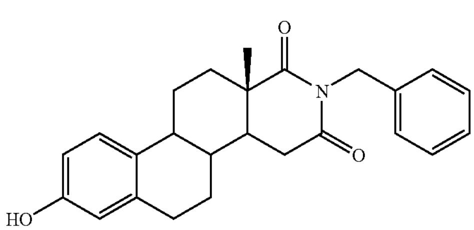 | 58.78 ± 0.68<br>57.43 ± 1.89 | 35.76 ± 3.88 |

TABLE 2-continued
| STX No. | Structure | % Inhibition * $E_1 \rightarrow E_2 \pm SD$ (HSD Type I) | % Inhibition * $E_2 \rightarrow E_1 \pm SD$ (HSD Type II) |
|---|---|---|---|
| 234 | 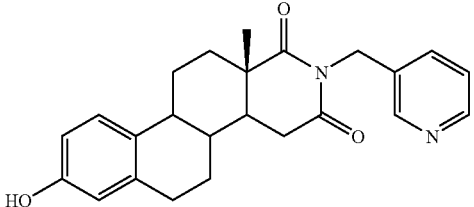 | 25.84 ± 9.27 | −1.45 ± 11.44 |
| 235 | 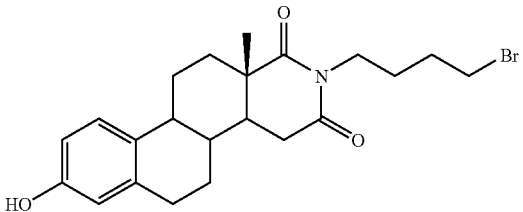 | 16.65 ± 1.46 | 10.68 ± 0.78 |
| 236 | 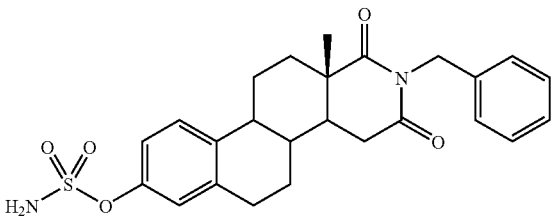 | 20.39 ± 6.25 | 5.84 ± 11.81 |
| 237 | 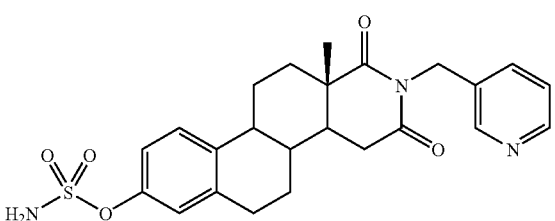 | −2 | 255 |
| 274 | 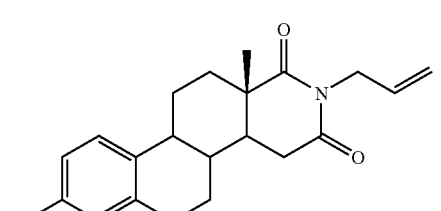 | 36.82 ± 0.36 | −4.04 ± 0.36 |
| 275 | 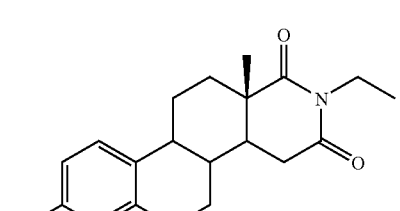 | 42.45 ± 3.02 | 32.09 ± 1.06 |

TABLE 2-continued

| STX No. | Structure | % Inhibition * $E_1 \rightarrow E_2 \pm SD$ (HSD Type I) | % Inhibition * $E_2 \rightarrow E_1 \pm SD$ (HSD Type II) |
|---|---|---|---|
| 276 | 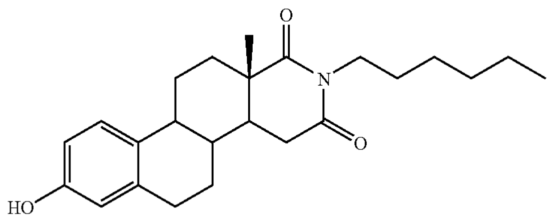 | 22.74 ± 2.20 | 8.32 ± 7.50 |
| 277 | 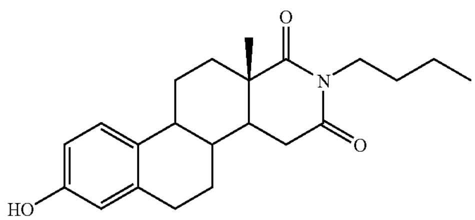 | 18.57 ± 0.89 | 13.25 ± 9.74 |
| 278 | 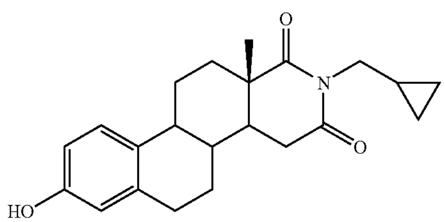 | 24.17 ± 1.71 | 8.31 ± 2.46 |
| 279 | 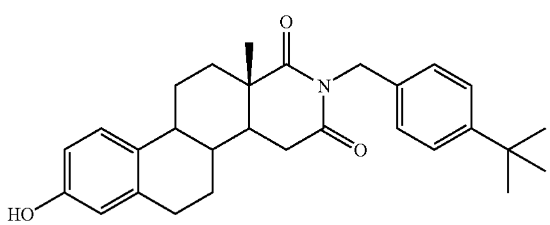 | 16.03 ± 0.88 | 3.87 ± 4.97 |
| 281 | 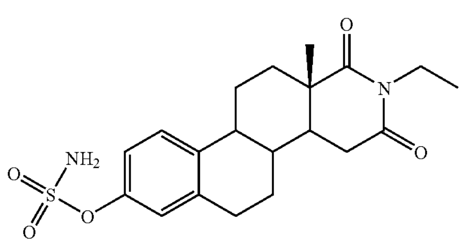 | 24.70 ± 2.39 | 20.39 ± 3.14 |
| 285 | 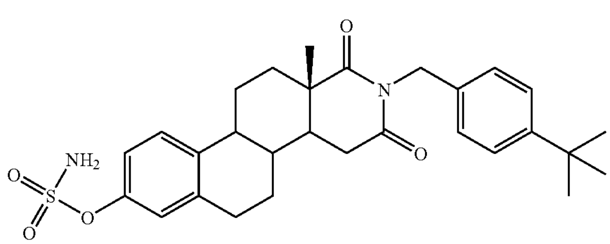 | 22.48 ± 3.72 | 3.56 ± 4.89 |

TABLE 2-continued

| STX No. | Structure | % Inhibition * $E_1 \rightarrow E_2 \pm SD$ (HSD Type I) | % Inhibition * $E_2 \rightarrow E_1 \pm SD$ (HSD Type II) |
|---|---|---|---|
| 286 | 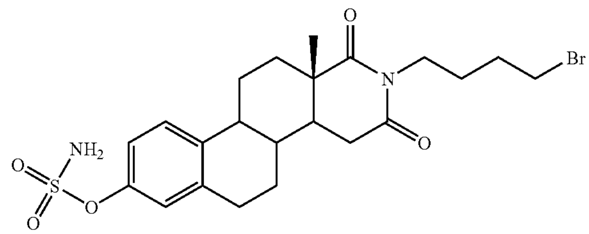 | 25.99 ± 3.23 | −2.98 ± 0.38 |
| 325 | 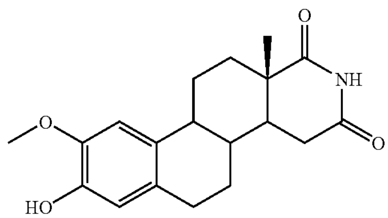 | 7.78 ± 2.45 | −20.19 ± 14.80 |
| 326 | 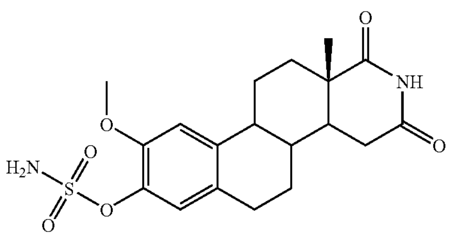 | 7.50 ± 12.44 | 15.01 ± 1.22 |

* measured at 10 μM

Thus in further aspects the present invention provides a compound having the formula

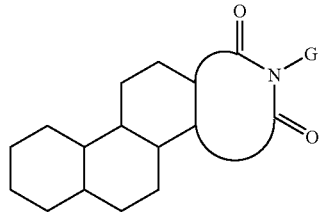

wherein G is H or a substituent,

Use of the compound in the manufacture of a medicament for use in the therapy of a condition or disease associated with steroid dehydrogenase.

Use of the compound in the manufacture of a medicament for use in the therapy of a condition or disease associated with adverse steroid dehydrogenase levels.

Use of the compound in the manufacture of a pharmaceutical for inhibiting steroid dehydrogenase activity.

Use of the compound in the manufacture of a pharmaceutical for inhibiting steroid dehydrogenase activity.

A method comprising (a) performing a steroid dehydrogenase assay with one or more candidate compounds having the above formula; (b) determining whether one or more of said candidate compounds is/are capable of modulating steroid dehydrogenase activity; and (c) selecting one or more of said candidate compounds that is/are capable of modulating steroid dehydrogenase activity.

A method comprising (a) performing a steroid dehydrogenase assay with one or more candidate compounds having the above formula; (b) determining whether one or more of said candidate compounds is/are capable of inhibiting steroid dehydrogenase activity; and (c) selecting one or more of said candidate compounds that is/are capable of inhibiting steroid dehydrogenase activity.

A compound identified by the above methods, their use in medicine and pharmaceutical composition comprising the compounds optionally admixed with a pharmaceutically acceptable carrier, diluent, excipient or adjuvant.

Further broad aspects of the invention are defined below:

a compound comprising a ring system of the formula

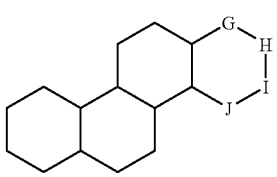

wherein at least one G, H, I and J is a substituted nitrogen.

By the term "substituted nitrogen" it is meant the nitrogen is attached to a group other than H.

Preferably the N is attached to a hydrocarbyl group.

preferably
wherein the other of G, H, I and J are carbon.
only one of G, H, I and J is a substituted nitrogen.
H is a substituted nitrogen.
at least one of G, H, I and J are C=O.

two of G, H, I and J are C═O.
two of G, and I are C═O
a ring system of the formula

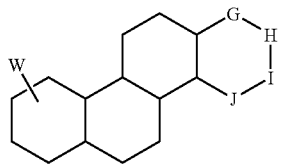

wherein W is —S-alkyl or —O-alkyl(alkoxy).
a ring system of the formula

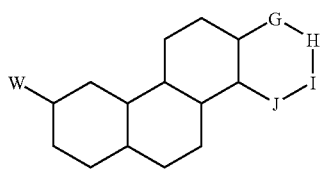

wherein W is —S-alkyl or —O-alkyl(alkoxy).
a ring system of the formula

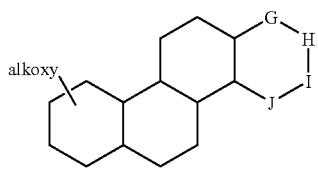

a ring system of the formula

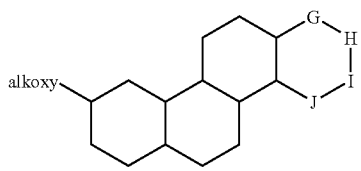

a compound having the Formula

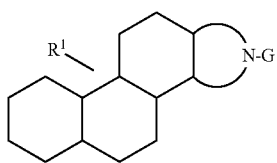

wherein $R^1$ is any one of a sulphamate group, a phosphonate group, a thiophosphonate group, a sulphonate group or a sulphonamide group; and wherein G is H or a substituent.

preferably
a compound having the Formula

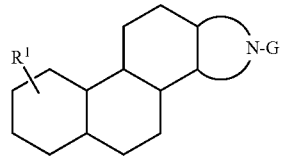

a compound having the Formula

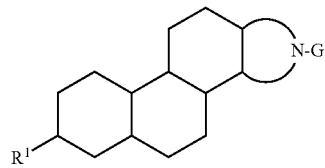

a compound having the Formula

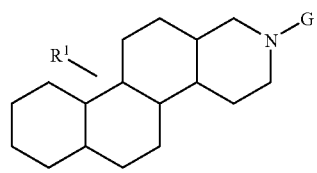

a compound having the Formula

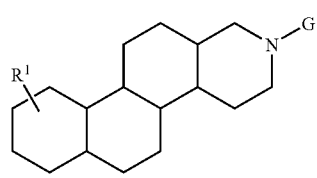

a compound having the Formula

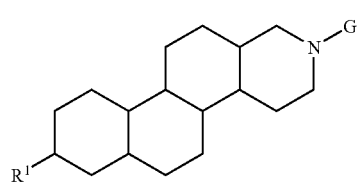

Some Advantages

One key advantage of the present invention is that the compounds of the present invention can act as STS inhibitors.

Another advantage of the compounds of the present invention is that they may be potent in vivo.

Some of the compounds of the present invention may be non-oestrogenic compounds. Here, the term "non-oestrogenic" means exhibiting no or substantially no oestrogenic activity.

Another advantage is that some of the compounds may not be capable of being metabolised to compounds which display or induce hormonal activity.

Some of the compounds of the present invention are also advantageous in that they may be orally active.

Some of the compounds of the present invention may useful for the treatment of cancer, such as breast cancer, as well as (or in the alternative) non-malignant conditions, such as the prevention of auto-immune diseases, particularly when pharmaceuticals may need to be administered from an early age.

Thus, some of the compounds of the present invention are also believed to have therapeutic uses other than for the treatment of endocrine-dependent cancers, such as the treatment of autoimmune diseases.

Steroid Sulphatase

Steroid sulphatase—which is sometimes referred to as steroid sulphatase or steryl sulphatase or "STS" for short—hydrolyses several sulphated steroids, such as oestrone sulphate, dehydroepiandrosterone sulphate and cholesterol sulphate. STS has been allocated the enzyme number EC 3.1.6.2.

STS has been cloned and expressed. For example see Stein et al (J. Biol. Chem. 264:13865-13872 (1989)) and Yen et al (Cell 49:443-454 (1987)).

STS is an enzyme that has been implicated in a number of disease conditions.

By way of example, workers have found that a total deficiency in STS produces ichthyosis. According to some workers, STS deficiency is fairly prevalent in Japan. The same workers (Sakura et al, J Inherit Metab Dis 1997 November; 20(6):807-10) have also reported that allergic diseases—such as bronchial asthma, allergic rhinitis, or atopic dermatitis—may be associated with a steroid sulphatase deficiency.

In addition to disease states being brought on through a total lack of STS activity, an increased level of STS activity may also bring about disease conditions. By way of example, and as indicated above, there is strong evidence to support a role of STS in breast cancer growth and metastasis.

STS has also been implicated in other disease conditions. By way of example, Le Roy et al (Behav Genet. 1999 March; 29(2):131-6) have determined that there may be a genetic correlation between steroid sulphatase concentration and initiation of attack behaviour in mice. The authors conclude that sulphatation of steroids may be the prime mover of a complex network, including genes shown to be implicated in aggression by mutagenesis.

STS Inhibition

It is believed that some disease conditions associated with STS activity are due to conversion of a nonactive, sulphated oestrone to an active, nonsulphated oestrone. In disease conditions associated with STS activity, it would be desirable to inhibit STS activity.

Here, the term "inhibit" includes reduce and/or eliminate and/or mask and/or prevent the detrimental action of STS.

STS Inhibitor

In accordance with the present invention, the compound of the present invention is capable of acting as an STS inhibitor.

Here, the term "inhibitor" as used herein with respect to the compound of the present invention means a compound that can inhibit STS activity—such as reduce and/or eliminate and/or mask and/or prevent the detrimental action of STS. The STS inhibitor may act as an antagonist.

The ability of compounds to inhibit oestrone sulphatase activity can be assessed using either intact MCF-7 breast cancer cells or placental microsomes. In addition, an animal model may be used. Details on suitable Assay Protocols are presented in following sections. It is to be noted that other assays could be used to determine STS activity and thus STS inhibition. For example, reference may also be made to the teachings of WO-A-99/50453.

Preferably, for some applications, the compound is further characterised by the feature that if the sulphamate group were to be substituted by a sulphate group to form a sulphate derivative, then the sulphate derivative would be hydrolysable by an enzyme having steroid sulphatase (E.C. 3.1.6.2) activity—i.e. when incubated with steroid sulphatase EC 3.1.6.2 at pH 7.4 and 37° C.

In one preferred embodiment, if the sulphamate group of the compound were to be replaced with a sulphate group to form a sulphate compound then that sulphate compound would be hydrolysable by an enzyme having steroid sulphatase (E.C. 3.1.6.2) activity and would yield a Km value of less than 200 mmolar, preferably less than 150 mmolar, preferably less than 100 mmolar, preferably less than 75 mmolar, preferably less than 50 mmolar, when incubated with steroid sulphatase EC 3.1.6.2 at pH 7.4 and 37° C.

In one preferred embodiment, if the sulphamate group of the compound were to be replaced with a sulphate group to form a sulphate compound then that sulphate compound would be hydrolysable by an enzyme having steroid sulphatase (E.C. 3.1.6.2) activity and would yield a Km value of less than 200 µmolar, preferably less than 150 µmolar, preferably less than 100 µmolar, preferably less than 75 µmolar, preferably less than 50 µmolar, when incubated with steroid sulphatase EC 3.1.6.2 at pH 7.4 and 37° C.

In a preferred embodiment, the compound of the present invention is not hydrolysable by an enzyme having steroid sulphatase (E.C. 3.1.6.2) activity.

For some applications, preferably the compound of the present invention has at least about a 100 fold selectivity to a desired target (e.g. STS), preferably at least about a 150 fold selectivity to the desired target, preferably at least about a 200 fold selectivity to the desired target, preferably at least about a 250 fold selectivity to the desired target, preferably at least about a 300 fold selectivity to the desired target, preferably at least about a 350 fold selectivity to the desired target.

It is to be noted that the compound of the present invention may have other beneficial properties in addition to or in the alternative to its ability to inhibit STS activity.

Steroid Dehydrogenase

Steroid dehydrogenase or "DH" for short may be classified as consisting of two types—Type I and Type II. The two types of enzyme, such as oestradiol 17β-hydroxysteroid dehydrogenases (E2HSD), have pivotal roles in regulating the availability of ligands to interact with the oestrogen receptor. Type I reduces oestrone (E1) to the biologically active oestrogen, oestradiol (E2) while E2HSD Type II inactivates E2 by catalysing its oxidation to E1.

DH Inhibition

It is believed that some disease conditions associated with DH activity are due to conversion of a nonactive, oestrone to an active, oestradiol. In disease conditions associated with DH activity, it would be desirable to inhibit DH activity.

Here, the term "inhibit" includes reduce and/or eliminate and/or mask and/or prevent the detrimental action of DH.

DH Inhibitor

In accordance with the present invention, the compound of the present invention is capable of acting as an DH inhibitor.

Here, the term "inhibitor" as used herein with respect to the compound of the present invention means a compound that can inhibit DH activity—such as reduce and/or eliminate and/or mask and/or prevent the detrimental action of DH. The DH inhibitor may act as an antagonist.

The ability of compounds to inhibit steroid dehydrogenase activity can be assessed using either T47D breast cancer cells in which E2HSD Type I activity is abundant or MDA-MB-231 cells for Type II inhibitor studies. In both cell lines formation of products is linear with respect to time and cell numbers. Details on a suitable Assay Protocol are presented in the Examples section.

It is to be noted that the compound of the present invention may have other beneficial properties in addition to or in the alternative to its ability to inhibit DH activity.

Sulphamate Group

In one embodiment, the ring X has a sulphamate group as a substituent. The term "sulphamate" as used herein includes an ester of sulphamic acid, or an ester of an N-substituted derivative of sulphamic acid, or a salt thereof.

If $R^1$ is a sulphamate group then the compound of the present invention is referred to as a sulphamate compound.

Typically, the sulphamate group has the formula:

$$(R^4)(R^5)N-S(O)(O)-O-$$

wherein preferably $R^4$ and $R^5$ are independently selected from H, alkyl, cycloalkyl, alkenyl and aryl, or combinations thereof, or together represent alkylene, wherein the or each alkyl or cycloalkyl or alkenyl or optionally contain one or more hetero atoms or groups.

When substituted, the N-substituted compounds of this invention may contain one or two N-alkyl, N-alkenyl, N-cycloalkyl or N-aryl substituents, preferably containing or each containing a maximum of 10 carbon atoms. When $R^4$ and/or $R^5$ is alkyl, the preferred values are those where $R^4$ and $R^5$ are each independently selected from lower alkyl groups containing from 1 to 6 carbon atoms, that is to say methyl, ethyl, propyl etc. $R^4$ and $R^5$ may both be methyl. When $R^4$ and/or $R^5$ is aryl, typical values are phenyl and tolyl (PhCH$_3$; o). Where $R^4$ and $R^5$ represent cycloalkyl, typical values are cyclopropyl, cyclopentyl, cyclohexyl etc. When joined together $R^4$ and $R^5$ typically represent an alkylene group providing a chain of 4 to 6 carbon atoms, optionally interrupted by one or more hetero atoms or groups, e.g. to provide a 5 membered heterocycle, e.g. morpholino, pyrrolidino or piperidino.

Within the values alkyl, cycloalkyl, alkenyl and aryl substituted groups are included containing as substituents therein one or more groups which do not interfere with the sulphatase inhibitory activity of the compound in question. Exemplary non-interfering substituents include hydroxy, amino, halo, alkoxy, alkyl and aryl.

In some embodiments, the sulphamate group may form a ring structure by being fused to (or associated with) one or more atoms in or on group X.

In some embodiments, there may be more than one sulphamate group. By way of example, there may be two sulphamates (i.e. bis-sulphamate compounds). If these compounds are based on a steroidal nucleus, preferably the second (or at least one of the additional) sulphamate group is located at position 17 of the steroidal nucleus. These groups need not be the same.

In some preferred embodiments, at least one of $R^4$ and $R^5$ is H.

In some further preferred embodiments, each of $R^4$ and $R^5$ is H.

Phosphonate Group

If $R^1$ is a phosphonate group then the compound of the present invention is referred to as a phosphonate compound.

Typically, the phosphonate group has the formula:

$$(R^6)-P(O)(OH)-O-$$

wherein preferably $R^6$ is H, alkyl, cycloalkyl, alkenyl or aryl, or combinations thereof, wherein the or each alkyl or cycloalkyl or alkenyl or optionally contain one or more hetero atoms or groups.

When substituted, the N-substituted compounds of this invention may contain one or two N-alkyl, N-alkenyl, N-cycloalkyl or N-aryl substituents, preferably containing or each containing a maximum of 10 carbon atoms. When $R^6$ is alkyl, $R^6$ may be a lower alkyl groups containing from 1 to 6 carbon atoms, that is to say methyl, ethyl, propyl etc. By way of example, $R^6$ may be methyl. When $R^6$ is aryl, typical values are phenyl and tolyl (PhCH$_3$; o). Where $R^6$ represents cycloalkyl, typical values are cyclopropyl, cyclopentyl, cyclohexyl etc. $R^6$ may even comprise an alkylene group providing a chain of 4 to 6 carbon atoms, optionally interrupted by one or more hetero atoms or groups, e.g. to provide a 5 membered heterocycle, e.g. morpholino, pyrrolidino or piperidino.

Within the values alkyl, cycloalkyl, alkenyl and aryl substituted groups are included containing as substituents therein one or more groups which do not interfere with the sulphatase inhibitory activity of the compound in question. Exemplary non-interfering substituents include hydroxy, amino, halo, alkoxy, alkyl and aryl.

In some embodiments, the phosphonate group may form a ring structure by being fused to (or associated with) one or more atoms in or on group X.

In some embodiments, there may be more than one phosphonate group. By way of example, there may be two phosphonates (i.e. bis-phosphonate compounds). If these compounds are based on a steroidal nucleus, preferably the second (or at least one of the additional) phosphonate group is located at position 17 of the steroidal nucleus. These groups need not be the same.

Thiophosphonate Group

If $R^1$ is a thiophosphonate group then the compound of the present invention is referred to as a thiophosphonate compound.

Typically, the thiophosphonate group has the formula:

$$(R^7)-P(S)(OH)-O-$$

wherein preferably $R^7$ is H, alkyl, cycloalkyl, alkenyl or aryl, or combinations thereof, wherein the or each alkyl or cycloalkyl or alkenyl or optionally contain one or more hetero atoms or groups.

When substituted, the N-substituted compounds of this invention may contain one or two N-alkyl, N-alkenyl, N-cycloalkyl or N-aryl substituents, preferably containing or each containing a maximum of 10 carbon atoms. When $R^7$ is alkyl, $R^7$ may be a lower alkyl groups containing from 1 to 6 carbon atoms, that is to say methyl, ethyl, propyl etc. By way of example, $R^7$ may be methyl. When $R^7$ is aryl, typical values are phenyl and tolyl (PhCH$_3$; o). Where $R^7$ represents cycloalkyl, typical values are cyclopropyl, cyclopentyl, cyclohexyl etc. $R^7$ may even comprise an alkylene group providing a chain of 4 to 6 carbon atoms, optionally interrupted by one or more hetero atoms or groups, e.g. to provide a 5 membered heterocycle, e.g. morpholino, pyrrolidino or piperidino.

Within the values alkyl, cycloalkyl, alkenyl and aryl substituted groups are included containing as substituents therein one or more groups which do not interfere with the sulphatase inhibitory activity of the compound in question. Exemplary non-interfering substituents include hydroxy, amino, halo, alkoxy, alkyl and aryl.

In some embodiments, the thiophosphonate group may form a ring structure by being fused to (or associated with) one or more atoms in or on group X.

In some embodiments, there may be more than one thiophosphonate group. By way of example, there may be two thiophosphonates (i.e. bis-thiophosphonate compounds). If these compounds are based on a steroidal nucleus, preferably the second (or at least one of the additional) thiophosphonate group is located at position 17 of the steroidal nucleus. These groups need not be the same.

Sulphonate Group

If $R^1$ is a sulphonate group then the compound of the present invention is referred to as a sulphonate compound.

Typically, the sulphonate group has the formula:

wherein preferably $R^8$ is H, alkyl, cycloalkyl, alkenyl or aryl, or combinations thereof, wherein the or each alkyl or cycloalkyl or alkenyl or optionally contain one or more hetero atoms or groups.

When substituted, the N-substituted compounds of this invention may contain one or two N-alkyl, N-alkenyl, N-cycloalkyl or N-aryl substituents, preferably containing or each containing a maximum of 10 carbon atoms. When $R^8$ is alkyl, $R^8$ may be a lower alkyl groups containing from 1 to 6 carbon atoms, that is to say methyl, ethyl, propyl etc. By way of example, $R^8$ may be methyl. When $R^8$ is aryl, typical values are phenyl and tolyl ($PhCH_3$; o). Where $R^8$ represents cycloalkyl, typical values are cyclopropyl, cyclopentyl, cyclohexyl etc. $R^8$ may even comprise an alkylene group providing a chain of 4 to 6 carbon atoms, optionally interrupted by one or more hetero atoms or groups, e.g. to provide a 5 membered heterocycle, e.g. morpholino, pyrrolidino or piperidino.

Within the values alkyl, cycloalkyl, alkenyl and aryl substituted groups are included containing as substituents therein one or more groups which do not interfere with the sulphatase inhibitory activity of the compound in question. Exemplary non-interfering substituents include hydroxy, amino, halo, alkoxy, alkyl and aryl.

In some embodiments, the sulphonate group may form a ring structure by being fused to (or associated with) one or more atoms in or on group X.

In some embodiments, there may be more than one sulphonate group. By way of example, there may be two sulphonates (i.e. bis-sulphonate compounds). If these compounds are based on a steroidal nucleus, preferably the second (or at least one of the additional) sulphonate group is located at position 17 of the steroidal nucleus. These groups need not be the same.

Combination of Sulphonate/Phosphonate/Thiophosphonate/Sulphamate

For some compounds of the present invention there may be present one of a sulphonate as herein defined or a phosphonate as herein defined or a thiophosphonate as herein defined or a sulphamate as herein defined; and another of a sulphonate as herein defined or a phosphonate as herein defined or a thiophosphonate as herein defined or a sulphamate as herein defined. By way of example, the compound of the present invention may comprise one sulphamate group and one phosphonate group.

If these compounds of the present invention are based on a steroidal nucleus, preferably the other of said groups is located at position 17 of the steroidal nucleus.

Hydrocarbyl

The term "hydrocarbyl group" as used herein means a group comprising at least C and H and may optionally comprise one or more other suitable substituents. Examples of such substituents may include halo, alkoxy, nitro, an alkyl group, a cyclic group etc. In addition to the possibility of the substituents being a cyclic group, a combination of substituents may form a cyclic group. If the hydrocarbyl group comprises more than one C then those carbons need not necessarily be linked to each other. For example, at least two of the carbons may be linked via a suitable element or group. Thus, the hydrocarbyl group may contain hetero atoms. Suitable hetero atoms will be apparent to those skilled in the art and include, for instance, sulphur, nitrogen and oxygen. A non-limiting example of a hydrocarbyl group is an acyl group.

A typical hydrocarbyl group is a hydrocarbon group. Here the term "hydrocarbon" means any one of an alkyl group, an alkenyl group, an alkynyl group, which groups may be linear, branched or cyclic, or an aryl group. The term hydrocarbon also includes those groups but wherein they have been optionally substituted. If the hydrocarbon is a branched structure having substituent(s) thereon, then the substitution may be on either the hydrocarbon backbone or on the branch; alternatively the substitutions may be on the hydrocarbon backbone and on the branch.

Oxyhydrocarbyl

The term "oxyhydrocarbyl" group as used herein means a group comprising at least C, H and O and may optionally comprise one or more other suitable substituents. Examples of such substituents may include halo-, alkoxy-, nitro-, an alkyl group, a cyclic group etc. In addition to the possibility of the substituents being a cyclic group, a combination of substituents may form a cyclic group. If the oxyhydrocarbyl group comprises more than one C then those carbons need not necessarily be linked to each other. For example, at least two of the carbons may be linked via a suitable element or group. Thus, the oxyhydrocarbyl group may contain hetero atoms. Suitable hetero atoms will be apparent to those skilled in the art and include, for instance, sulphur and nitrogen.

In one embodiment of the present invention, the oxyhydrocarbyl group is a oxyhydrocarbon group.

Here the term "oxyhydrocarbon" means any one of an alkoxy group, an oxyalkenyl group, an oxyalkynyl group, which groups may be linear, branched or cyclic, or an oxyaryl group. The term oxyhydrocarbon also includes those groups but wherein they have been optionally substituted. If the oxyhydrocarbon is a branched structure having substituent(s) thereon, then the substitution may be on either the hydrocarbon backbone or on the branch; alternatively the substitutions may be on the hydrocarbon backbone and on the branch.

Typically, the oxyhydrocarbyl group is of the formula $C_{1-6}O$ (such as a $C_{1-3}O$).

Assay for Determining Sts Activity Using Cancer Cells (Protocol 1)

Inhibition of Steroid Sulphatase Activity in MCF-7 Cells

Steroid sulphatase activity is measured in vitro using intact MCF-7 human breast cancer cells. This hormone dependent cell line is widely used to study the control of human breast cancer cell growth. It possesses significant steroid sulphatase activity (MacIndoe et al. Endocrinology, 123, 1281-1287 (1988); Purohit & Reed, Int. J. Cancer, 50, 901-905 (1992)) and is available in the U.S.A. from the American Type Culture Collection (ATCC) and in the U.K. (e.g. from The Imperial Cancer Research Fund).

Cells are maintained in Minimal Essential Medium (MEM) (Flow Laboratories, Irvine, Scotland) containing 20 mM HEPES, 5% foetal bovine serum, 2 mM glutamine, non-essential amino acids and 0.075% sodium bicarbonate. Up to 30 replicate 25 cm2 tissue culture flasks are seeded with approximately $1 \times 10^5$ cells/flask using the above medium. Cells are grown to 80% confluency and the medium is changed every third day.

Intact monolayers of MCF-7 cells in triplicate 25 cm² tissue culture flasks are washed with Earle's Balanced Salt Solution (EBSS from ICN Flow, High Wycombe, U.K.) and incubated for 3-4 hours at 37° C. with 5 pmol ($7 \times 10^5$ dpm) [6,7-3H]oestrone-3-sulphate (specific activity 60 Ci/mmol from New England Nuclear, Boston, Mass., U.S.A.) in serum-free MEM (2.5 ml) together with oestrone-3-sulphamate (11 concentrations: 0; 1 fM; 0.01 pM; 0.1 pM; 1 pM; 0.01 nM; 0.1 nM; 1 nM; 0.01 mM; 0.1 mM; 1 mM). After incubation each flask is cooled and the medium (1 ml) is pipetted into separate tubes containing [14C]oestrone ($7 \times 10^3$ dpm) (specific activity 97 Ci/mmol from Amersham International Radiochemical Centre, Amersham, U.K.). The mixture is shaken thoroughly for 30 seconds with toluene (5 ml). Experiments have shown that >90% [14C] oestrone and <0.1% [3H]oestrone-3-sulphate is removed from the aqueous phase by this treatment. A portion (2 ml) of the organic phase is removed, evaporated and the 3H and 14C content of the residue determined by scintillation spectrometry. The mass of oestrone-3-sulphate hydrolysed was calculated from the 3H counts obtained (corrected for the volumes of the medium and organic phase used, and for recovery of [14C] oestrone added) and the specific activity of the substrate. Each batch of experiments includes incubations of microsomes prepared from a sulphatase-positive human placenta (positive control) and flasks without cells (to assess apparent non-enzymatic hydrolysis of the substrate). The number of cell nuclei per flask is determined using a Coulter Counter after treating the cell monolayers with Zaponin. One flask in each batch is used to assess cell membrane status and viability using the Trypan Blue exclusion method (Phillips, H.J. (1973) In: Tissue culture and applications, [eds: Kruse, D. F. & Patterson, M. K.]; pp. 406-408; Academic Press, New York).

Results for steroid sulphatase activity are expressed as the mean ±1 S.D. of the total product (oestrone+oestradiol) formed during the incubation period (20 hours) calculated for 106 cells and, for values showing statistical significance, as a percentage reduction (inhibition) over incubations containing no oestrone-3-sulphamate. Unpaired Student's t-test was used to test the statistical significance of results.

Assay for Determining STS Activity using Placental Microsomes (Protocol 2)

Inhibition of Steroid Sulphatase Activity in Placental Microsomes

Sulphatase-positive human placenta from normal term pregnancies are thoroughly minced with scissors and washed once with cold phosphate buffer (pH 7.4, 50 mM) then re-suspended in cold phosphate buffer (5 ml/g tissue). Homogenisation is accomplished with an Ultra-Turrax homogeniser, using three 10 second bursts separated by 2 minute cooling periods in ice. Nuclei and cell debris are removed by centrifuging (4° C.) at 2000 g for 30 minutes and portions (2 ml) of the supernatant are stored at 20° C. The protein concentration of the supernatants is determined by the method of Bradford (Anal. Biochem., 72, 248-254 (1976)).

Incubations (1 ml) are carried out using a protein concentration of 100 mg/ml, substrate concentration of 20 mM [6,7-3H]oestrone-3-sulphate (specific activity 60 Ci/mmol from New England Nuclear, Boston, Mass., U.S.A.) and an incubation time of 20 minutes at 37° C. If necessary eight concentrations of compounds are employed: 0 (i.e. control); 0.05 mM; 0.1 mM; 0.2 mM; 0.4 mM; 0.6 mM; 0.8 mM; 1.0 mM. After incubation each sample is cooled and the medium (1 ml) was pipetted into separate tubes containing [14C]oestrone ($7 \times 10^3$ dpm) (specific activity 97 Ci/mmol from Amersham International Radiochemical Centre, Amersham, U.K.). The mixture is shaken thoroughly for 30 seconds with toluene (5 ml). Experiments have shown that >90% [14C]oestrone and <0.1% [3H]oestrone-3-sulphate is removed from the aqueous phase by this treatment. A portion (2 ml) of the organic phase was removed, evaporated and the 3H and 14C content of the residue determined by scintillation spectrometry. The mass of oestrone-3-sulphate hydrolysed is calculated from the 3H counts obtained (corrected for the volumes of the medium and organic phase used, and for recovery of [14C]oestrone added) and the specific activity of the substrate.

Animal Assay Model for Determining STS Activity (Protocol 3)

Inhibition of Oestrone Sulphatase Activity in vivo

The compounds of the present invention may be studied using an animal model, in particular in ovariectomised rats. In this model compounds which are oestrogenic stimulate uterine growth.

The compound (10 mg/Kg/day for five days) was administered orally to rats with another group of animals receiving vehicle only (propylene glycol). A further group received the compound EMATE subcutaneously in an amount of 10 μg/day for five days. At the end of the study samples of liver tissue were obtained and oestrone sulphatase activity assayed using 3H oestrone sulphate as the substrate as previously described (see PCT/GB95/02638).

Animal Assay Model for Determining Oestrogenic Activity (Protocol 4)

Lack of in vivo Oestrogenicity

The compounds of the present invention may be studied using an animal model, in particular in ovariectomised rats. In this model, compounds which are oestrogenic stimulate uterine growth.

The compound (10 mg/Kg/day for five days) was administered orally to rats with another group of animals receiving vehicle only (propylene glycol). A further group received the estrogenic compound EMATE subcutaneously in an amount of 10 μg/day for five days. At the end of the study uteri were obtained and weighed with the results being expressed as uterine weight/whole body weight×100.

Compounds having no significant effect on uterine growth are not oestrogenic.

Biotechnological Assays for Determining STS Activity (Protocol 5)

The ability of compounds to inhibit oestrone sulphatase activity can also be assessed using amino acid sequences or nucleotide sequences encoding STS, or active fragments, derivatives, homologues or variants thereof in, for example, high-through put screens.

Any one or more of appropriate targets—such as an amino acid sequence and/or nucleotide sequence—may be used for identifying an agent capable of modulating STS in any of a variety of drug screening techniques. The target employed in such a test may be free in solution, affixed to a solid support, borne on a cell surface, or located intracellularly. The abolition of target activity or the formation of binding complexes between the target and the agent being tested may be measured.

The assay of the present invention may be a screen, whereby a number of agents are tested. In one aspect, the assay method of the present invention is a high through put screen.

Techniques for drug screening may be based on the method described in Geysen, European Patent Application 84/03564, published on Sep. 13, 1984. In summary, large numbers of different small peptide test compounds are synthesised on a solid substrate, such as plastic pins or some other surface. The peptide test compounds are reacted with a suitable target or fragment thereof and washed. Bound entities are then detected—such as by appropriately adapting methods well known in the art. A purified target can also be coated directly onto plates for use in a drug screening techniques. Alternatively, non-neutralising antibodies can be used to capture the peptide and immobilise it on a solid support.

This invention also contemplates the use of competitive drug screening assays in which neutralising antibodies capable of binding a target specifically compete with a test compound for binding to a target.

Another technique for screening provides for high throughput screening (HTS) of agents having suitable binding affinity to the substances and is based upon the method described in detail in WO 84/03564.

It is expected that the assay methods of the present invention will be suitable for both small and large-scale screening of test compounds as well as in quantitative assays.

In one preferred aspect, the present invention relates to a method of identifying agents that selectively modulate STS, which compounds have the formula (Ia).

Reporters

A wide variety of reporters may be used in the assay methods (as well as screens) of the present invention with preferred reporters providing conveniently detectable signals (e.g. by spectroscopy). By way of example, a reporter gene may encode an enzyme which catalyses a reaction which alters light absorption properties.

Other protocols include enzyme-linked immunosorbent assay (ELISA), radioimmunoassay (RIA) and fluorescent activated cell sorting (FACS). A two-site, monoclonal-based immunoassay utilising monoclonal antibodies reactive to two non-interfering epitopes may even be used. These and other assays are described, among other places, in Hampton R et al (1990, Serological Methods, A Laboratory Manual, APS Press, St Paul Minn.) and Maddox D E et al (1983, J Exp Med 15 8:1211).

Examples of reporter molecules include but are not limited to (β-galactosidase, invertase, green fluorescent protein, luciferase, chloramphenicol, acetyltransferase, (-glucuronidase, exo-glucanase and glucoamylase. Alternatively, radiolabelled or fluorescent tag-labelled nucleotides can be incorporated into nascent transcripts which are then identified when bound to oligonucleotide probes.

By way of further examples, a number of companies such as Pharmacia Biotech (Piscataway, N.J.), Promega (Madison, Wis.), and US Biochemical Corp (Cleveland, Ohio) supply commercial kits and protocols for assay procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752 ; 3,939,350; 3,996,345; 4,277,437; 4,275,149 and 4,366,241.

Host Cells

The term "host cell"—in relation to the present invention includes any cell that could comprise the target for the agent of the present invention.

Thus, a further embodiment of the present invention provides host cells transformed or transfected with a polynucleotide that is or expresses the target of the present invention. Preferably said polynucleotide is carried in a vector for the replication and expression of polynucleotides that are to be the target or are to express the target. The cells will be chosen to be compatible with the said vector and may for example be prokaryotic (for example bacterial), fungal, yeast or plant cells.

The gram negative bacterium *E. coli* is widely used as a host for heterologous gene expression. However, large amounts of heterologous protein tend to accumulate inside the cell. Subsequent purification of the desired protein from the bulk of *E. coli* intracellular proteins can sometimes be difficult.

In contrast to *E. coli*, bacteria from the genus *Bacillus* are very suitable as heterologous hosts because of their capability to secrete proteins into the culture medium. Other bacteria suitable as hosts are those from the genera *Streptomyces* and *Pseudomonas*.

Depending on the nature of the polynucleotide encoding the polypeptide of the present invention, and/or the desirability for further processing of the expressed protein, eukaryotic hosts such as yeasts or other fungi may be preferred. In general, yeast cells are preferred over fungal cells because they are easier to manipulate. However, some proteins are either poorly secreted from the yeast cell, or in some cases are not processed properly (e.g. hyperglycosylation in yeast). In these instances, a different fungal host organism should be selected.

Examples of suitable expression hosts within the scope of the present invention are fungi such as *Aspergillus* species (such as those described in EP-A-0184438 and EP-A-0284603) and *Trichoderma* species; bacteria such as *Bacillus* species (such as those described in EP-A-0134048 and EP-A-0253455), *Streptomyces* species and *Pseudomonas* species; and yeasts such as *Kluyveromyces* species (such as those described in EP-A-0096430 and EP-A-0301670) and *Saccharomyces* species. By way of example, typical expression hosts may be selected from *Aspergillus niger, Aspergillus niger* var. *tubigenis, Aspergillus niger* var. *awamori, Aspergillus aculeatis, Aspergillus nidulans, Aspergillus oryzae, Trichoderma reesei, Bacillus subtilis, Bacillus licheniformis, Bacillus amyloliquefaciens, Kluyveromyces lactis* and *Saccharomyces cerevisiae*.

The use of suitable host cells—such as yeast, fungal and plant host cells—may provide for post-translational modifications (e.g. myristoylation, glycosylation, truncation, lapidation and tyrosine, serine or threonine phosphorylation) as may be needed to confer optimal biological activity on recombinant expression products of the present invention.

Organism

The term "organism" in relation to the present invention includes any organism that could comprise the target according to the present invention and/or products obtained therefrom. Examples of organisms may include a fungus, yeast or a plant.

The term "transgenic organism" in relation to the present invention includes any organism that comprises the target according to the present invention and/or products obtained.

Transformation of Host Cells/Host Organisms

As indicated earlier, the host organism can be a prokaryotic or a eukaryotic organism. Examples of suitable prokaryotic hosts include *E. coli* and *Bacillus subtilis*. Teachings on the transformation of prokaryotic hosts is well documented in the art, for example see Sambrook et al (Molecular Cloning: A Laboratory Manual, 2nd edition, 1989, Cold Spring Harbor Laboratory Press) and Ausubel et al., Current Protocols in Molecular Biology (1995), John Wiley & Sons, Inc.

If a prokaryotic host is used then the nucleotide sequence may need to be suitably modified before transformation—such as by removal of introns.

In another embodiment the transgenic organism can be a yeast. In this regard, yeast have also been widely used as a vehicle for heterologous gene expression. The species *Saccharomyces cerevisiae* has a long history of industrial use, including its use for heterologous gene expression. Expression of heterologous genes in *Saccharomyces cerevisiae* has been reviewed by Goodey et al (1987, Yeast Biotechnology, D R Berry et al, eds, pp 401-429, Allen and Unwin, London) and by King et al (1989, Molecular and Cell Biology of Yeasts, E F Walton and G T Yarronton, eds, pp 107-133, Blackie, Glasgow).

For several reasons *Saccharomyces cerevisiae* is well suited for heterologous gene expression. First, it is non-pathogenic to humans and it is incapable of producing certain endotoxins. Second, it has a long history of safe use following centuries of commercial exploitation for various purposes. This has led to wide public acceptability. Third, the extensive commercial use and research devoted to the organism has resulted in a wealth of knowledge about the genetics and physiology as well as large-scale fermentation characteristics of *Saccharomyces cerevisiae*.

A review of the principles of heterologous gene expression in *Saccharomyces cerevisiae* and secretion of gene products is given by E Hinchcliffe E Kenny (1993, "Yeast as a vehicle for the expression of heterologous genes", Yeasts, Vol 5, Anthony H Rose and J Stuart Harrison, eds, 2nd edition, Academic Press Ltd.).

Several types of yeast vectors are available, including integrative vectors, which require recombination with the host genome for their maintenance, and autonomously replicating plasmid vectors.

In order to prepare the transgenic *Saccharomyces*, expression constructs are prepared by inserting the nucleotide sequence into a construct designed for expression in yeast. Several types of constructs used for heterologous expression have been developed. The constructs contain a promoter active in yeast fused to the nucleotide sequence, usually a promoter of yeast origin, such as the GAL1 promoter, is used. Usually a signal sequence of yeast origin, such as the sequence encoding the SUC2 signal peptide, is used. A terminator active in yeast ends the expression system.

For the transformation of yeast several transformation protocols have been developed. For example, a transgenic *Saccharomyces* according to the present invention can be prepared by following the teachings of Hinnen et al (1978, Proceedings of the National Academy of Sciences of the USA 75, 1929); Beggs, J D (1978, Nature, London, 275, 104); and Ito, H et al (1983, J Bacteriology 153, 163-168).

The transformed yeast cells are selected using various selective markers. Among the markers used for transformation are a number of auxotrophic markers such as LEU2, HIS4 and TRP1, and dominant antibiotic resistance markers such as aminoglycoside antibiotic markers, e.g. G418.

Another host organism is a plant. The basic principle in the construction of genetically modified plants is to insert genetic information in the plant genome so as to obtain a stable maintenance of the inserted genetic material. Several techniques exist for inserting the genetic information, the two main principles being direct introduction of the genetic information and introduction of the genetic information by use of a vector system. A review of the general techniques may be found in articles by Potrykus (Annu Rev Plant Physiol Plant Mol Biol [1991] 42:205-225) and Christou (Agro-Food-Industry Hi-Tech March/April 1994 17-27). Further teachings on plant transformation may be found in EP-A-0449375.

Thus, the present invention also provides a method of transforming a host cell with a nucleotide sequence that is to be the target or is to express the target. Host cells transformed with the nucleotide sequence may be cultured under conditions suitable for the expression of the encoded protein. The protein produced by a recombinant cell may be displayed on the surface of the cell. If desired, and as will be understood by those of skill in the art, expression vectors containing coding sequences can be designed with signal sequences which direct secretion of the coding sequences through a particular prokaryotic or eukaryotic cell membrane. Other recombinant constructions may join the coding sequence to nucleotide sequence encoding a polypeptide domain which will facilitate purification of soluble proteins (Kroll D J et al (1993) DNA Cell Biol 12:441-53).

Variants/Homologues/Derivatives

In addition to the specific amino acid sequences and nucleotide sequences mentioned herein, the present invention also encompasses the use of variants, homologue and derivatives thereof. Here, the term "homology" can be equated with "identity".

In the present context, an homologous sequence is taken to include an amino acid sequence which may be at least 75, 85 or 90% identical, preferably at least 95 or 98% identical. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package (see below) the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program.

A further useful reference is that found in FEMS Microbiol Lett 1999 May 15; 174(2):247-50 (and a published erratum appears in FEMS Microbiol Lett 1999 Aug. 1; 177(1):187-8).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). It is preferred to use the public default values for the GCG package, or in the case of other software, the default matrix, such as BLOSUM62.

Once the software has produced an optimal alignment, it is possible to calculate % homology, preferably % sequence identity. The software typically does this as part of the sequence comparison and generates a numerical result.

The sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

Expression Vectors

The nucleotide sequence for use as the target or for expressing the target can be incorporated into a recombinant replicable vector. The vector may be used to replicate and express the nucleotide sequence in and/or from a compatible host cell. Expression may be controlled using control sequences which include promoters/enhancers and other expression regulation signals. Prokaryotic promoters and promoters functional in eukaryotic cells may be used. Tissue specific or stimuli specific promoters may be used. Chimeric promoters may also be used comprising sequence elements from two or more different promoters described above.

The protein produced by a host recombinant cell by expression of the nucleotide sequence may be secreted or may be contained intracellularly depending on the sequence and/or the vector used. The coding sequences can be designed with signal sequences which direct secretion of the substance coding sequences through a particular prokaryotic or eukaryotic cell membrane.

Fusion Proteins

The target amino acid sequence may be produced as a fusion protein, for example to aid in extraction and purification. Examples of fusion protein partners include glutathione-S-transferase (GST), 6×His, GAL4 (DNA binding and/or transcriptional activation domains) and (-galactosidase. It may also be convenient to include a proteolytic cleavage site between the fusion protein partner and the protein sequence of interest to allow removal of fusion protein sequences. Preferably the fusion protein will not hinder the activity of the target.

The fusion protein may comprise an antigen or an antigenic determinant fused to the substance of the present invention. In this embodiment, the fusion protein may be a non-naturally occurring fusion protein comprising a substance which may act as an adjuvant in the sense of providing a generalised stimulation of the immune system. The antigen or antigenic determinant may be attached to either the amino or carboxy terminus of the substance.

In another embodiment of the invention, the amino acid sequence may be ligated to a heterologous sequence to encode a fusion protein. For example, for screening of peptide libraries for agents capable of affecting the substance activity, it may be useful to encode a chimeric substance expressing a heterologous epitope that is recognised by a commercially available antibody.

Therapy

The compounds of the present invention may be used as therapeutic agents—i.e. in therapy applications.

The term "therapy" includes curative effects, alleviation effects, and prophylactic effects.

The therapy may be on humans or animals, preferably female animals.

Pharmaceutical Compositions

In one aspect, the present invention provides a pharmaceutical composition, which comprises a compound according to the present invention and optionally a pharmaceutically acceptable carrier, diluent or excipient (including combinations thereof).

The pharmaceutical compositions may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Preservatives, stabilisers, dyes and even flavouring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition of the present invention may be formulated to be delivered using a mini-pump or by a mucosal route, for example, as a nasal spray or aerosol for inhalation or ingestable solution, or parenterally in which the composition is formulated by an injectable form, for delivery, by, for example, an intravenous, intramuscular or subcutaneous route. Alternatively, the formulation may be designed to be delivered by both routes.

Where the agent is to be delivered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

Combination Pharmaceutical

The compound of the present invention may be used in combination with one or more other active agents, such as one or more other pharmaceutically active agents.

By way of example, the compounds of the present invention may be used in combination with other STS inhibitors and/or other inhibitors such as an aromatase inhibitor (such as for example, 4hydroxyandrostenedione (4-OHA)) and/or steroids—such as the naturally occurring sterneurosteroids dehydroepiandrosterone sulfate (DHEAS) and pregnenolone sulfate (PS) and/or other structurally similar organic compounds. Examples of other STS inhibitors may be found in the above references. By way of example, STS inhibitors for use in the present invention include EMATE, and either or both of the 2-ethyl and 2-methoxy 17-deoxy compounds that are analogous to compound 5 presented herein.

In addition, or in the alternative, the compound of the present invention may be used in combination with a biological response modifier.

The term biological response modifier ("BRM") includes cytokines, immune modulators, growth factors, haematopoiesis regulating factors, colony stimulating factors, chemotactic, haemolytic and thrombolytic factors, cell surface receptors, ligands, leukocyte adhesion molecules, monoclonal antibodies, preventative and therapeutic vaccines, hormones, extracellular matrix components, fibronectin, etc. For some applications, preferably, the biological response modifier is a cytokine. Examples of cytokines include: interleukins (IL)—such as IL-1, IL-2, IL-3, IL-4, IL-5, IL-6, IL-7, IL-8, IL-9, IL-10, IL-11, IL-12, IL-19; Tumour Necrosis Factor (TNF)—such as TNF-$\alpha$; Interferon alpha, beta and gamma; TGF-$\beta$. For some applications, preferably the cytokine is tumour necrosis factor (TNF). For some applications, the TNF may be any type of TNF—such as TNF-$\alpha$, TNF-$\beta$, including derivatives or mixtures thereof. More preferably the cytokine is TNF-$\alpha$. Teachings on TNF may be found in the art—such as WO-A-98/08870 and WO-A-98/13348.

Administration

Typically, a physician will determine the actual dosage which will be most suitable for an individual subject and it will vary with the age, weight and response of the particular patient. The dosages below are exemplary of the average case. There can, of course, be individual instances where higher or lower dosage ranges are merited.

The compositions of the present invention may be administered by direct injection. The composition may be formulated for parenteral, mucosal, intramuscular, intravenous, subcutaneous, intraocular or transdermal administration. Depending upon the need, the agent may be administered at a dose of from 0.01 to 30 mg/kg body weight, such as from 0.1 to 10 mg/kg, more preferably from 0.1 to 1 mg/kg body weight.

By way of further example, the agents of the present invention may be administered in accordance with a regimen of 1 to 4 times per day, preferably once or twice per day. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Aside from the typical modes of delivery—indicated above—the term "administered" also includes delivery by techniques such as lipid mediated transfection, liposomes, immunoliposomes, lipofectin, cationic facial amphiphiles (CFAs) and combinations thereof. The routes for such delivery mechanisms include but are not limited to mucosal, nasal, oral, parenteral, gastrointestinal, topical, or sublingual routes.

The term "administered" includes but is not limited to delivery by a mucosal route, for example, as a nasal spray or aerosol for inhalation or as an ingestable solution; a parenteral route where delivery is by an injectable form, such as, for example, an intravenous, intramuscular or subcutaneous route.

Thus, for pharmaceutical administration, the STS inhibitors of the present invention can be formulated in any suitable manner utilising conventional pharmaceutical formulating techniques and pharmaceutical carriers, adjuvants, excipients, diluents etc. and usually for parenteral administration. Approximate effective dose rates may be in the range from 1 to 1000 mg/day, such as from 10 to 900 mg/day or even from 100 to 800 mg/day depending on the individual activities of the compounds in question and for a patient of average (70 Kg) bodyweight. More usual dosage rates for the preferred and more active compounds will be in the range 200 to 800 mg/day, more preferably, 200 to 500 mg/day, most preferably from 200 to 250 mg/day. They may be given in single dose regimes, split dose regimes and/or in multiple dose regimes lasting over several days. For oral administration they may be formulated in tablets, capsules, solution or suspension containing from 100 to 500 mg of compound per unit dose. Alternatively and preferably the compounds will be formulated for parenteral administration in a suitable parenterally administrable carrier and providing single daily dosage rates in the range 200 to 800 mg, preferably 200 to 500, more preferably 200 to 250 mg. Such effective daily doses will, however, vary depending on inherent activity of the active ingredient and on the bodyweight of the patient, such variations being within the skill and judgement of the physician.

Cell Cycling

The compounds of the present invention may be useful in the method of treatment of a cell cycling disorder.

As discussed in "Molecular Cell Biology" 3rd Ed. Lodish et al. pages 177-181 different eukaryotic cells can grow and divide at quite different rates. Yeast cells, for example, can divide every 120 min., and the first divisions of fertilised eggs in the embryonic cells of sea urchins and insects take only 1530 min. because one large pre-existing cell is subdivided. However, most growing plant and animal cells take 10-20 hours to double in number, and some duplicate at a much slower rate. Many cells in adults, such as nerve cells and striated muscle cells, do not divide at all; others, like the fibroblasts that assist in healing wounds, grow on demand but are otherwise quiescent.

Still, every eukaryotic cell that divides must be ready to donate equal genetic material to two daughter cells. DNA synthesis in eukaryotes does not occur throughout the cell division cycle but is restricted to a part of it before cell division.

The relationship between eukaryotic DNA synthesis and cell division has been thoroughly analysed in cultures of mammalian cells that were all capable of growth and division. In contrast to bacteria, it was found, eukaryotic cells spend only a part of their time in DNA synthesis, and it is completed hours before cell division (mitosis). Thus a gap of time occurs after DNA synthesis and before cell division; another gap was found to occur after division and before the next round of DNA synthesis. This analysis led to the conclusion that the eukaryotic cell cycle consists of an M (mitotic) phase, a $G_1$ phase (the first gap), the S (DNA synthesis) phase, a $G_2$ phase (the second gap), and back to M. The phases between mitoses ($G_1$, S, and $G_2$) are known collectively as the interphase.

Many nondividing cells in tissues (for example, all quiescent fibroblasts) suspend the cycle after mitosis and just prior to DNA synthesis; such "resting" cells are said to have exited from the cell cycle and to be in the $G_0$ state.

It is possible to identify cells when they are in one of the three interphase stages of the cell cycle, by using a fluorescence-activated cell sorter (FACS) to measure their relative DNA content: a cell that is in $G_1$ (before DNA synthesis) has a defined amount x of DNA; during S (DNA replication), it has between x and 2x; and when in $G_2$ (or M), it has 2x of DNA.

The Stages of Mitosis and Cytokinesis in an Animal Cell are as Follows (a) Interphase. The $G_2$ stage of interphase immediately precedes the beginning of mitosis. Chromosomal DNA has been replicated and bound to protein during the S phase, but chromosomes are not yet seen as distinct structures. The nucleolus is the only nuclear substructure that is visible under light microscope. In a diploid cell before DNA replication there are two morphologic chromosomes of each type, and the cell is said to be 2n. In $G_2$, after DNA replication, the cell is 4n. There are four copies of each chromosomal DNA. Since the sister chromosomes have not yet separated from each other, they are called sister chromatids.

b) Early prophase. Centrioles, each with a newly formed daughter centriole, begin moving toward opposite poles of the cell; the chromosomes can be seen as long threads. The nuclear membrane begins to disaggregate into small vesicles.

(c) Middle and late prophase. Chromosome condensation is completed; each visible chromosome structure is composed of two chromatids held together at their centromeres. Each chromatid contains one of the two newly replicated daughter DNA molecules. The microtubular spindle begins to radiate from the regions just adjacent to the centrioles, which are moving closer to their poles. Some spindle fibres reach from pole to pole; most go to chromatids and attach at kinetochores.

(d) Metaphase. The chromosomes move toward the equator of the cell, where they become aligned in the equatorial plane. The sister chromatids have not yet separated.

(e) Anaphase. The two sister chromatids separate into independent chromosomes. Each contains a centromere that is linked by a spindle fibre to one pole, to which it moves. Thus one copy of each chromosome is donated to each daughter cell. Simultaneously, the cell elongates, as do the pole-to-pole spindles. Cytokinesis begins as the cleavage furrow starts to form.

(f) Telophase. New membranes form around the daughter nuclei; the chromosomes uncoil and become less distinct, the nucleolus becomes visible again, and the nuclear membrane forms around each daughter nucleus. Cytokinesis is nearly complete, and the spindle disappears as the microtubules and other fibres depolymerise. Throughout mitosis the "daughter" centriole at each pole grows until it is full-length. At telophase the duplication of each of the original centrioles is completed, and new daughter centrioles will be generated during the next interphase.

(g) Interphase. Upon the completion of cytokinesis, the cell enters the $G_1$ phase of the cell cycle and proceeds again around the cycle.

It will be appreciated that cell cycling is an extremely important cell process. Deviations from normal cell cycling can result in a number of medical disorders. Increased and/or unrestricted cell cycling may result in cancer. Reduced cell cycling may result in degenerative conditions. Use of the compound of the present invention may provide a means to treat such disorders and conditions.

Thus, the compound of the present invention may be suitable for use in the treatment of cell cycling disorders such as cancers, including hormone dependent and hormone independent cancers.

In addition, the compound of the present invention may be suitable for the treatment of cancers such as breast cancer, ovarian cancer, endometrial cancer, sarcomas, melanomas, prostate cancer, pancreatic cancer etc. and other solid tumours.

For some applications, cell cycling is inhibited and/or prevented and/or arrested, preferably wherein cell cycling is prevented and/or arrested. In one aspect cell cycling may be inhibited and/or prevented and/or arrested in the $G_2/M$ phase. In one aspect cell cycling may be irreversibly prevented and/or inhibited and/or arrested, preferably wherein cell cycling is irreversibly prevented and/or arrested.

By the term "irreversibly prevented and/or inhibited and/or arrested" it is meant after application of a compound of the present invention, on removal of the compound the effects of the compound, namely prevention and/or inhibition and/or arrest of cell cycling, are still observable. More particularly by the term "irreversibly prevented and/or inhibited and/or arrested" it is meant that when assayed in accordance with the cell cycling assay protocol presented herein, cells treated with a compound of interest show less growth after Stage 2 of the protocol I than control cells. Details on this protocol are presented below.

Thus, the present invention provides compounds which: cause inhibition of growth of oestrogen receptor positive (ER+) and ER negative (ER−) breast cancer cells in vitro by preventing and/or inhibiting and/or arresting cell cycling; and/or cause regression of nitroso-methyl urea (NMU)-induced mammary tumours in intact animals (i.e. not ovariectomised), and/or prevent and/or inhibit and/or arrest cell cycling in cancer cells; and/or act in vivo by preventing and/or inhibiting and/or arresting cell cycling and/or act as a cell cycling agonist.

Cell Cycling Assay

Protocol 6

Procedure
Stage 1
MCF-7 breast cancer cells are seeded into multi-well culture plates at a density of 105 cells/well. Cells were allowed to attach and grown until about 30% confluent when they are treated as follows:
Control—no treatment
Compound of Interest (COI) 20 µM
Cells are grown for 6 days in growth medium containing the COI with changes of medium/COI every 3 days. At the end of this period cell numbers were counted using a Coulter cell counter.
Stage 2
After treatment of cells for a 6-day period with the COI cells are re-seeded at a density of $10^4$ cells/well. No further treatments are added. Cells are allowed to continue to grow for a further 6 days in the presence of growth medium. At the end of this period cell numbers are again counted.

Assay for Determining DH Activity using Cancer Cells (Protocol 7)

Conversion of oestrone to oestradiol (E1→E2, E2DH Type I) and oestradiol to oestrone (E2→E1, E2DH Type II) was measured in intact cell monolayers of T47D and MDA-MB-231 breast cancer cells respectively. Cells were cultured in flasks until they were 80-90% confluent. $^3$H-E1 or $^3$H-E2 (6 pmol, ~90 Ci/mmol) were added to each flask in the absence (control) or presence of various test compounds (10 µM) in 2.5 ml of medium. Substrate was also added to flasks without cells and incubated in parallel (blanks).

After incubation with T47D cells for 30 min or MDA cells for 3 h at 37° C., 2 ml of the medium was added to test tubes containing $^{14}$C-E2 or $^{14}$C-E1 (~5000 cpm) and 50 µg E2 or E1 respectively. Steroids were extracted from the aqueous medium with diethyl ether (4 ml). The ether phase was decanted into separate tubes after freezing the aqueous phase in solid carbon dioxide-methanol mixture. The ether was evaporated to dryness under a stream of air at 40° C. The residue was dissolved in a small volume of diethyl ether and applied to TLC plates containing a fluorescent indicator. E1 and E2 were separated by TLC using DCM-Ethyl acetate (4:1 v/v). The position of the product from each incubation flask was marked on the TLC plate after visualisation under UV light. The marked regions were cut out and placed in scintillation vials containing methanol (0.5 ml) to elute the product. The amount of $^3$H-product formed and $^{14}$C-E1 or $^{14}$C-E2 recovered were calculated after scintillation spectrometry. The amount of product formed was corrected for procedural losses and for the number of cells in each flask.

Cancer

As indicated, the compounds of the present invention may be useful in the treatment of a cell cycling disorder. A particular cell cycling disorder is cancer.

Cancer remains a major cause of mortality in most Western countries. Cancer therapies developed so far have included blocking the action or synthesis of hormones to inhibit the growth of hormone-dependent tumours. However, more aggressive chemotherapy is currently employed for the treatment of hormone-independent tumours.

Hence, the development of a pharmaceutical for anti-cancer treatment of hormone dependent and/or hormone independent tumours, yet lacking some or all of the side-effects associated with chemotherapy, would represent a major therapeutic advance.

It is known that oestrogens undergo a number of hydroxylation and conjugation reactions after their synthesis. Until recently it was thought that such reactions were part of a metabolic process that ultimately rendered oestrogens water soluble and enhanced their elimination from the body. It is now evident that some hydroxy metabolites (e.g. 2-hydroxy and 16alpha-hydroxy) and conjugates (e.g. oestrone sulphate, E1S) are important in determining some of the complex actions that oestrogens have in the body.

Workers have investigated the formation of 2- and 16-hydroxylated oestrogens in relation to conditions that alter the risk of breast cancer. There is now evidence that factors which increase 2-hydroxylase activity are associated with a reduced cancer risk, while those increasing 16alpha-hydroxylation may enhance the risk of breast cancer. Further interest in the biological role of oestrogen metabolites has been stimulated by the growing body of evidence that 2-methoxyoestradiol is an endogenous metabolite with anti-mitotic properties. 2-MeOE2 is formed from 2-hydroxy oestradiol (2-OHE2) by catechol oestrogen methyl transferase, an enzyme that is widely distributed throughout the body.

Workers have shown that in vivo 2-MeOE2 inhibits the growth of tumours arising from the subcutaneous injection of Meth A sarcoma, B16 melanoma or MDA-MB-435 oestrogen receptor negative (ER−) breast cancer cells. It also inhibits endothelial cell proliferation and migration, and in vitro angiogenesis. It was suggested that the ability of 2-MeOE2 to inhibit tumour growth in vivo may be due to its ability to inhibit tumour-induced angiogenesis rather than direct inhibition of the proliferation of tumour cells.

The mechanism by which 2-MeOE2 exerts its potent anti-mitogenic and anti-angiogenic effects is still being elucidated. There is evidence that at high concentrations it can inhibit microtubule polymerisation and act as a weak inhibitor of colchicine binding to tubulin. Recently, however, at concentrations that block mitosis, tubulin filaments in cells were not found to be depolymerised but to have an identical morphology to that seen after taxol treatment. It is possible, therefore, that like taxol, a drug that is used for breast and ovarian breast cancer therapy, 2-MeOE2 acts by stabilising microtubule dynamics.

While the identification of 2-MeOE2 as a new therapy for cancer represents an important advance, the bioavailability of orally administered oestrogens is poor. Furthermore, they can undergo extensive metabolism during their first pass through the liver. As part of a research programme to develop a steroid sulphatase inhibitor for breast cancer therapy, oestrone-3-O-sulphamate (EMATE) was identified as a potent active site-directed inhibitor. Unexpectedly, EMATE proved to possess potent oestrogenic properties with its oral uterotrophic activity in rats being a 100-times higher than that of oestradiol. Its enhanced oestrogenicity is thought to result from its absorption by red blood cells (rbcs) which protects it from inactivation during its passage through the liver and which act as a reservoir for its slow release for a prolonged period of time. A number of A-ring modified analogues were synthesised and tested, including 2-methoxyoestrone-3-O-sulphamate. While this compound was equipotent with EMATE as a steroid sulphatase inhibitor, it was devoid of oestrogenicity.

We believe that the compound of the present invention provides a means for the treatment of cancers and, especially, breast cancer.

In addition or in the alternative the compound of the present invention may be useful in the blocking the growth of cancers including leukaemias and solid tumours such as breast, endometrium, prostate, ovary and pancreatic tumours.

Therapy Concerning Oestrogen

We believe that some of the compounds of the present invention may be useful in the control of oestrogen levels in the body—in particular in females. Thus, some of the compounds may be useful as providing a means of fertility control—such as an oral contraceptive tablet, pill, solution or lozenge. Alternatively, the compound could be in the form of an implant or as a patch.

Thus, the compounds of the present invention may be useful in treating hormonal conditions associated with oestrogen.

In addition or in the alternative the compound of the present invention may be useful in treating hormonal conditions in addition to those associated with oestrogen. Hence, the compound of the present invention may also be capable of affecting hormonal activity and may also be capable of affecting an immune response.

Neurodegenerative Diseases

We believe that some of the compounds of the present invention may be useful in the treatment of neurodenerative diseases, and similar conditions.

By way of example, it is believed that STS inhibitors may be useful in the enhancing the memory function of patients suffering from illnesses such as amnesia, head injuries, Alzheimer's disease, epileptic dementia, presenile dementia, post traumatic dementia, senile dementia, vascular dementia and post-stroke dementia or individuals otherwise seeking memory enhancement.

TH1

We believe that some of the compounds of the present invention may be useful in TH1 implications.

By way of example, it is believed that the presence of STS inhibitors within the macrophage or other antigen presenting cells may lead to a decreased ability of sensitised T cells to mount a TH1 (high IL-2, IFNγ low IL-4) response. The normal regulatory influence of other steroids such as glucocorticoids would therefore predominate.

Inflamatory Conditions

We believe that some of the compounds of the present invention may be useful in treating inflammatory conditions—such as conditions associated with any one or more of: autoimmunity, including for example, rheumatoid arthritis, type I and II diabetes, systemic lupus erythematosus, multiple sclerosis, myasthenia gravis, thyroiditis, vasculitis, ulcerative colitis and Crohn's disease, skin disorders e.g. psoriasis and contact dermatitis; graft versus host disease; eczema; asthma and organ rejection following transplantation.

By way of example, it is believed that STS inhibitors may prevent the normal physiological effect of DHEA or related steroids on immune and/or inflammatory responses.

The compounds of the present invention may be useful in the manufacture of a medicament for revealing an endogenous glucocorticoid-like effect.

Other Therapies

It is also to be understood that the compound/composition of the present invention may have other important medical implications.

For example, the compound or composition of the present invention may be useful in the treatment of the disorders listed in WO-A-99/52890-viz:

In addition, or in the alternative, the compound or composition of the present invention may be useful in the treatment of the disorders listed in WO-A-98/05635. For ease of reference, part of that list is now provided: cancer, inflammation or inflammatory disease, dermatological disorders, fever, cardiovascular effects, haemorrhage, coagulation and acute phase response, cachexia, anorexia, acute infection, HIV infection, shock states, graft-versus-host reactions, autoimmune disease, reperfusion injury, meningitis, migraine and aspirin-dependent anti-thrombosis; tumour growth, invasion and spread, angiogenesis, metastases, malignant, ascites and malignant pleural effusion; cerebral ischaemia, ischaemic heart disease, osteoarthritis, rheumatoid arthritis, osteoporosis, asthma, multiple sclerosis, neurodegeneration, Alzheimer's disease, atherosclerosis, stroke, vasculitis, Crohn's disease and ulcerative colitis; periodontitis, gingivitis; psoriasis, atopic dermatitis, chronic ulcers, epidermolysis bullosa; corneal ulceration, retinopathy and surgical wound healing; rhinitis, allergic conjunctivitis, eczema, anaphylaxis; restenosis, congestive heart failure, endometriosis, atherosclerosis or endosclerosis.

In addition, or in the alternative, the compound or composition of the present invention may be useful in the treatment of disorders listed in WO-A-98/07859. For ease of reference, part of that list is now provided: cytokine and cell proliferation/differentiation activity; immunosuppressant or immunostimulant activity (e.g. for treating immune deficiency, including infection with human immune deficiency virus; regulation of lymphocyte growth; treating cancer and many autoimmune diseases, and to prevent transplant rejection or induce tumour immunity); regulation of haematopoiesis, e.g. treatment of myeloid or lymphoid diseases; promoting growth of bone, cartilage, tendon, ligament and nerve tissue, e.g. for healing wounds, treatment of burns, ulcers and periodontal disease and neurodegeneration; inhibition or activation of follicle-stimulating hormone (modulation of fertility); chemotactic/chemokinetic activity (e.g. for mobilising specific cell types to sites of injury or infection); haemostatic and thrombolytic activity (e.g. for treating haemophilia and stroke); antiinflammatory activity (for treating e.g. septic shock or Crohn's disease); as antimicrobials; modulators of e.g. metabolism or behaviour; as analgesics; treating specific deficiency disorders; in treatment of e.g. psoriasis, in human or veterinary medicine.

In addition, or in the alternative, the composition of the present invention may be useful in the treatment of disorders listed in WO-A-98/09985. For ease of reference, part of that list is now provided: macrophage inhibitory and/or T cell inhibitory activity and thus, anti-inflammatory activity; anti-immune activity, i.e. inhibitory effects against a cellular and/or humoral immune response, including a response not associated with inflammation; inhibit the ability of macrophages and T cells to adhere to extracellular matrix components and fibronectin, as well as up-regulated fas receptor expression in T cells; inhibit unwanted immune reaction and inflammation including arthritis, including rheumatoid arthritis, inflammation associated with hypersensitivity, allergic reactions, asthma, systemic lupus erythematosus, collagen diseases and other autoimmune diseases, inflammation associated with atherosclerosis, arteriosclerosis, atherosclerotic heart disease, reperfusion injury, cardiac arrest, myocardial infarction, vascular inflammatory disorders, respiratory distress syndrome or other cardiopulmonary diseases, inflammation associated with peptic ulcer, ulcerative colitis and other diseases of the gastrointestinal tract, hepatic fibrosis, liver cirrhosis or other hepatic diseases, thyroiditis or other glandular diseases, glomerulonephritis or other renal and urologic diseases, otitis or other oto-rhino-laryngological diseases, dermatitis or other dermal diseases, periodontal diseases or other dental diseases, orchitis or epididimo-orchitis, infertility, orchidal trauma or other immune-related testicular diseases, placental dysfunction, placental insufficiency, habitual abortion, eclampsia, pre-eclampsia and other immune and/or inflammatory-related gynaecological diseases, posterior uveitis, intermediate uveitis, anterior uveitis, conjunctivitis, chorioretinitis, uveoretinitis, optic neuritis, intraocular inflammation, e.g. retinitis or cystoid macular oedema, sympathetic ophthalmia, scleritis, retinitis pigmentosa, immune and inflammatory components of degenerative fondus disease, inflammatory components of ocular trauma, ocular inflammation caused by infection, proliferative vitreo-retinopathies, acute ischaemic optic neuropathy, excessive scarring, e.g. following glaucoma filtration operation, immune and/or inflammation reaction against ocular implants and other immune and inflammatory-related ophthalmic diseases, inflammation associated with autoimmune diseases or conditions or disorders where, both in the central nervous system (CNS) or in any other organ, immune and/or inflammation suppression would be beneficial, Parkinson's disease, complication and/or side effects from treatment of Parkinson's disease, AIDS-related dementia complex HIV-related encephalopathy, Devic's disease, Sydenham chorea, Alzheimer's disease and other degenerative diseases, conditions or disorders of the CNS, inflammatory components of stokes, post-polio syndrome, immune and inflammatory components of psychiatric disorders, myelitis, encephalitis, subacute sclerosing pan-encephalitis, encephalomyelitis, acute neuropathy, subacute neuropathy, chronic neuropathy, Guillaim-Barre syndrome, Sydenham chora, myasthenia gravis, pseudo-tumour cerebri, Down's Syndrome, Huntington's disease, amyotrophic lateral sclerosis, inflammatory components of CNS compression or CNS trauma or infections of the CNS, inflammatory components of muscular atrophies and dystrophies, and immune and inflammatory related diseases, conditions or disorders of the central and peripheral nervous systems, post-traumatic inflammation, septic shock, infectious diseases, inflammatory complications or side effects of surgery, bone marrow transplantation or other transplantation complications and/or side effects, inflammatory and/or immune complications and side effects of gene therapy, e.g. due to infection with a viral carrier, or inflammation associated with AIDS, to suppress or inhibit a humoral and/or cellular immune response, to treat or ameliorate monocyte or leukocyte proliferative diseases, e.g. leukaemia, by reducing the amount of monocytes or lymphocytes, for the prevention and/or treatment of graft rejection in cases of transplantation of natural or artificial cells, tissue and organs such as cornea, bone marrow, organs, lenses, pacemakers, natural or artificial skin tissue.

Sulphamate Compound Preparation

The sulphamate compounds of the present invention may be prepared by reacting an appropriate alcohol with a suitable chloride. By way of example, the sulphamate compounds of the present invention may be prepared by reacting an appropriate alcohol with a suitable sulfamoyl chloride, of the formula $R^4R^5NSO_2Cl$.

Typical conditions for carrying out the reaction are as follows.

Sodium hydride and a sulfamoyl chloride are added to a stirred solution of the alcohol in anhydrous dimethyl formamide at 0° C. Subsequently, the reaction is allowed to warm to room temperature whereupon stirring is continued for a further 24 hours. The reaction mixture is poured onto a cold saturated solution of sodium bicarbonate and the resulting aqueous phase is extracted with dichloromethane. The combined organic extracts are dried over anhydrous $MgSO_4$. Filtration followed by solvent evaporation in vacuo and co-evaporated with toluene affords a crude residue which is further purified by flash chromatography.

Preferably, the alcohol is derivatised, as appropriate, prior to reaction with the sulfamoyl chloride. Where necessary, functional groups in the alcohol may be protected in known manner and the protecting group or groups removed at the end of the reaction.

Preferably, the sulphamate compounds are prepared according to the teachings of Page et al (1990 Tetrahedron 46; 2059-2068).

The phosphonate compounds may be prepared by suitably combining the teachings of Page et al (1990 Tetrahedron 46; 2059-2068) and PCT/GB92/01586.

The sulphonate compounds may be prepared by suitably adapting the teachings of Page et al (1990 Tetrahedron 46; 2059-2068) and PCT/GB92/01586.

The thiophosphonate compounds may be prepared by suitably adapting the teachings of Page et al (1990 Tetrahedron 46; 2059-2068) and PCT/GB91/00270.

Preferred preparations are also presented in the following text.

Summary

In summation, the present invention provides compounds for use as steroid sulphatase inhibitors and/or steroid dehydrogenase inhibitors, and pharmaceutical compositions for the same.

EXAMPLES

The present invention will now be described only by way of example.

Example

The inhibition of E1S→E1 for a number of compounds were studied. The degrees of inhibition was determined in accordance with the Protocols defined herein. The data obtained are presented below in Table 1 form. In each assay Coumate 667 was also run as a control. The corresponding degrees of inhibition for this compound is also given.

TABLE 1

| STX No. | Structure | STS IC$_{50}$(nM) | 667 Coumate value |
|---|---|---|---|
| 213 | 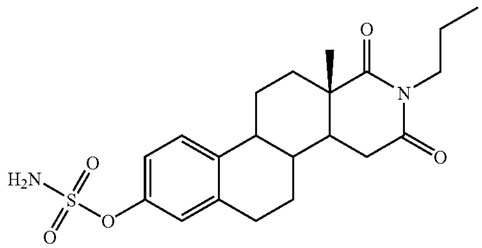 | 41 | 5 nM = 56% Inhibition |
| 236 | 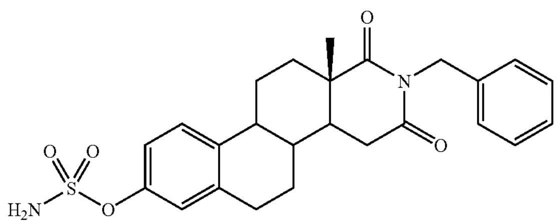 | 280 | 5 nM = 56% Inhibition |
| 280 | 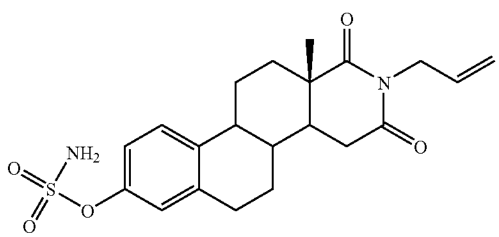 | 75 | IC$_{50}$ = 4.0 nm |
| 281 | 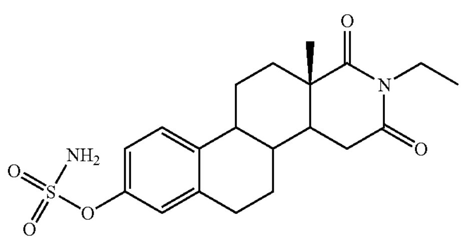 | 52<br>24<br>29 | IC$_{50}$ = 4.1 nm/ 2.9 nm<br>5 nM = 63% Inhibition |
| 282 | 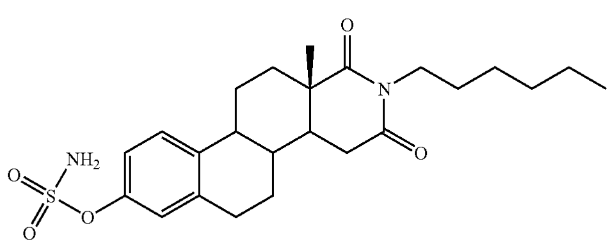 | 288 | IC$_{50}$ = 4.0 nM |

TABLE 1-continued

| STX No. | Structure | STS IC$_{50}$(nM) | 667 Coumate value |
|---|---|---|---|
| 283 | 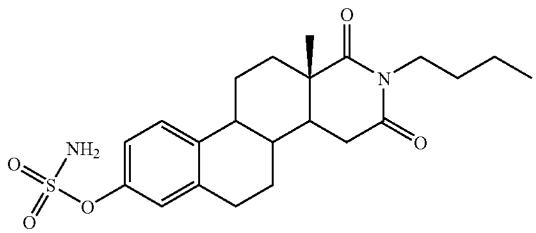 | 382 | IC$_{50}$ = 4.3 nM |
| 284 | 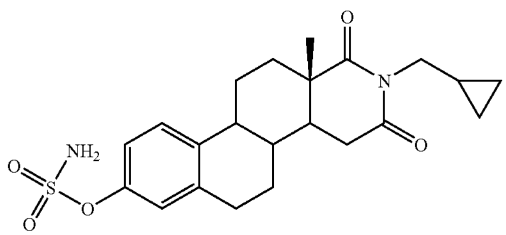 | 74 | IC$_{50}$ = 4.3 nM |
| 285 | 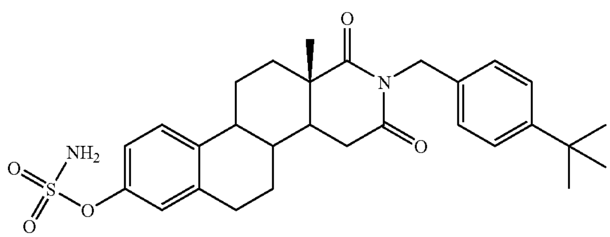 | 23 | 5 nM = 63% Inhibition |
| 286 | 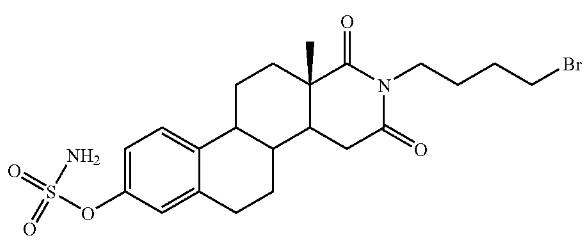 | 12 | 5 nM = 63% Inhibition |
| 326 | 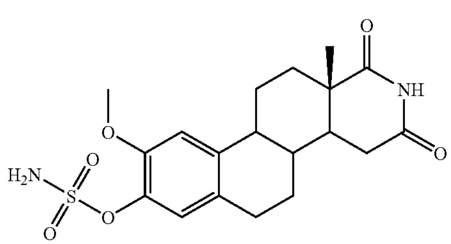 | 309 | IC$_{50}$ = 2.9 nM |

Structures of further compounds in accordance with the present invention and referenced in the present specification are given below.
| STX No. | Structure |
|---|---|
| 187 | 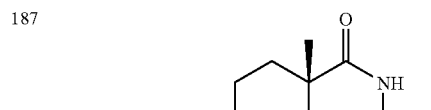 |
| 188 | 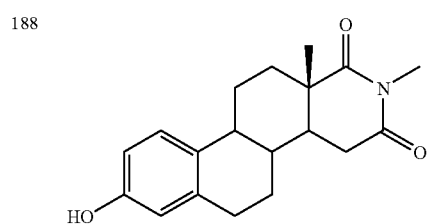 |
| 189 | 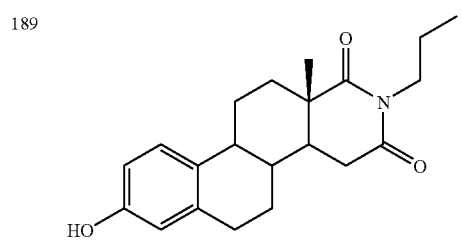 |
| 190 | 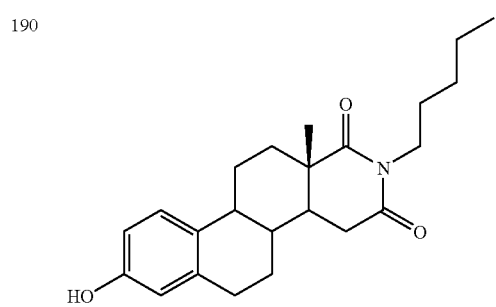 |
| 211 | 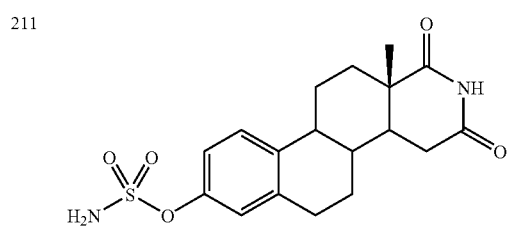 |
| 212 | 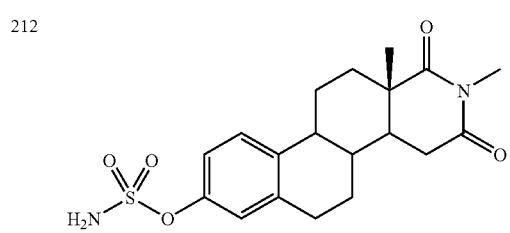 |
| STX No. | Structure |
|---|---|
| 214 | |
| 233 | |
| 234 | |
| 235 | |
| 237 | |
| 274 | |
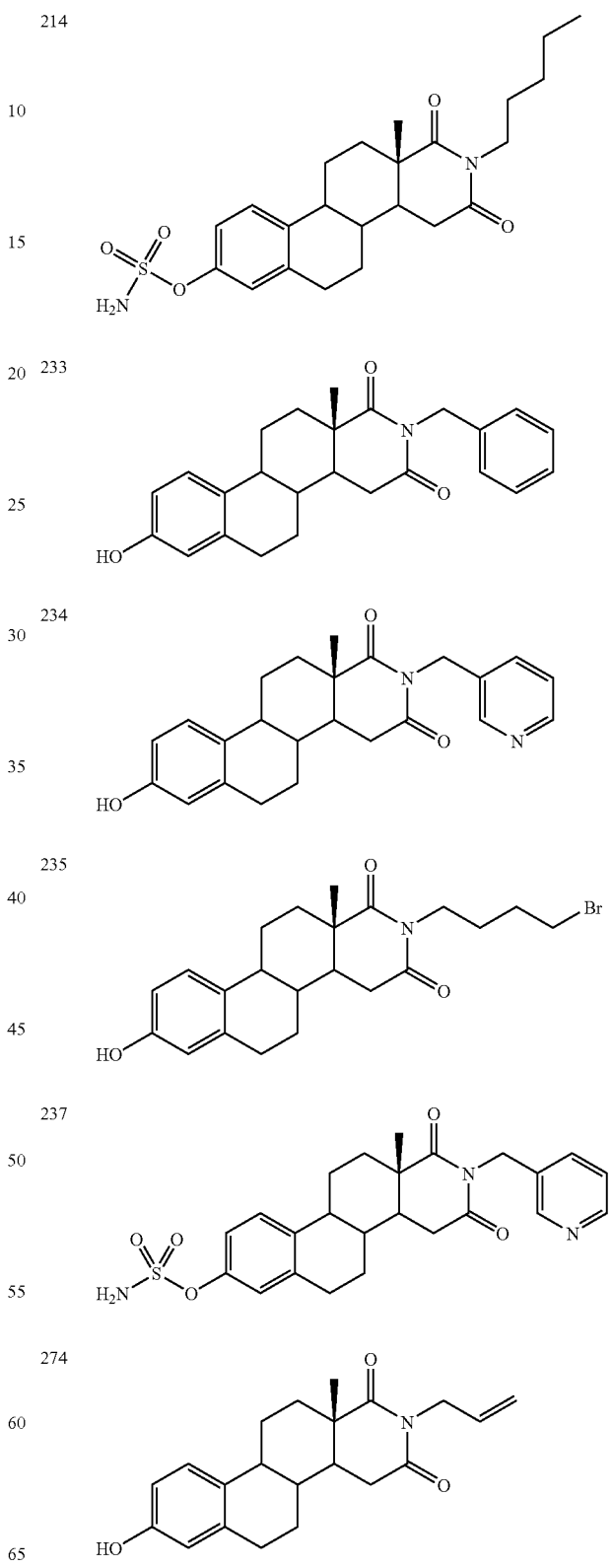

| STX No. | Structure |
|---|---|
| 275 | 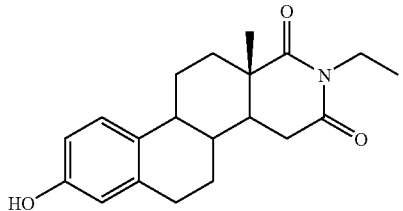 |
| 276 | 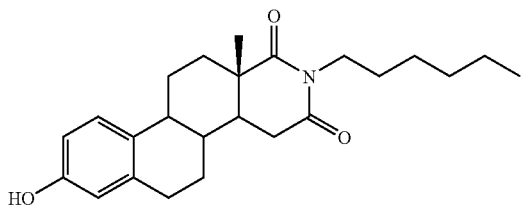 |
| 277 | 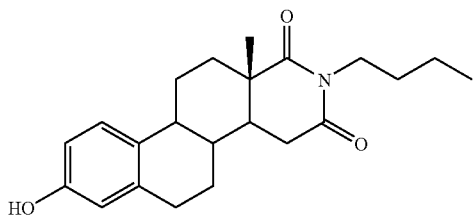 |
| 278 | 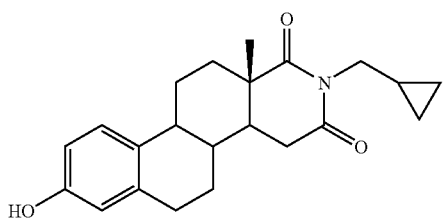 |
| 279 | 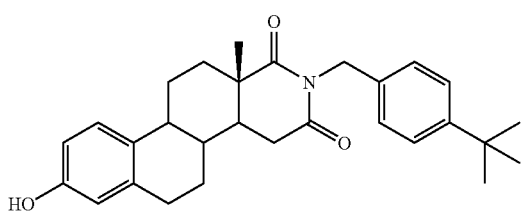 |
| 325 | 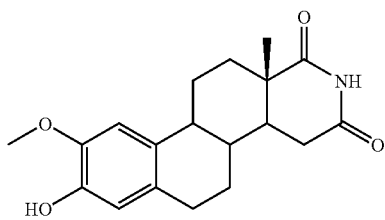 |

Further compounds in accordance with the present invention were synthesised and biological data obtained in the following studies.

Further Studies

Molecules combining both features of STS inhibitors and HSD inhibitors (and in some aspects antiestrogens) have also been developed. Relying on the fact that an alkylamide side-chain can block the oestrogen receptor activation,[23] 3-O-sulfamates derivatives of oestradiol bearing 17β-(N-alkylcarbamoyl) and 17β-(N-alkanoyl) side-chains have been synthesised.[24] The alkyl/alkanoyl group is designed as membrane insertion region that should increase the affinity for the enzyme and decrease the estrogenicity of the steroid. These novel molecules represent potential therapeutic agent for treatment of HDBC since the activity of the heptyl analogues 1 and 2 (below) was found to be similar to that of EMATE with respect to the inhibition of oestrone sulphatase, without being estrogenic.

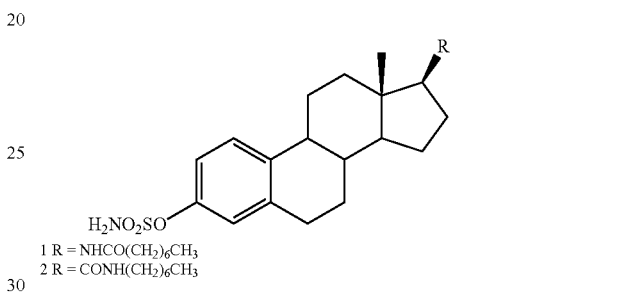

1 R = NHCO(CH$_2$)$_6$CH$_3$
2 R = CONH(CH$_2$)$_6$CH$_3$

Structures of 3-O-sulfamates-C17-derivatives of oestrone bearing N-alkylcarbamoyl side-chains.

While research in the area of STS has generated several highly potent inhibitors, one of which is entering the clinique, 17β-HSD inhibitor design remains a field still ripe for development. To the best of our knowledge, 16α-(bromopropyl)-oestradiol is the most potent inhibitor of 17β-HSD type I which suggests that the D-ring of the steroidal skeleton may play a major role in recognition of the substrate by the enzyme. However, 16α-(bromopropyl)-oestradiol is estrogenic and most of the attempts to reduce its estrogenicity have either failed or resulted in a decrease in its activity.

A potent 17β-HSD type 1 inhibitor, free from agonist activity but possessing anti-estrogenic activity, would be a novel type of agent for the treatment of HDBC since it would act as dual suppresser of oestrogen synthesis and action. It is therefore proposed that attempts to develop such an agent could be focused around the structural features of 3 (or 4) with the addition of some specific modifications aiming at inducing non or anti-oestrogenic properties.

In order to decrease the affinity of the target molecule for the oestrogen receptor and minimizing the chances oestrogen-agonism induced by the drug, it was proposed to replace the 17β-hydroxyl function by a carbonyl group. Oestradiol has indeed a 10-fold greater proliferative effect on breast tumour cells than oestrone suggesting the estrogenicity of 17β-hydroxylated compounds.[33] Optimisation of the non estrogenic properties of these compounds can also be performed by introducing of a methoxy function at position 2 of the A-ring since 2-methoxyestrogens are known to be less estrogenic than their parent estrogens. They could also confer additional properties to the target compounds since they can inhibit tumour growth and angiogenesis.[34]

While the side-chain on the D-ring had to be retained since it is responsible for the activity, the strategy to induce it had to allow more versatility suggesting the need to modify the D-ring itself. Side-chains to be introduced include short to long alkyl moieties or bulky hydrophobic substituents whose effect on the activity of the enzyme can be related to the presence/absence of a hydrophobic pocket. Other types of side-chains such as bromoalkyl or cyclopropyl moieties could potentially interact with a nucleophilic amino-acid residue of the active side and unsaturations could confer rigidity to the side-chains whose orientation in the active site might be a determining factor for inhibition of the enzyme.

In order to achieve these requirements summarized above, compound 5 (below) was postulated as a good candidate. With a structurally modified D-ring, it affords a novel approach to 17β-HSD type 1 inhibition having also the advantage over the above derivative of oestradiol to allow a very easy introduction of side-chains on the N-imido atom of the D-ring. It can also be accessed in one step from benzyl marrianolic acid[35] which has been synthesized in our group from another project.

3-Hydroxy-16,17-seco-estra-1,3,5(10)-triene-16,17-imide, 5 (R═R'═H) and its parents (R=side-chain and R'═H or $SO_2NH_2$)

Synthetic Strategies

In order to establish a structure activity relationship for the family of molecules derived from 5, an efficient synthetic pathway had to be developed, enabling an easy and effective introduction of a wide variety of side-chains on the D-ring.

The most logical approach, allowing versatility during the synthesis of the targets, is to consider the introduction of the side-chains on the D-ring after its conversion into a piperidine dione moiety. It was therefore proposed that, once protected at its C3-position, compound 5 would be a key intermediate for the synthesis of the targets since introduction of the side-chains can easily be performed in one step via N-alkylation. Subsequent deprotection and sulfamoylation would then yield the final phenolic compounds and sulfamates derivatives. Supposing that the key intermediate (framed) is accessible starting from oestrone, a crude synthetic pathway is proposed in Scheme 1.

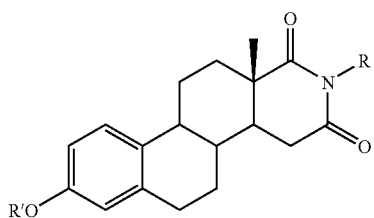

5

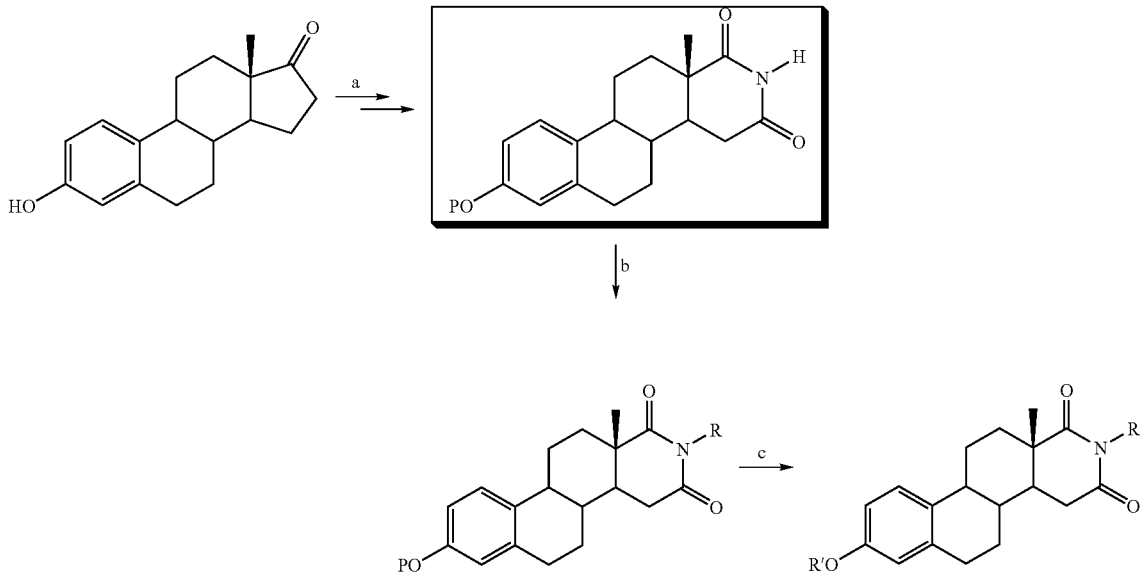

Scheme 1. Proposed synthetic approach to access the target molecules from commercially available oestrone.

P = protecting group, R = side-chain, R' = H or $SO_2NH_2$.
(a) D-ring modification, protection; (b) alkylation; (c) deprotection, sulfamoylation.

The use of rearrangements in order to modify the D-ring of steroids have often been reported in the literature. Jindal et al. have proposed the access to the acetylated derivative of 5 via a Beckmann rearrangement of 16-oximino-estrone 6 (Scheme 2)[37], which we decided to investigate.

Scheme 2. Literature method for the synthesis of 7.

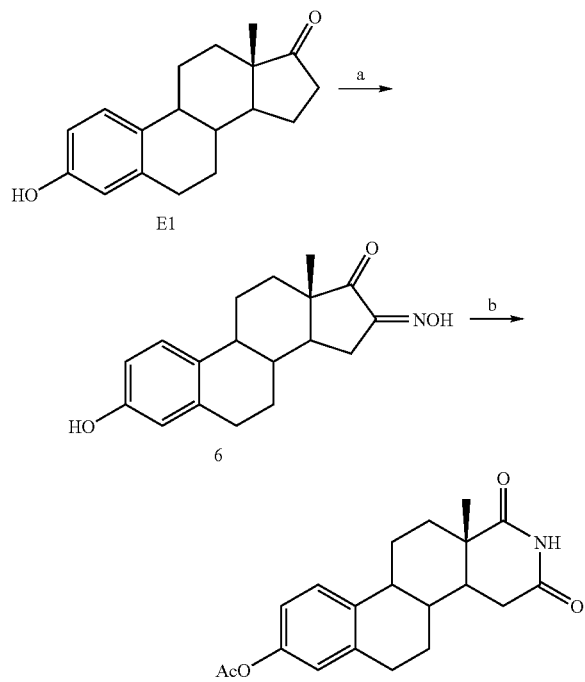

Reagents: (a) KOC(CH$_3$)$_3$, (CH$_3$)$_2$CH(CH$_2$)$_2$ONO; (b) Ac$_2$O/ACOH, reflux.

Deprotonation of oestrone was performed at room temperature under the action of potassium tert-butoxide, freshly prepared by dissolving potassium metal in anhydrous 2-methyl-propan-2-ol. Addition of an excess of isoamyl nitrite gave the keto oxime 6 with a yield of 63%. Beckmann rearrangement of the latter was carried out under refluxing condition of a mixture of acetic acid and acetic anhydride to give 7, isolated with a yield of 57%.

The D-ring modified structure of 7 was fully established and confirmed using spectroscopic methods. Characteristic vibrational bands for the imide system were shown at 1725 and 1690 cm$^{-1}$ on the IR spectrum of the compound and the NH exchangeable proton appeared at 10.64 ppm as a singlet on the $^1$H NMR spectrum. The quaternary carbons C17 and C18 had a characteristic downfield chemical shifts at 171.9 and 178.7 ppm on the $^{13}$C NMR spectrum.

While the Beckmann rearrangement of 6 has the advantage of yielding the intermediate 7 in two steps from oestrone, the overall yield (36%) is rather poor, although comparable with those reported in the literature. It was therefore decided to develop another strategy which would provide 7 in much higher yields.

Modifications of the D-ring through its subsequent cleavage and closure was proposed as an alternative to access derivatives of 5. The D-ring of protected oestrone can indeed be opened via the haloform reaction[35] and closed by thermal condensation with an amine to yield piperidine dione D-ring derivatives of oestrone. Scheme 3 summarizes the pathway envisaged as well as the side-chains to be introduced by N-alkylation.

Scheme 3. Alternative method for the synthesis of 10-21 via benzyl marrianolic acid 9.

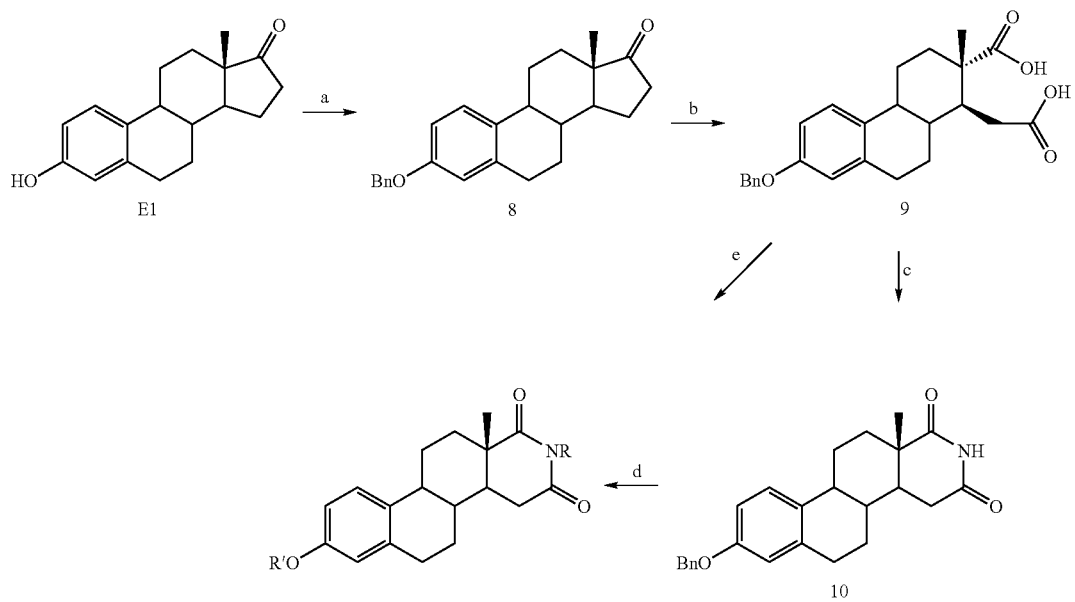

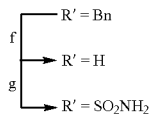
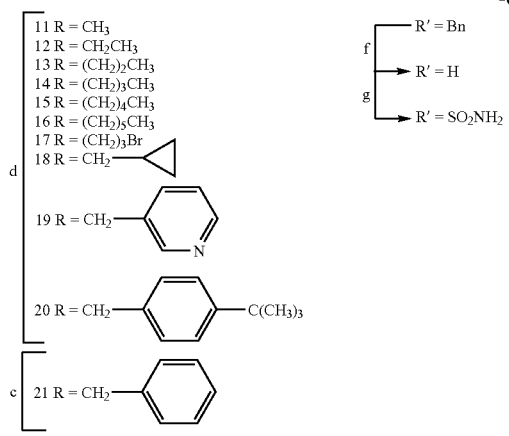

Reagents: (a) NaH/DMF, BnBr, 80° C.; (b) I₂, KOH, MeOH then KOH reflux; (c) urea, 180° C.; (d) NaH/DMF, RX; (e) RNH₂, 180° C; (f) Pd/C, H₂, MeOH/THF; (g) ClSO₂NH₂/DMA.

By reacting benzyl-oestrone 8, which was easily prepared by benzylation of oestrone, with an excess of base (potassium hydroxide) and iodine, the methylene ketone function was bis-halogenated then cleaved. Full conversion into the dicarboxylic acid was achieved by refluxing in a concentrated solution of KOH. Benzyl marrianolic acid 9, which was isolated with an optimised yield of 75%, was then subjected to a thermal cyclisation in presence of urea. This condensation reaction, which leads to the formation of a favorized 6-membered ring, occurs when heating the reagents at 180° C. for a short period of time. The resulting D-ring modified steroid 10 was obtained in high yield (80-89%) giving an overall yield for the synthesis the intermediate 10 of 55%. Thus, despite the presence of an additional step, this alternative method represents a significant improvement over the literature method.

Since imides are too weak bases to attack alkyl halides, they must first be converted into their conjugate bases before undergoing N-alkylation. To this end, 10 was deprotonated using sodium hydride in DMF before reacting, via most likely an $S_N2$ reaction, with various alkylating agents. Following this method, a large number of side-chains have been successfully introduced. Compounds 11-21 were obtained with yields ranging from 75 to 97% and an average reaction time of 2 hours.

N-alkylated compounds can also be directly accessed from benzyl marrianolic acid when this latter is heated in the presence of an alkylamine. The derivative 21 (R=benzyl) was synthesized this way, however, the yield of the reaction was moderate (65%). It was therefore proposed that the direct method from BMA would be employed when exceptionally the alkyl halides are commercially unavailable or deemed unreactive towards the N-alkylation of 10.

Benzyl ether of compounds 11-21 was then cleaved by catalytic hydrogenation using Pd/C to afford the series of hydroxylated targets 22-32 with high yields.

For the introduction of unsaturated side chains, another strategy had to be developed since the last step of Scheme 3 involves a hydrogenolysis which is likely to debenzylate and hydrogenate the unsaturated group concurrently. Although some selective methods for the reduction of benzyl-protected hydroxyl function have been reported,[38] protection of 5 with a tert-butyl-dimethylsilyl group before N-alkylation is a simple effective alternative method Protection of the phenol function of 5 was conducted in presence of tert-butyl-dimethylsilyl chloride and imidazole via the formation of an intermediate reactive species. Alkylation of the resulting protected compound 33 with allyl bromide easily yielded 34, which was deprotected with tetrabutylammonium fluoride. This particular approach (Scheme 4), developed for the introduction of an allyl moiety, should also be applicable to induce other unsaturated groups on the N-atom.

Scheme 4. Synthesis of the N-allyl derivative of 5.

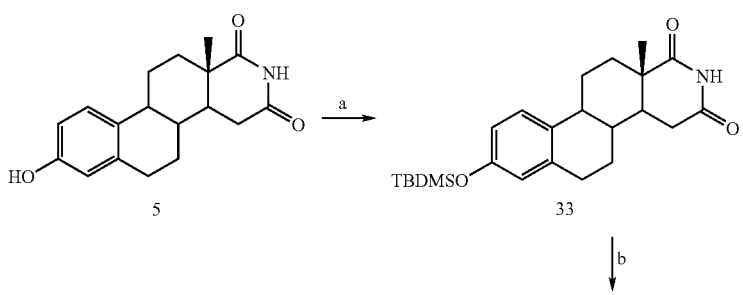

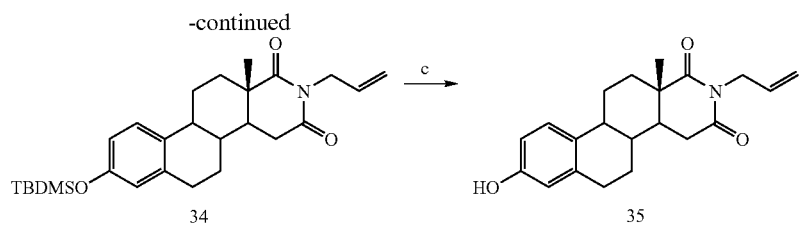

Reagents: (a) TBDMSCl/Imidazole, DMF; (b) NaH/DMF, CH₂CHCH₂Br; (c) TBAF/THF.

Sulfamoylation of the hydroxylated compounds was performed following a recent procedure described by Okada et al.[39] in which sulfamoylation of phenolic compounds is conducted in the aprotic solvent dimethylacetamide in the absence of base. In general, this method, which requires only a slight excess of sulfamoyl chloride, gives a better yield of sulfamates than the usual procedure where NaH/DMF are employed. It is proposed that DMF could undergo a side-reaction with sulfamoyl chloride, which cannot occur with DMA, because of the unavailability of a formyl proton. It was also found that elimination of a base in the reaction conditions led to the highest yields and that probably DMA worked as a moderate base.

Following a procedure developed in our group, hydroxylated derivatives 5, 22-32 and 35 were sulfamoylated in the presence of 2.2 equivalents of sulfamoyl chloride in DMA. Compounds 36-48 were mostly obtained in high yields after short reaction time. However, sulfamoylation of 28 had to be performed according to the initial NaH/DMF method since a side-reaction occurred between the bromobutyl side-chain and sulfamoyl chloride when DMA was the solvent. Unexpectedly, the side-product was found to be a sulfamate of 5 bearing a chlorobutyl side-chain. HPLC analysis of the crude showed that the side-product formed in the same proportions as that of the expected product 43. Despite the presence of two well-separated peaks at 5.5 min and 6.50 min (elution MeOH/H₂O 68:32) on the HPLC run, attempt to separate both products by flash chromatography or recrystallization failed. They were therefore isolated using preparative HPLC and characterized by ¹H NMR and accurate mass spectroscopy.

When the reaction was carried out using NaH/DMF and 6 equivalents of sulfamoyl chloride, 43 was isolated with a yield of 81% as the sole product of the reaction. In this reaction, chlorine resulting from the nucleophilic attack of the phenolate ion on sulfamoyl chloride is trapped as HCl and is therefore unable to react with the bromobutyl side-chain.

Finally, a 2-methoxy derivative of 5 and its sulfamate were synthesized following the same sequence of reaction as that described in Scheme 3, starting from 2-methoxy-estrone. This latter was prepared according to an efficient two steps synthesis developed in our group, where introduction of a methoxy group on position 2 relies on the nucleophilic displacement of an halogen atom by a methoxyde anion.

To this end, 2-iodo-estrone 49 was prepared by treating oestrone with mercuric acetate and iodine in acetic acid.[40] The selective halogenation at position 2 was complete within 2 hours at room temperature with an overall yield of 56% after successive recrystallizations. 2-Iodo-estrone then reacted with a large excess of a freshly prepared solution of sodium methoxyde, in presence of copper chloride in refluxing pyridine[41] and gave 2-methoxy-estrone 50 with a yield of 75%. This method has the advantage of not involving any protecting group and gives good overall yield (42%) for the synthesis of 2-methoxy-estrone in two steps from oestrone.

After benzylation, the resulting compound 51 was subjected to the haloform reaction. A limited solubility of 51 in methanol led to a poor, non-optimised yield of 18% for the synthesis of 52. Ring closure in presence of urea gave 53 with a yield of 59% and subsequent deprotection gave the final products 54. Sulfamoylation of 54 had to be conducted using NaH/DMF with a large excess of sulfamoyl chloride since a the lack of reactivity was observed when the reaction was carried out in DMA. This can be due to the steric hindrance of position 3 resulting from the presence of the methoxy group at position 2.

Scheme 5. Synthesis of the 2-methoxy derivative of 5 and its sulfamate.

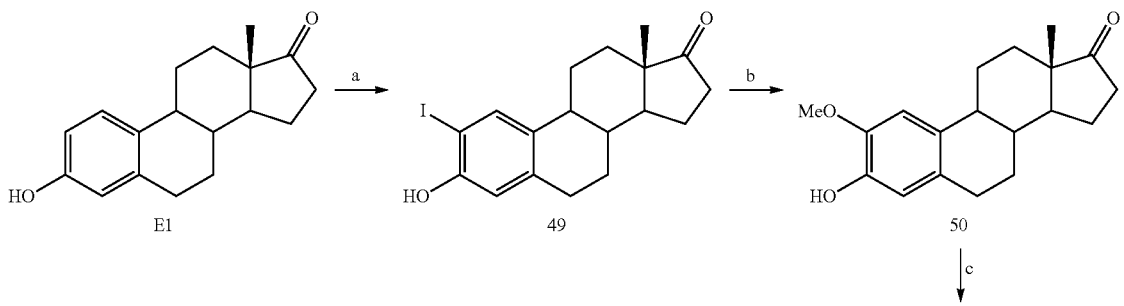

-continued

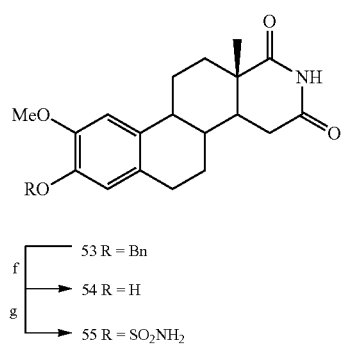

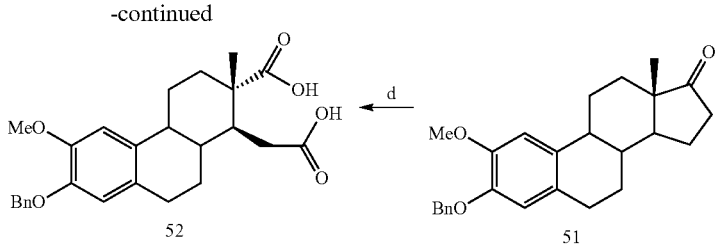

53 R = Bn
f
54 R = H
g
55 R = SO₂NH₂

Reagents: (a) Hg(OAc)₂, I₂, AcOH/THF; (b) CuCl₂/Pyridine, NaOMe, reflux;
(c) KOC(CH₃)₃/DMF, BnBr; (d) I₂, KOH, MeOH then KOH reflux; (e) urea, 180° C.;
(f) Pd/C, H₂, MeOH/THF; (g) ClSO₂NH₂/DMA.

Results and Discussion

The in vitro inhibition data of sulphatase activity for compounds 36, 37, 39, 41, 45 and 47 is shown below. The remaining compounds are found to be STS inhibitors. Each of the compounds described herein is also found to inhibit HSD.

Figure 2:
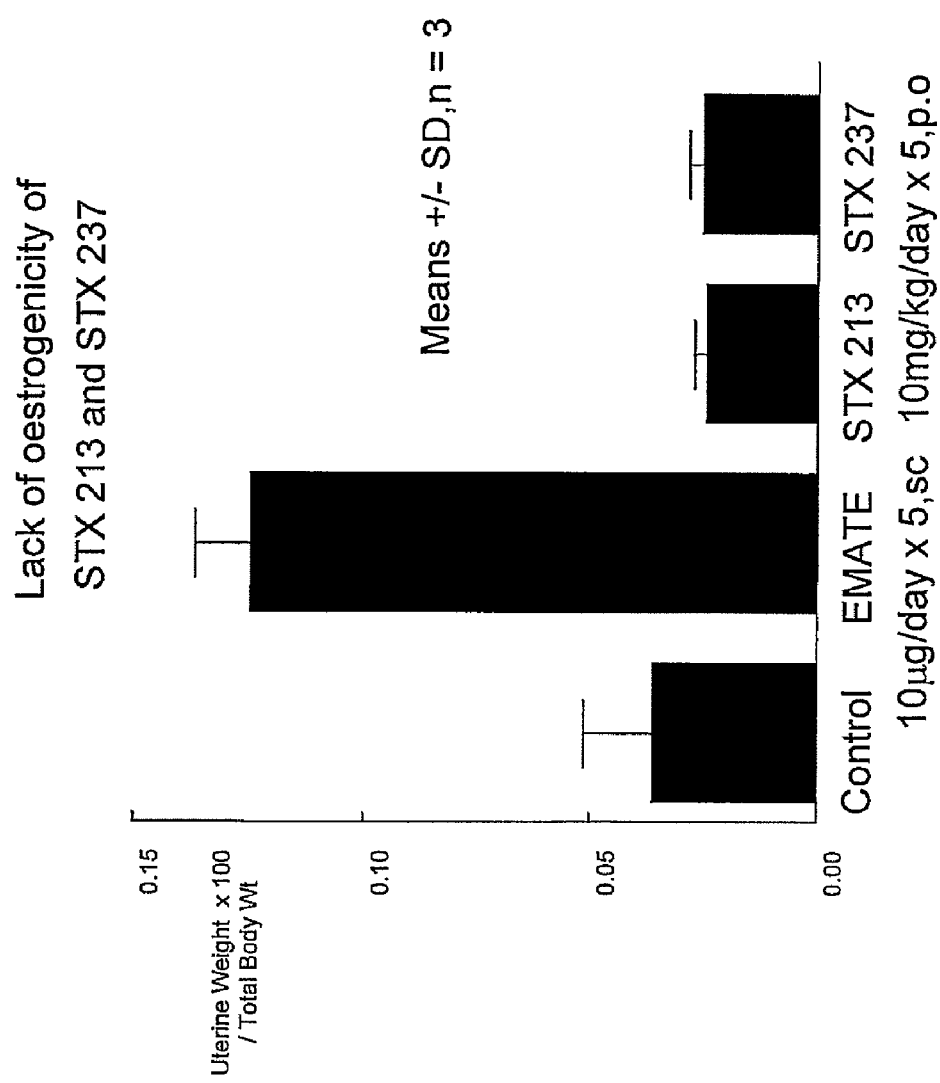
FIG. 2 is a bar graph showing the lack of oestrogenicity of STX213 and STX 237.
Figure 3:
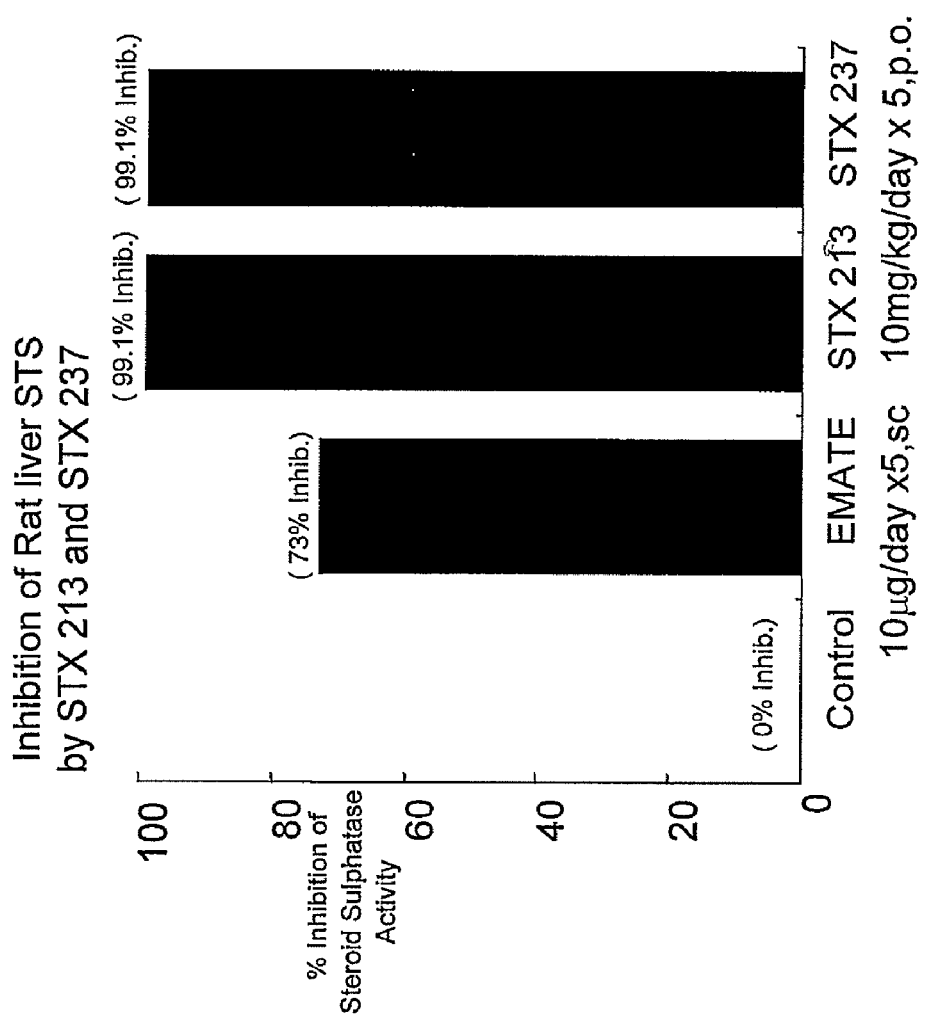
FIG. 3 is a bar graph showing the inhibition of rat liver STS by STX 213 and STX 237.

The ability of compounds 36, 37, 39, 41, 45 and 47 to inhibit oestrone sulphatase activity was examined in human placental microsomes. Incubation of [³H]-oestrone with placental microsomes with or without the inhibitor at various concentrations, followed by isolation of the product by extraction into toluene gave the results presented in Table 2. For the purpose of comparison, activity of EMATE in the different assays was also included. The $IC_{50}$ values, which are used to compare the inhibitory potencies of these D-ring modified steroids, were also calculated.

drawn (FIG. 2—Structure-activity relationship for various side chain lengths vs. the inhibition of the conversion of estrone-sulfate into oestrone catalysed by steroid sulphatase), where the $IC_{50}$ of each compound is plotted in function of the number of carbon atoms in the side-chain. It clearly underlines the difference of activity between compound 41 and the group of compounds 36, 37 and 39.

The loss of activity observed for 41 is rather unexpected since most of the potent steroidal inhibitors of STS are, like 41, derivatives of EMATE and contain bulky hydrophobic side-chains. The most recent example are the 3-O-sulfamates derivatives of oestradiol bearing a 17β-alkylamide side-chain (1 and 2) whose activity was found optimum when the alkyl group was an heptyl moiety. Their potency, similar to that of

TABLE 2

% Inhibition at different concentrations and $IC_{50}$ values for inhibition of human placental steroid sulphatase by various D-ring modified steroids.

| Compound | Mean % Inhibition ± SD | | | | | | $IC_{50}$ (nM) |
| --- | --- | --- | --- | --- | --- | --- | --- |
| | 0.1 nM | 1 nM | 10 nM | 100 nM | 1 µM | 10 µM | |
| EMATE | — | — | — | — | — | — | 8 |
| 36 | −6.5 ± 3.6 | −2.5 ± 3.0 | 17.4 ± 32.3 | 72.6 ± 3.1 | 93.8 ± 4.2 | 98.7 ± 2.7 | 20 |
| 37 | 4.7 ± 3.0 | 15.0 ± 2.6 | 46.4 ± 6.0 | 81.9 ± 3.3 | 96.4 ± 5.1 | 99.1 ± 0.2 | 12 |
| 39 | 21.2 ± 0.8 | 49.3 ± 1.2 | 64.1 ± 4.6 | 84.6 ± 1.3 | 96.8 ± 0.8 | 99.3 ± 1.1 | 1 |
| 41 | 2.9 ± 3.6 | −11.2 ± 7.8 | −5.1 ± 4.0 | 41.3 ± 3.3 | 90.7 ± 1.6 | 98.5 ± 0.5 | 150 |

Of the different compounds tested, the steroids bearing a propyl, a benzyl and a 2-methyl pyridyl moiety on the nitrogen atom of the piperidine dione D-ring were the most potent with $IC_{50}$ between 1 nM and 3 nM. They are therefore more potent than EMATE with, in particular, compound 45 which is 18 times more potent. Compound 36, which has no substitution at the N-atom and 37 the N-methyl derivative were not as potent as 39. Their $IC_{50}$ values of 20 nM and 12 nM respectively however suggests that their potencies are similar to that of EMATE. Unexpectedly, compound 41, whose side-chain is a n-pentyl moiety, showed a dramatic decrease in potency with an $IC_{50}$ value of 150 nM. This loss in potency is rather steep suggesting that the enzyme is not accommodative for any long hydrophobic N-substituent and is very sensitive to the change of its size.

From the different data obtained for the linear alkyl side-chains, a limited structure activity relationship graph has been EMATE, clearly underlines the presence of a hydrophobic pocket in the enzyme active site corresponding to the direction of the 17β-substituent.

A weaker inhibition of STS by 41 therefore suggests that the orientation of its side-chain, situated on the N-atom of the D-ring (6-membered), is different enough from that of the 17β-side-chain of 1 or 2 (5-membered D-ring) to induce a decrease of affinity with the active site of the enzyme. It can be proposed that, while there is a hydrophobic pocket in the enzyme active site for 17β-substituents, the topology of the active site around the N-position of a 6-membered ring could be more restrictive to bulky substituents. To corroborate this hypothesis, molecular modelling would be a tool of choice.

In order to elucidate the orientation of the atoms in the D-ring and in the side-chain, as well as gather data for possible future molecular modelling studies, the crystal structure of the highly potent oestrone derivative 39 was determined. A crystal (approx. dimensions 0.20×0.17×0.08 mm), obtained from slow recrystallization in acetone/hexane, was used for data collection.

The ORTEP plot of the asymmetric unit of 41 is shown below along with the labelling scheme used. The sulfamate group, all four rings, and the key features of the modified D-ring are clearly visible. As expected, the D-ring is in a half chair conformation since the imide function implies the position of the atoms C13, C17, N and C1' as well as C15, C16, N and C1' in the same plan.

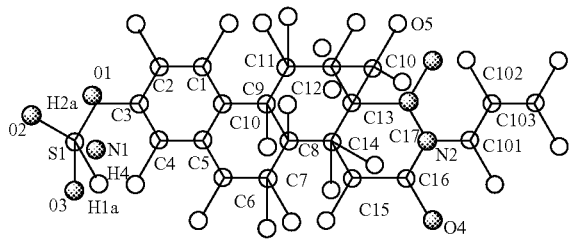

ORTEP plot of the X-ray crystal structure of 41. Ellipsoids are shown at the xx % probability level.

When compared with the ORTEP plot of the X-ray crystal structure of EMATE,[42] it clearly appears that the C17β-orientation of EMATE and the N-alkyl orientation of the 6-membered ring of 41 are different, therefore interacting with different areas of the active site of STS.

Good inhibition of STS by 45, and in a minor extend by 47, seem to indicate the presence of a hydrophobic binding area in the active site, even though it does not seem to be accommodative for a pentyl moiety. However, it is also known that benzyl groups (and benzyl-related groups) are more hydrophobic and less sterically restrictive with a total of 7 carbons than would be a linear heptyl side-chain. This could explain the difference of potency between compounds 45 or 47 and 41, all with hydrophobic substituents. The higher activity found for 45 could also suggest the presence of hydrogen bonding donors among the amino acids residues of the active site.

Additional biological results are however needed to fully interpretate the data obtained so far. Activity of compounds 38, 40 and 42 (respectively ethyl, butyl and hexyl derivatives) would represent useful data which might enable the interpretation of the $IC_{50}$ values obtained so far in terms of topology of the active site.

For the time being, the crystal structure parameters of 41 will be useful in exploring the interactions of this type of molecule with proteins by computer-aided molecular modelling and assist the design of new potent molecules.

Summary

Breast cancer is a disease of major importance in Europe and Northern America. In Britain, it kills more people than any other type of cancer. Hormone dependant breast cancer represents about two third of those cases in postmenopausal women; it corresponds to a type of breast cancer in which tumours rely on estrogens for their growth and development. Endocrine therapy, where oestrogen circulating levels are controlled via the use of drugs that inhibit one or several enzymatic pathway in oestrogen biosynthesis, is the response for HDBC. Different targets can be considered and most of the work has been done around antiestrogens and aromatase inhibitors. The enzymes steroid sulphatase and 17β-HSD type 1 have later emerged as potent targets.

While several potent inhibitors have been developed for STS, 17β-HSD type 1 has not raised as much interest and only few active molecules have been reported. Relying on the fact that D-ring derivatives of EMATE are potent inhibitors of 17β-HSD type 1, we initiated the design and synthesis of analogs of EMATE with reduced estrogenicity. This has led to a series of compounds where the D-ring is a piperidine dione moiety and where the N-atom is bearing a variety of side-chains.

Biological testing against STS, which was performed on breast cancer cells, revealed a very high activity for derivatives bearing a propyl or a picolyl side-chain. With an $IC_{50}$ of 1 nM, they are much more potent than EMATE.

Experimental

1—General Methods

All chemicals were either purchased from Aldrich Chemical Co. (Gillingham, Dorset, UK) or Lancaster Synthesis (Morecambe, Lancashire, U.K.). All organic solvents of A. R. grade were supplied by Fisons plc (Loughborough, U.K.). Anhydrous N,N-dimethylformamide (DMF) and N,N-dimethylacetamide (DMA), respectively used for all N-alkylations and sulfamoylation reactions, were purchased from Aldrich and were stored under a positive pressure of $N_2$ after use. Sulfamoyl chloride was prepared by an adaptation of the method of Apel and Berger[48] and was stored as a solution in toluene as described by Woo et al.[16] An appropriate volume of this solution was freshly concentrated in vacuo immediately before use.

E1S and E1 were purchased from Sigma Chemical Co. (Poole, U.K.). [6,7-$^3$H]E1S (specific activity, 50 Ci/mmol) and [4-$^{14}$C]E1 (specific activity, 52 mCi/mmol) were purchased from New England Nuclear (Boston, Mass.). [6,7-$^3$H] E1 (specific activity, 97 Ci/mmol) was obtained from the Amersham International Radiochemical Centre (Amersham, U.K.).

Thin layer chromatography (TLC) was performed on precoated plates (Merck TLC aluminium sheets silica gel 60 $F_{254}$, Art. No. 5554). Product(s) and starting material (SM) were detected by either viewing under UV light or treating with a methanolic solution of phosphomolybdic acid followed by heating. Flash column chromatography was performed on silica gel (Sorbsil C60). IR spectra were determined as KBr discs using a Perkin-Elmer Spectrum RXI FT-IR and peak positions are expressed in $cm^{-1}$. $^1$H NMR and DEPT-edited $^{13}$C NMR spectra were recorded with JMN-GX 400 NMR spectrometers, and chemical shifts are reported in parts per million (ppm, δ) relative to tetramethylsilane (TMS) as an internal standard. The following abbreviations are used to describe resonances in $^1$H NMR and $^{13}$C NMR spectra: br, broad; s, singlet; d, doublet; t, triplet; q, quartet; m, multiplet and combinations such as dd, doublet of doublets. Chemical shifts for AB systems ($δ_A$ and $δ_B$) were approximated by taking the middle of each doublet and the corresponding coupling constant labelled $J_{AB}$ or $J_{BA}$. As an example, $δ_A$ and $δ_B$ were calculated following the formula shown in appendix 2 for compound 21. HPLC analysis were performed on a Waters Millenium$^{32}$ instrument equipped with a Waters 996 PDA detector. The traces were recorded on a Waters Radial-pack C18, 8×100 mm column eluted with a methanol/water gradient at 2 mL/min. Mass spectra were recorded at the Mass Spectrometry Service Center, University of Bath. FAB-MS were carried out using m-nitrobenzyl alcohol (NBA) as the matrix, and elemental analyses were performed by the Microanalysis Service, University of Bath. Melting points were determined using a Reichert-Jung Thermo Galen Kofler block and are uncorrected. The X-ray crystallographic study of 39 was carried out by Dr. M. Mahon in the Department of Chemistry, University of Bath.

1-1—Biological Assays

All assays were performed at the Department of Endocrinology and Metabolic Medicine, Imperial College School of Medicine, St. Mary's Hospital, London by and in collaboration with Dr. A. Purohit and Pr. M. Reed.

The ability of the compounds synthesised to inhibit steroid sulphatase activity was examined using placental microsomal preparations. Placental microsomes (100000 g fraction) were prepared from a positive-positive human placenta from a normal-term pregnancy.[49] To determine the $IC_{50}$s for the inhibition of oestrone sulphatase, activity was measured in the presence of the inhibitor (0.05-1.0 µM) using [$^3$H]E1S (4×10$^5$ dpm) adjusted to 20 µM with unlabeled substrate.[14] After incubation of the substrate±inhibitor with placental microsomes (125 µg of protein/mL) for 30 minutes, the product formed was isolated from the mixture by extraction with toluene (4 mL), using [4-$^{14}$C]E1 to monitor procedural losses.

1-2—Preparation of Sulfamoyl Chloride

Formic acid (6 mL, 150 mmol) was added dropwise to a stirred solution of chlorosulfonyl isocyanate (25 g, 150 mmol) in 150 mL of freshly distilled toluene at 0° C. under an atmosphere of $N_2$. The resulting white suspension was stirred overnight at room temperature under $N_2$ and the insoluble was filtered out of the solution under $N_2$ using a cannule. The filtrate was concentrated in vacuo to give a light brown crude of sulfamoyl chloride. A standard solution (ca 0.70 M) of sulfamoyl chloride was then prepared by dissolving the crude crystalline product in freshly distilled toluene and stored in the refrigerator under $N_2$. Prior to the reaction, formic acid was stirred overnight with boric anhydride and freshly distilled under $N_2$.

1-3—General Method for Alkylation

Sodium hydride (60% dispersion in mineral oil, 1.2 eq) was added to a stirred solution of 10 in anhydrous DMF (15 mL) at 0° C. under an atmosphere of $N_2$. After evolution of hydrogen had ceased, the parent alkylating agent (2 eq.) was added. The reaction mixture was stirred at room temperature and poured into water (50 mL). The resulting solution was extracted into ethyl acetate (50 mL). After further exhaustive washing with brine (4×25 mL), the organic layer was dried ($MgSO_4$), filtered and evaporated in vacuo. Fractionation of the crude product that obtained by flash chromatography gave the parents compounds 11-21.

1-4—General Method for Hydrogenolysis

Pd—C (10%) was added to a solution of 10-21 in MeOH/THF and the resulting suspension was hydrogenated at room temperature using a hydrogen-filled balloon. After removal of the supported catalyst by filtration and evaporation of the filtrate in vacuo, the product obtained was partially (analytical sample) or fully purified to give the parent compounds and 22-32.

1-5—General Method for Sulfamoylation

To a stirred solution of sulfamoyl chloride (2.2 eq.) in DMA at 0° C. under an atmosphere of $N_2$ was added 5, 22-32 and 35. The reaction mixture was stirred under $N_2$ in which time it was allowed to warm to room temperature. It was then poured into cold brine (15 mL), and the resulting solution was extracted with ethyl acetate (2×20 mL). The organic layers were combined, washed with brine (6×20 mL), dried ($MgSO_4$), filtered and concentrated under reduced pressure. The crude product that obtained was fractionated by flash chromatography and/or recrystallized.

2—Synthesis
2-1—Synthesis of the D-Ring Modified Steroidal Moiety

16-oximino-estrone 6

To a stirred solution of potassium tert-butoxide under an atmosphere of $N_2$, freshly prepared by dissolving potassium metal (80 mg, 2.05 mmol) in 2 mL tert-butanol, oestrone (200 mg, 740 mmol) was added. The reaction mixture was then stirred for 1 hour at room temperature under $N_2$ and isoamyl nitrite (180 µmol, 1.34 mmol) was added dropwise. The deep red mixture obtained was stirred overnight and then poured into water (20 mL). The resulting solution was extracted with ether (2×20 mL) and the aqueous layer was acidified with glacial acetic acid (10 mL) to give a light yellow precipitate. This was left separating for two hours after which the solid was filtered (140 mg, 63%): mp 223-225° C. (lit. 226-227° C.);[43] TLC (chloroform/acetone, 9:1) $R_f$ 0.27 cf. $R_f$ 0.69 (E1); IR (KBr) 3385 (NOH), 2920-2860 (aliph CH), 1735 (C=O), 1605-1500 (arom C=C) cm$^{-1}$; $\delta_H$ (DMSO-$d_6$, 400 MHz) 0.89 (3H, s, C-18-$H_3$), 1.30-2.85 (11H, m), 2.70-2.81 (2H, m, C-6-$H_2$), 6.46 (1H, d, $J_{C-2-H,C-4-H}$=2.3 Hz, C-4-H), 6.52 (1H, dd, $J_{C-1-H,C-2-H}$=8.4 Hz and $J_{C-4-H,C-2-H}$=2.3 Hz, C-2-H), 7.05 (1H, d, $J_{C-2-H,C-1-H}$=8.2 Hz, C-1-H), 9.05 (1H, s, exchanged with $D_2O$, OH) and 12.39 (1H, s, exchanged with $D_2O$, NOH); $\delta_C$ (DMSO-$d_6$, 100.4 MHz) 14.09 (q, C-18), 25.09 (t), 25.46 (t), 26.18 (t), 29.02 (t), 30.92 (t), 37.20 (d), 43.20 (d), 44.59 (d), 48.50 (s, C-13), 112.70 (d), 114.83 (d), 125.82 (d), 129.59 (s), 136.88 (s), 154.84 (s, C-3 or C-16), 155.23 (s, C-3 or C-16) and 204.64 (s, C=O); MS m/z (FAB+) 453.2 [30, (M+H+NBA)$^+$], 300.1 [100, (M+H)$^+$]; MS m/z (FAB-) 451.3 [38, (M-H+NBA)$^-$], 298.2 [100, (M-H)$^-$]; Acc MS m/z (FAB+) 300.15963, $C_{18}H_{22}NO_3$ requires 300.15997. CHN,

3-Acetoxy-16-oximino-estrone

A suspension of 6 (150 mg, 501 mmol) in a mixture of 4.5 mL of glacial acetic acid and 7.5 mL of acetic anhydride was heated to reflux under an atmosphere of N2 for 20 hours. The solvent mixture was then removed under reduced pressure and water was added. After basification with aqueous NaOH, the resulting solution was extracted with ethyl acetate (2×20 mL). The organic layer was separated, washed with water (2×15 mL), then brine (2×15 mL), dried ($MgSO_4$), filtered and concentrated under reduced pressure. Fractionation of the crude product that obtained by flash chromatography with chloroform as eluent gave 7 as a light yellow solid (97 mg, 57%): mp 189-193° C. (lit. 196-198° C.);[43] CHN TLC (chloroform/acetone, 9:1) $R_f$ 0.68 cf. $R_f$ 0.31 (6); IR (KBr) 3205 (NH), 2940-2860 (aliph CH), 1760 (OCOCH$_3$), 1725 (C=O), 1690 (C=O), 1610-1495 (arom C=C) cm$^{-1}$; $\delta_H$ (DMSO-$d_6$, 400 MHz) 1.11 (3H, s, C-18-$H_3$), 1.20-2.72 (11H, m), 2.77-2.84 (2H, m, C-6-$H_2$), 2.23 (3H, s, OAc), 6.81 (1H, d, $J_{C-2-H,C-4-H}$=2.7 Hz, C-4-H), 6.87 (1H, dd, $J_{C-1-H,C-2-H}$=8.4 Hz and $J_{C-4-H,C-2-H}$=2.5 Hz, C-2-H), 7.32 (1H, d, $J_{C-2-H,C-1-H}$=8.2 Hz, C-1-H) and 10.64 (1H, s, exchanged with $D_2O$, NH); $\delta_C$ (DMSO-$d_6$, 100.4 MHz)$^c$ 15.96 (q, C-18), 20.68 (q, COCH$_3$), 24.76 (t), 24.86 (t), 28.79 (t), 32.18 (t), 32.55 (t), 37.29 (d), 40.30 (d), 41.89 (d), 118.62 (d), 120.94 (d), 125.91 (d), 136.46 (s), 137.12 (s), 147.91 (s, C-3), 168.85 (s, COCH$_3$), 171.93 (s, C=O) and 178.71 (s, C=O); MS m/z (FAB+) 495.2 [10, (M+H+NBA)$^+$], 342.1 [100, (M+H)$^+$], 299.1 [40, (M+H-Ac)$^+$]; MS m/z (FAB-)

647.3 [12, (M+2NBA)⁻], 493.2 [34, (M–H+NBA)⁻], 340.1 [100, (M–H)⁻]; Acc MS m/z (FAB+) 342.17046, $C_{20}H_{24}NO_4$ requires 342.17053

*c*-13 signal is hidden under lie solvent peaks

Oestrone 3-benzyl ether (8)

Sodium hydride (60% dispersion in mineral oil, 0.68 g, 20.34 mmol) was added to a stirred solution of E1 (5.0 g, 18.49 mmol) in anhydrous DMF (50 mL), at 0° C. under an atmosphere of $N_2$. After stirring the resulting mixture for an additional 15 minutes, benzyl bromide (2.42 mL, 20.34 mmol) was added and the reaction mixture was heated at 80° C. for 4 hours. The excess of sodium hydride remaining was quenched by pouring the reaction mixture into ice/water. The organic fraction that separated was extracted into ethyl acetate (150 mL) and further washed exhaustively with water (4×50 mL), dried ($MgSO_4$), filtered and evaporated in vacuo. The pale yellow residue that obtained was recrystallized from isopropyl alcohol to give 8 as white flaky crystals (4.73 g, 71%): mp 129-131° C. (lit. 130-131° C.)ref; TLC (chloroform/ethyl acetate, 4:1) $R_f$ 0.83 cf. $R_f$ 0.61 (E1); IR (KBr) 3100 (arom CH), 2950-2840 (aliph CH), 1730 (C=O), 1600, 1500 (arom C=C) cm⁻¹; $\delta_H$ ($CDCl_3$, 400 MHz) 0.91 (3H, s, C-18-$H_3$), 1.41-2.54 (13H, m), 2.86-2.93 (2H, m, C-6-$H_2$), 5.04 (2H, s, $OCH_2Ar$), 6.73 (1H, d, $J_{C-2-H,C-4-H}$=2.3 Hz, C-4-H), 6.80 (1H, dd, $J_{C-1-H,C-2-H}$=8.6 Hz and $J_{C-4-H,C-2-H}$=2.7 Hz, C-2-H), 7.20 (1H, d, $J_{C-2-H,C-1-H}$=8.6 Hz, C-1-H) and 7.30-7.44 (5H, in, $C_6H_5$).

3-Benzyl-marrianolic acid (9)

A solution of iodine (7.6 g, 29.94 mmol) in 95 mL of MeOH and a solution of KOH (13.7 g) in 27 mL of water and 61 mL of MeOH were added dropwise and alternatively to a stirred solution of oestrone 3-benzyl ether (8) (3.8 g, 10.54 mmol) in MeOH (1 L) so that the colour of the mix remains orange/brown. The addition was carried out over 45 minutes and the resulting light yellow solution was stirred overnight at room temperature under an atmosphere of $N_2$ to give a clear light yellow solution. The mixture was then concentrated in vacuo and poured into water (800 mL). After acidification with 5M HCl, the organic fraction was extracted into ether (600 mL) and the ethereal layer washed with aqueous sodium thiosulfate (4×100 mL), then water (4×100 mL), dried ($MgSO_4$), filtered and evaporated in vacuo. The resulting yellow foam (4.54 g) was then dissolved in a solution of KOH (7.6 g) in $McOH/H_2O$ (1:2, 228 mL) and heated to reflux for 4 hours. The orange mixture that obtained was poured into water (800 mL) and after acidification with 5M HCl the organic fractions were extracted into ethyl acetate (300 mL). After further exhaustive washing with brine (4×200 mL), the organic layer was dried ($MgSO_4$), filtered and evaporated in vacuo to give a yellow residue (4.32 g). This was recrystallized from $CHCl_3$/Hexane 5:3 to give 9 as a creamy powder (2.291 g, 53%). A further crop of the product (958 mg) was obtained from the residue of the mother liquor upon recrystallization from $CHCl_3$/Hexane 5:3 (overall yield 75%): mp 212-215° C. (lit. 226-227° C.);[42] TLC (chloroform/methanol, 5:1) $R_f$ 0.37 cf. $R_f$ 0.88 (8); IR (KBr) 3050-2650 ($CO_2H$), 1700 (C=O), 1600-1500 (arom C=C) cm⁻¹; $\delta_H$ (DMSO-$d_6$, 400 MHz) 1.02 (3H, s, C-18-$H_3$), 1.20-2.78 (11H, m), 2.72-2.76 (2H, m, C-6-$H_2$), 5.05 (2H, s, $OCH_2Ar$), 6.68 (1H, d, $J_{C-2-H,C-4-H}$=2.7 Hz, C-4-H), 6.75 (1H, dd, $J_{C-1-H,C-2-H}$=8.6 Hz and $J_{C-4-H,C-2-H}$=2.3 Hz, C-2-H), 7.18 (1H, d, $J_{C-2-H,C-1-H}$=8.9 Hz, C-1-H), 7.30-7.42 (5H, m, $C_6H_5$) and 12.14 (2H, s, exchanged with $D_2O$, $CO_2H$); $\delta_C$ (DMSO-$d_6$, 100.4 MHz) 15.37 (q, C-18), 25.84 (t), 26.53 (t), 29.73 (t), 35.77 (t), 36.10 (t), 40.73 (d), 41.84 (d), 42.55 (d), 46.21 (s, C-13), 68.93 (t, $OCH_2Ar$), 112.35 (d), 114.02 (d), 126.32 (d), 127.29 (2×d), 127.49 (d), 128.19 (2×d), 131.64 (s), 137.18 (2×s), 155.96 (s, C-3), 173.93 (s, $CO_2H$) and 178.60 (s, $CO_2H$); MS m/z (FAB+) 408.2 [41, M⁺], 91.1 [100, $(CH_2Ar)^+$]; Acc MS m/z (FAB+) 408.19404, $C_{25}H_{28}O_5$ requires 408.19367.

3-Benzyloxy-16,17-seco-estra-1,3,5(10)-triene-16,17-imide (10)

3-Benzyl-marrianolic acid (9) (3.25 g, 7.96 mmol) and urea (3.25 g, 54.11 mmol) were heated at 180° C. under an atmosphere of $N_2$ for 45 minutes. The resulting brown residue was then crushed and acetone was added (200 mL) to give a brown suspension. This mixture was concentrated to ca 100 mL, silica gel was added and the solvent was removed to give an homogeneous beige powder which was transferred onto a wet packed (chloroform) flash chromatography column. Elution with chloroform/acetone (96:4) gave 10 as a white residue (2.75 g, 89%): mp 225-226° C.; TLC (chloroform/acetone, 9:1) $R_f$ 0.62 cf. $R_f$ 0.14 (9); IR (KBr) 3260 (NH), 2900-2870 (aliph CH), 1720 (C=O), 1700 (C=O), 1600-1500 (arom C=C) cm⁻¹; $\delta_H$ (DMSO-$d_6$, 400 MHz) 1.09 (3H, s, C-18-$H_3$), 1.20-2.72 (11H, m), 2.76-2.80 (2H, m, C-6-$H_2$), 5.05 (2H, s, $OCH_2Ar$), 6.72 (1H, d, $J_{C-2-H,C-4-H}$=2.3 Hz, C-4-H), 6.76 (1H, dd, $J_{C-1-H,C-2-H}$=8.5 Hz and $J_{C-4-H,C-2-H}$=2.7 Hz, C-2-H), 7.19 (1H, d, $J_{C-2-H,C-1-H}$=9.0 Hz, C-1-H), 7.31-7.44 (5H, m, $C_6H_5$) and 10.63 (1H, s, exchanged with $D_2O$, NH); $\delta_C$ (DMSO-$d_6$, 100.4 MHz) 16.16 (q, C-18), 25.06 (t), 25.25 (t), 29.25 (t), 32.37 (t), 32.72 (t), 37.82 (d), 40.32 (d), 40.49 (s), 41.91 (d), 68.89 (t, $OCH_2Ar$), 112.25 (d), 114.08 (d), 126.00 (d), 127.27 (2×d), 127.45 (d), 128.16 (2×d), 131.51 (s), 137.01 (s), 137.12 (s), 155.97 (s, C-3), 172.09 (s, C=O) and 178.89 (s, C=O); MS m/z (FAB+) 543.3 [8, (M+H+NBA)⁺], 390.2 [58, (M+H)⁺], 91.1 [100, ($CH_2Ar$)+]; Acc MS m/z (FAB+) 390.20586, $C_{25}H_{28}NO_3$ requires 390.20692. For HPLC and CHN analysis, a sample was recrystallized from EtOH to give colourless needles. HPLC (methanol/water, 85:15; $\lambda_{max}$=278.1 nm) Rt=8.15 min, 100%. Found: C, 76.90; H, 6.99; N, 3.73. $C_{25}H_{27}NO_3$ requires: C, 77.09; H, 6.99; N, 3.60.

2-2—Introduction of Various Side Chains on the D-Ring via N-Alkylations

3-Benzyloxy-N-methyl-16,17-seco-estra-1,3,5(10)-triene-16,17-imide (11)

Following the alkylation conditions (see VI-1-3), 10 (500 mg, 1.28 mmol) was treated with NaH (62 mg, 1.54 mmol) and the subsequent reaction with methyl iodide (160 μL, 2.57 mmol) was complete within 45 minutes. Fractionation of the crude product that obtained by flash chromatography with chloroform as eluent gave 11 as a white residue (432 mg, 83%): mp 118-121° C.; IR (KBr) 3160-3060 (arom CH), 2920-2870 (aliph CH), 1720 (C=O), 1670 (C=O), 1600-1500 (arom C=C) cm⁻¹; $\delta_H$ ($CDCl_3$, 400 MHz) 1.17 (3H, s, C-18-$H_3$), 1.26-3.00 (11H, m), 2.86-2.91 (2H, m, C-6-$H_2$), 3.15 (3H, s, N—$CH_3$), 5.04 (2H, s, $OCH_2Ar$), 6.72 (1H, d, $J_{C-2-H,C-4-H}$=2.7 Hz, C-4-H), 6.80 (1H, dd, $J_{C-1-H,C-2-H}$=8.6 Hz and $J_{C-4-H,C-2-H}$=2.7 Hz, C-2-H), 7.21 (1H, d, $J_{C-2-H,C-1-H}$=8.6 Hz, C-1-H) and 7.32-7.45 (5H, m, $C_6H_5$); $\delta_C$ ($CDCl_3$, 100.4 MHz) 16.64 (q, C-18), 25.58 (t), 25.83 (t), 26.98 (q, C-1'), 29.73 (t), 33.50 (t), 33.83 (t), 38.55 (d), 40.42 (d), 41.53 (s, C-13), 42.57 (d), 69.95 (t, $OCR_2Ar$), 112.56 (d), 114.51 (d), 126.14 (d), 126.29 (2×d), 127.75 (d), 128.42

(2×d), 131.49 (s), 137.01 (s), 137.16 (s), 156.82 (s, C-3), 171.81 (s, C=O) and 178.68 (s, C=O); MS m/z (FAB+) 404.4 [79, (M+H)$^+$], 91.1 [100, (CH$_2$Ar)$^+$]; Acc MS m/z (FAB+) 404.22174, C$_{26}$H$_{30}$NO$_3$ requires 404.22257. For HPLC and CHN analysis, a sample was recrystallized from EtOH to give colourless crystals. HPLC (methanol/water, 90:10; $\lambda_{max}$=278.1 nm) Rt=3.93 min, 100%. Found: C, 77.30; H, 7.22; N, 3.48. C$_{26}$H$_{29}$NO$_3$ requires: C, 77.39; H, 7.24; N, 3.47.

3-Benzyloxy-N-ethyl-16,17-seco-estra-1,3,5(10)-triene-16,17-imide (12)

Following the alkylation conditions (see VI-1-3), 10 (500 mg, 1.28 mmol) was treated with NaH (62 mg, 1.54 mmol) and the subsequent reaction with ethyl iodide (205 μL, 2.57 mmol) was complete within 1 hour. Fractionation of the crude product that obtained by flash chromatography with chloroform as eluent gave 12 as a white residue (502 mg, 94%): mp 93-95° C.; IR (KBr) 2975-2865 (aliph CH), 1715 (C=O), 1665 (C=O), 1605-1500 (arom C=C) cm$^{-1}$; $\delta_H$ (CDCl$_3$, 400 MHz) 1.11 (3H, t, J=7.2 Hz, C-2'-H$_3$), 1.16 (3H, s, C-18-H$_3$), 1.31-2.98 (11H, m), 2.85-2.90 (2H, m, C-6-H$_2$), 3.81 (2H, m, N—CH$_2$), 5.04 (2H, s, OCH$_2$Ar), 6.72 (1H, d, J$_{C-2-H,C-4-H}$=2.7 Hz, C-4-H), 6.81 (1H, dd, J$_{C-1-H,C-2-H}$=8.6 Hz and J$_{C-4-H,C-2-H}$=2.7 Hz, C-2-H), 7.22 (1H, d, J$_{C-2-H,C-1-H}$=8.6 Hz, C-1-H) and 7.30-7.44 (5H, m, C$_6$H$_5$); $\delta_C$ (CDCl$_3$, 100.4 MHz) 13.15 (q, C-2'), 16.43 (q, C-18), 25.49 (t), 25.69 (t), 29.61 (t), 33.52 (t), 33.63 (t), 35.03 (t, C-1'), 38.54 (d), 40.22 (d), 41.28 (s, C-13), 42.42 (d), 69.84 (t, OCH$_2$Ar), 112.44 (d), 114.41 (d), 126.00 (d), 127.15 (2×d), 127.61 (d), 128.28 (2×d), 131.41 (s), 136.91 (s), 137.05 (s), 156.70 (s, C-3), 171.15 (s, C=O) and 178.03 (s, C=O); MS m/z (FAB+) 418.3 [90, (M+H)$^+$], 91.0 [100, (CH$_2$Ar)+]; Acc MS m/z (FAB+) 417.23061, C$_{27}$H$_{31}$NO$_3$ requires 417.23039. For HPLC and CHN analysis, a sample was recrystallized from EtOH to give white crystals. HPLC (methanol/water, 85:15; $\lambda_{max}$=278.1 nm) Rt=8.15 min, 100%. Found: C,; H,; N, C$_{27}$H$_{31}$NO$_3$ requires: C, 77.67; H, 7.48; N, 3.35.

3-Benzyloxy-N-propyl-16,17-seco-estra-1,3,5(10)-triene-16,17-imide (13)

Following the alkylation conditions (see VI-1-3), 10 (500 mg, 1.28 mmol) was treated with NaH (62 mg, 1.54 mmol) and the subsequent reaction with propyl iodide (250 μL, 2.57 mmol) was complete within 2 hours. Fractionation of the crude product that obtained by flash chromatography with chloroform as eluent gave 13 as a white residue (524 mg, 94%): mp 95-98° C.; IR (KBr) 3035 (arom CH), 2960-2870 (aliph CH), 1720 (C=O), 1660 (C=O), 1610-1500 (arom C=C) cm$^{-1}$; $\delta_H$ (CDCl$_3$, 400 MHz) 0.89 (3H, t, J=7.6 Hz, C-3'-H$_3$), 1.16 (3H, s, C-18-H$_3$), 1.32-2.98 (13H, m), 2.83-2.88 (2H, m, C-6-H$_2$), 3.64-3.80 (2H, m, N—CH$_2$), 5.03 (2H, s, OCH$_2$Ar), 6.72 (1H, d, J$_{C-2-H,C-4-H}$=2.7 Hz, C-4-H), 6.80 (1H, dd, J$_{C-1-H,C-2-H}$=8.6 Hz and J$_{C-4-H,C-2-H}$=2.7 Hz, C-2-H), 7.21 (1H, d, J$_{C-2-H,C-1-H}$8.6 Hz, C-1-H) and 7.30-7.44 (5H, m, C$_6$H$_5$); $\delta_C$ (CDCl$_3$, 100.4 MHz) 11.44 (q, C-3'), 16.65 (q, C-18), 21.30 (t), 25.63 (t), 25.83 (t), 29.76 (t), 33.68 (t), 33.81 (t), 38.68 (d), 40.37 (d), 41.50 (s, C-13), 41.56 (t, C-1'), 42.54 (d), 69.97 (t, OCH$_2$Ar), 112.56 (d), 114.52 (d), 126.15 (d), 127.29 (2×d), 127.76 (d), 128.42 (2×d), 131.54 (s), 137.03 (s), 137.20 (s), 156.83 (s, C-3), 171.49 (s, C=O) and 178.43 (s, C=O); MS m/z (FAB+) 432.4 [88, (M+H)$^+$], 91.1 [100, (CH$_2$Ar)$^+$]; Acc MS m/z (FAB+) 432.25223, C$_{28}$H$_{34}$NO$_3$ requires 432.25387. For HPLC and CHN analysis, a sample was recrystallized from EtOH to give white crystals. HPLC (methanol/water, 90:10; $\lambda_{max}$=278.1 nm) Rt=5.50 min, 100%. Found: C, 77.60; H, 7.68; N, 3.26. C$_{28}$H$_{33}$NO$_3$ requires: C, 77.93; H, 7.71; N, 3.25.

3-Benzyloxy-N-butyl-16,17-seco-estra-1,3,5(10)-triene-16,17-imide (14)

Following the alkylation conditions (see VI-1-3), 10 (500 mg, 1.28 mmol) was treated with NaH (62 mg, 1.54 mmol) and the subsequent reaction with bromobutane (276 μL, 2.57 mmol) was complete within 4 hours. Fractionation of the crude product that obtained by flash chromatography with chloroform as eluent gave 14 as a white residue (513 mg, 90%): mp 100-103° C.; IR (KBr) 2960-2870 (aliph CH), 1720 (C=O), 1665 (C=O), 1615-1500 (arom C=C) cm$^{-1}$; $\delta_H$ (CDCl$_3$, 400 MHz) 0.92 (3H, t, J=7.2 Hz, C-4'-H$_3$), 1.16 (3H, s, C-18-H$_3$), 1.28-2.99 (15H, m), 2.84-2.89 (2H, m, C-6-H$_2$), 3.75 (2H, m, N—CH$_2$), 5.04 (2H, s, OCH$_2$Ar), 6.72 (1H, d, J$_{C-2-H,C-4-H}$=2.3 Hz, C-4-H), 6.81 (1H, dd, J$_{C-1-H,C-2-H}$=8.6 Hz and J$_{C-4-H,C-2-H}$=2.7 Hz, C-2-H), 7.22 (1H, d, J$_{C-2-H,C-1-H}$=8.6 Hz, C-1-H) and 7.29-7.45 (5H, m, C$_6$H$_5$); $\delta_C$ (CDCl$_3$, 100.4 MHz) 13.76 (q, C-4'), 16.48 (q, C-18), 20.15 (t), 25.49 (t), 25.69 (t), 29.60 (t), 30.01 (t), 33.54 (t), 33.67 (t), 38.54 (d), 39.75 (t, C-1'), 40.24 (d), 41.35 (s, C-13), 42.40 (d), 69.83 (t, OCH$_2$Ar), 112.42 (d), 114.40 (d), 126.00 (d), 127.14 (2×d), 127.60 (d), 128.28 (2×d), 131.41 (s), 136.90 (s), 137.05 (s), 156.69 (s, C-3), 171.30 (s, C=O) and 178.25 (s, C=O); MS mti/z (FAB+) 446.3 [97, (M+H)$^+$], 91.0 [100, (CH$_2$Ar)$^+$]; Acc MS m/z (FAB+) 446.26912, C$_{29}$H$_{36}$NO$_3$ requires 446.26952. For HPLC and CHN analysis, a sample was recrystallized from EtOH to give white needles. HPLC (methanol/water, 85:15; $\lambda_{max}$=278.1 nm) Rt=8.15 min, 100%. Found: C, 77.80; H, 7.89; N, 3.13. C$_{29}$H$_{35}$NO$_3$ requires: C, 78.17; H, 7.92; N, 3.14. (slightly out)

3-Benzyloxy-N-pentyl-16,17-seco-estra-1,3,5(10)-triene-16,17-imide (15)

Following the alkylation conditions (see VI-1-3), 10 (500 mg, 1.28 mmol) was treated with NaH (62 mg, 1.54 mmol) and the subsequent reaction with pentyl bromide (318 μL, 2.57 mmol) was complete within 5 hours. Fractionation of the crude product that obtained by flash chromatography with chloroform as eluent gave 15 as a white residue (550 mg, 93%): mp 104-107° C.; IR (KBr) 3100-3000 (arom CH), 2960-2870 (aliph CH), 1720 (C=O), 1660 (C=O), 1610-1500 (arom C=C) cm$^{-1}$; $\delta_H$ (CDCl$_3$, 400 MHz) 0.89 (3H, t, J=7.2 Hz, C-5'-H$_3$), 1.16 (3H, s, C-18-H$_3$), 1.20-2.98 (17H, m), 2.83-2.89 (2H, m, C-6-H$_2$), 3.66-3.82 (2H, m, N—CH$_2$), 5.03 (2H, s, OCH$_2$Ar), 6.72 (1H, d, J$_{C-2-H,C-4-H}$=2.7 Hz, C-4-H), 6.80 (1H, dd, J$_{C-1-H,C-2-H}$=8.6 Hz and J$_{C-4-H,C-2-H}$=2.7 Hz, C-2-H), 7.21 (1H, d, J$_{C-2-H,C-1-H}$=8.6 Hz, C-1-H) and 7.30-7.44 (5H, m, C$_6$H$_5$); $\delta_C$ (CDCl$_3$, 100.4 MHz) 14.10 (q, C-5'), 16.63 (q, C-18), 22.46 (t), 25.63 (t), 25.81 (t), 27.72 (t), 29.16 (t), 27.75 (t), 33.68 (t), 33.79 (t), 38.68 (d), 40.10 (t, C-1'), 40.35 (d), 41.48 (s, C-13), 42.54 (d), 69.96 (t, OCH$_2$Ar), 112.55 (d), 114.51 (d), 126.15 (d), 127.29 (2×d), 127.76 (d), 128.42 (2×d), 131.54 (s), 137.02 (s), 137.20 (s), 156.81 (s, C-3), 171.45 (s, C=O) and 178.39 (s, C=O); MS m/z (FAB+) 460.2 [78, (M+H)$^+$], 91.1 [100, (CH$_2$Ar)$^+$]; Acc MS m/z (FAB+) 460.28447, C$_{30}$H$_{38}$NO$_3$ requires 460.28517. For HPLC and CHN analysis, a sample was recrystallized from EtOH to give colourless needles. HPLC (methanol/water, 92:8; $\lambda_{max}$=276.9 nm) Rt=6.46 min, 97.7%. Found: C, 78.20; H, 8.08; N, 3.01. C$_{30}$H$_{37}$NO$_3$ requires: C, 78.40; H, 8.11; N, 3.05.

3-Benzyloxy-N-hexyl-16,17-seco-estra-1,3,5(10)-triene-16,17-imide (16)

Following the alkylation conditions (see VI-1-3), 10 (500 mg, 1.28 mmol) was treated with NaH (62 mg, 1.54 mmol) and the subsequent reaction with hexyl bromide (360 µL, 2.57 mmol) was complete within 1.5 hours. Fractionation of the crude product that obtained by flash chromatography with chloroform as eluent gave 16 as a white residue (575 mg, 94%): mp 108-111° C.; IR (KBr) 2960-2860 (aliph CH), 1720 (C=O), 1665 (C=O), 1615-1500 (arom C=C) cm$^{-1}$; $\delta_H$ (CDCl$_3$, 400 MHz) 0.87 (3H, t, J=6.6 Hz, C-6'-H$_3$), 1.16 (3H, s, C-18-H$_3$), 1.28-2.98 (19H, m), 2.84-2.89 (2H, m, C-6-H$_2$), 3.74 (2H, m, N—CH$_2$), 5.04 (2H, s, OCH$_2$Ar), 6.72 (1H, d, $J_{C-2-H,C-4-H}$=2.7 Hz, C-4-H), 6.81 (1H, dd, $J_{C-1-H,C-2-H}$=8.6 Hz and $J_{C-4-H,C-2-H}$=2.7 Hz, C-2-H), 7.22 (1H, d, $J_{C-2-H,C-1-H}$=8.6 Hz, C-1-H) and 7.29-7.44 (5H, m, C$_6$H$_5$); 6 (CDCl$_3$, 100.4 MHz) 14.13 (q, C-6'), 16.63 (q, C-18), 22.63 (t), 25.64 (t), 25.84 (t), 26.69 (t), 27.99 (t), 29.76 (t), 31.56 (t), 33.69 (t), 33.82 (t), 38.70 (d), 40.14 (t, C-1'), 40.39 (d), 41.50 (s, C-13), 42.55 (d), 69.99 (t, OCH$_2$Ar), (d), 114.55 (d), 126.15 (d), 127.29 (2×d), 127.76 (d), 128.42 (2×d), 131.57 (s), (s), 137.20 (s), 156.84 (s, C-3), 171.44 (s, C=O) and 178.38 (s, C=O); MS m/z (FAB+) 474.3 [68, (M+H)$^+$], 91.0 [100, (CH$_2$Ar)$^+$]; Acc MS m/z (FAB+) 473.29238, C$_{31}$H$_{39}$NO$_3$ requires 473.29299. For HPLC and CHN analysis, a sample was recrystallized from EtOH to give white needles. HPLC (methanol/water, 85:15; $\lambda_{max}$=278.1 nm) Rt=8.15 min, 100%. Found: C, 78.10; H, 8.16; N, 2.98. C$_{31}$H$_{39}$NO$_3$ requires: C, 78.61; H, 8.30; N, 2.96. (slightly out)

3-Benzyloxy-N-bromobutyl-16,17-seco-estra-1,3,5(10)-triene-16,17-imide (17)

Following the alkylation conditions (see VI-1-3), 10 (500 mg, 1.28 mmol) was treated with NaH (62 mg, 1.54 mmol) and the subsequent reaction with 1,4-dibromobutane (310 µL, 2.57 mmol) was complete within 1.5 hours. Fractionation of the crude product that obtained by flash chromatography with chloroform as eluent gave 17 as a white residue (569 mg, 84%): mp 113-116° C.; IR (KBr) 2935-2860 (aliph CH), 1720 (C=O), 1670 (C=O), 1605-1500 (arom C=C) cm$^{-1}$; $\delta_H$ (CDCl$_3$, 400 MHz) 1.17 (3H, s, C-18-H3), 1.30-3.00 (15H, m), 2.84-2.90 (2H, m, C-6-H$_2$), 3.42 (2H, t, J=6.8 Hz, CH$_2$Br), 3.79 (2H, m, N—CH$_2$), 5.04 (2H, s, OCH$_2$Ar), 6.72 (1H, d, $J_{C-2-H,C-4-H}$=2.7 Hz, C-4-H), 6.81 (1H, dd, $J_{C-1-H,C-2-H}$=8.6 Hz and $J_{C-4-H,C-2-H}$=2.7 Hz, C-2-H), 7.21 (1H, d, $J_{C-2-H,C-1-H}$=8.6 Hz, C-1-H) and 7.30-7.45 (5H, m, C$_6$H$_5$); $\delta_C$ (CDCl$_3$, 100.4 MHz) 17.02 (q, C-18), 25.92 (t), 26.14 (t), 27.12 (t), 30.08 (t), 30.51 (t), 33.54 (t), 33.95 (t), 34.08 (t), 38.96 (d), 39.35 (t, C-1'), 40.62 (t), 41.85 (s, C-13), 42.85 (d), 70.27 (t, OCH$_2$Ar), 112.88 (d), 114.83 (d), (d), 127.64 (2×d), 128.12 (d), 128.77 (2×d), 131.77 (s), 137.30 (s), 137.50 (s), (s, C-3), 171.83 (s, C=O) and 178.76 (s, C=O); MS m/z (FAB+) 524.1 [42, (M+H)$^+$], 91.0 [100, (CH$_2$Ar)$^+$]; Acc MS m/z (FAB+) 525.17157, C$_{29}$H$_{34}$$^{81}$BrNO$_3$ requires 525.17016 and 524.17384, C$_{29}$H$_{34}$BrNO$_3$ requires 524.18003. For HPLC and CHN analysis, a sample was recrystallized from EtOH to give white crystals. HPLC (methanol/water, 90:10; $\lambda_{max}$=278.1 nm) Rt=6.04 min, 99.7%. Found: C, 66.30; H, 6.51; N, 2.56. C$_{29}$H$_{34}$BrNO$_3$ requires: C, 66.41; H, 6.53; N, 2.67.

3-Benzyloxy-N-cyclopropylmethyl-16,17-seco-estra-1,3,5(10)-triene-16,17-imide (18)

Following the alkylation conditions (see VI-1-3), 10 (500 mg, 1.28 mmol) was treated with NaH (62 mg, 1.54 mmol) and the subsequent reaction with bromomethyl-cyclopropane (246 µL, 2.57 mmol) was complete within 3 hours. Fractionation of the crude product that obtained by flash chromatography with chloroform as eluent gave 18 as a white residue (536 mg, 94%): mp 96-99° C.; IR (KBr) 2920-2860 (aliph CH), 1720(C=O), 1670(C=O), 1610-1495 (arom C=C) cm$^{-1}$; $\delta_H$ (CDCl$_3$, 400 MHz) 0.29-0.34 (2H, m, C-3'-H$_2$), 0.40-0.45 (2H, m, C-4'-H$_2$), 1.15 (1H, m, C-2'-H), 1.18 (3H, s, C-18-H$_3$), 1.25-3.01 (11H, m), 2.85-2.90 (2H, m, C-6-H$_2$), 3.67 (2H, m, N—CH$_2$), 5.04 (2H, s, OCH$_2$Ar), 6.73 (1H, d, $J_{C-2-H,C-4-H}$=2.3 Hz, C-4-H), 6.81 (1H, dd, $J_{C-1-H,C-2-H}$=8.6 Hz and $J_{C-4-H,C-2-H}$=2.7 Hz, C-2-H), 7.22 (1H, d, $J_{C-2-H,C-1-H}$=8.6 Hz, C-1-H) and 7.29-7.45 (5H, m, C$_6$H$_5$); $\delta_C$ (CDCl$_3$, 100.4 MHz) 3.94 (t, C-3'), 4.02 (t, C-4'), 10.52 (d, C-2'), 16.96 (q, C-18), 25.96 (t), 26.15 (t), 30.08 (t), 34.03 (t), 34.14 (t), 39.06 (d), 40.65 (d), 41.86 (s, C-13), 42.86 (d), 44.59 (t, C-1'), 70.31 (t, OCH$_2$Ar), 112.90 (d), 114.87 (d), 126.45 (d), 127.60 (2×d), 128.06 (d), 128.73 (2×d), 131.91 (s), 137.37 (s), 137.52 (s), 157.16 (s, C-3), 171.99 (s, C=O) and 178.98 (s, C=O); MS m/z (FAB+) 887.3 [58, (2M+H)$^+$], 444.1 [98, (M+H)$^+$], 91.0 [100, (CH$_2$Ar)+]; Ace MS m/z (FAB+) 443.24533, C$_{29}$H$_{33}$NO$_3$ requires 443.24604. For HPLC and CHN analysis, a sample was recrystallized from EtOH to give white needles. HPLC (methanol/water, 85:15; $\lambda_{max}$=278.1 nm) Rt=8.15 min, 100%. Found: C, 78.30; H, 7.47; N, 3.18. C$_{29}$H$_{33}$NO$_3$ requires: C, 78.52; H, 7.50; N, 3.16.

3-Benzyloxy-N-(3-picolyl)-16,17-seco-estra-1,3,5(10)-triene-16,17-imide (19)

Sodium hydride (60% dispersion in mineral oil, 31 mg, 770 µmol) was added to a stirred solution of 10 (250 mg, 642 µmol) in anhydrous DMF (10 mL) at room temperature under an atmosphere of N$_2$. After evolution of hydrogen had ceased, 3-(Bromomethyl)pyridine hydrobromide (325 mg, 1.28 mmol) was added to give a deep orange mixture. This was stirred for 2 hours at room temperature, then an additional 2 equivalents of sodium hydride (52 mg, 1.28 mmol) were added to the mixture. This was stirred overnight at room temperature and poured into water (40 mL). The resulting dark red mixture was extracted into ethyl acetate (40 mL). After further exhaustive washing with brine (4×20 mL), the organic layer was dried (MgSO$_4$), filtered and evaporated in vacuo. Fractionation of the crude product that obtained by flash chromatography with chloroform/acetone (9:1) as eluent gave 19 as a white residue which was further purified by a second flash column with chloroform/acetone (95:5). A white powder was obtained (230 mg, 75%): mp 170-172° C.; IR (KBr) 2925-2870 (aliph CH), 1720 (C=O), 1670 (C=O), 1610-1500 (arom C=C) cm$^{-1}$; $\delta_H$ (CDCl$_3$, 400 MHz) 1.14 (3H, s, C-18-H$_3$), 1.28-3.04 (1H, m), 2.84-2.88 (2H, m, C-6-H$_2$), 4.92 (1H, d, $J_{BA}$=13.7 Hz, N—CH$_A$H$_B$Py), 4.98 (1H, d, $J_{AB}$=14.1 Hz, N—CH$_A$H$_B$Py), 5.03 (2H, s, OCH$_2$Ar), 6.71 (1H, d, $J_{C-2-H,C-4-H}$=2.7 Hz, C-4-H), 6.79 (1H, dd, $J_{C-1-H,C-2-H}$=8.6 Hz and $J_{C-4-H,C-2-H}$=2.7 Hz, C-2-H), 7.17-7.45 (7H, m, C$_6$H$_5$, C-1-H and C-4"-H), 7.69 (1H, td, $J_{C-4"-H, C-3"-H}$=7.8 Hz, $J_{C-5"-H, C-3"-H}$=$J_{C-1"-H,C-3"-H}$=1.9 Hz, C-2"-H), 8.50 (1H, dd, $J_{C-4"-H, C-5"-H}$=5.1 Hz, $J_{C-3"-H, C-5"-H}$=1.6 Hz, C-5"-H) and 8.63 (1H, d, $J_{C-3"-H, C-1"-H}$=1.9 Hz, C-1"-H); $\delta_C$ (CDCl$_3$, 100.4 MHz) 16.49 (q, C-18), 25.51 (t), 25.77 (t), 29.68 (t), 33.56 (t), 33.66 (t), 38.52 (d), 40.14 (d), 40.85 (t, C-1'), 41.58 (s, C-13), 42.43 (d), 69.93 (t, —OCH$_2$Ar), 112.55 (d), 114.47 (d), 123.19 (d), 126.12 (d), 127.26 (2×d), 127.75 (d), 128.41 (2×d), 131.35 (s), 132.80 (s), 136.37 (d), 137.10 (2×s), 148.59 (d), 150.03 (d), 156.80 (s, C-3), 171.36 (s, C=O) and 178.31 (s, C=O); MS m/z (FAB+) 481.3 [100, (M+H)$^+$], 91.1 [47, (CH$_2$Ar)$^+$]; Acc MS m/z (FAB+) 481.25036, C$_{31}$H$_{33}$N$_2$O$_3$ requires 481.24912. For HPLC and CHN analysis, a sample was recrystallized from EtOH to give colourless needles. HPLC (methanol/water, 90:10; $\lambda_{max}$=259.2 nm) Rt=3.90 min, 100%. Found: C, 77.00; H, 6.75; N, 5.73. C$_{32}$H$_{33}$N$_2$O$_3$ requires: C, 77.47; H, 6.71; N, 5.83.

3-Benzyloxy-N-tert-butyl-benzyl-16,17-seco-estra-1,3,5(10)-triene-16,17-imide (20)

Following the alkylation conditions (see VI-1-3), 10 (500 mg, 1.28 mmol) was treated with NaH (62 mg, 1.54 mmol) and the subsequent reaction with 1-bromomethyl-4-tert-butyl-benzene (472 μL, 2.57 mmol) was complete within 30 minutes. Fractionation of the crude product that obtained by flash chromatography with chloroform as eluent gave 20 as a white residue (667 mg, 97%): mp 199-200° C.; IR (KBr) 2965-2870 (aliph CH), 1720 (C=O), 1670 (C=O), 1605-1505 (arom C=C) cm$^{-1}$; $\delta_H$ (CDCl$_3$, 400 MHz) 1.16 (3H, s, C-18-H$_3$), 1.28 (9H, s, C(CH$_3$)$_3$), 1.30-3.01 (11H, m), 2.84-2.90 (2H, m, C-6-H$_2$), 4.88 (1H, d, $J_{BA}$=13.7 Hz, N—CH$_A$CH$_B$), 4.94 (1H, d, $J_{AB}$=14.1 Hz, N—CH$_A$CH$_B$), 5.03 (2H, s, OCH$_2$Ar), 6.72 (1H, d, $J_{C-2-H,C-4-H}$=2.7 Hz, C-4-H), 6.80 (1H, dd, $J_{C-1-H,C-2-H}$=8.6 Hz and $J_{C-4-H,C-2-H}$=2.7 Hz, C-2-H), 7.21 (1H, d, $J_{C-2-H,C-1-H}$=8.6 Hz, C-1-H) and 7.24-7.44 (9H, m, C$_6$H$_5$, C-2"-H, C-3"-H, C-5"-H and C-6"-H); $\delta_C$ (CDCl$_3$, 100.4 MHz) 16.60 (q, C-18), 25.60 (t), 25.79 (t), 29.73 (t), 31.40 (3×q, C(CH$_3$)$_3$), 33.67 (t), 33.77 (t), 34.53 (s, C(CH$_3$)$_3$), 38.63 (d), 40.15 (d), 41.55 (s, C-13), 42.48 (d), 42.88 (t, C-1'), 69.93 (t, OCH$_2$Ar), 112.53 (d), 114.47 (d), 125.20 (2×d), 126.15 (d), 127.30 (2×d), 127.77 (d), 128.02 (2×d), 128.42 (2×d), 131.48 (s), 134.20 (s), 136.98 (s), 137.17 (s), 149.91 (s), 156.79 (s, C-3), 171.42 (s, C=O) and 178.37 (s, C=O); MS m/z (FAB+) 1071.5 [32, (2M+H)$^+$], 536.2 [80, (M+H)$^+$], 91.0 [100, (CH$_2$Ar)$^+$]; MS m/z (FAB−) 534.3 [72, (M−H)-], 195.0 [100], 276.0 [100] Acc MS m/z (FAB+) 535.30865, C$_{36}$H$_{41}$NO$_3$ requires 535.30864. For HPLC and CHN analysis, a sample was recrystallized from EtOH to give white needles. HPLC (methanol/water, 90:10; $\lambda_{max}$=259.2 nm) Rt=3.90 min, 100%.

Found: C,; H,; N, C$_{29}$H$_{35}$NO$_3$ requires: C, 80.71; H, 7.71; N, 2.61.

3-Benzyloxy-N-benzyl-16,17-seco-estra-1,3,5(10)-triene-16,17-imide (21)

3-Benzyl-marrianolic acid (9) (500 mg, 1.22 mmol) was stirred with benzylamine (6.25 mL, 57.22 mmol) and heated at 180° C. under an atmosphere of N$_2$ for 3 hours. After cooling down, the resulting brown mixture was poured into water (250 mL), acidified with HCl 5M, and the organic fractions were extracted into ethyl acetate (50 mL). After further exhaustive washing with water (1×25 mL), then brine (3×25 mL), the organic layer was dried (MgSO$_4$), filtered and evaporated in vacuo. Fractionation of the crude product that obtained by flash chromatography with chloroform/hexane (8/2) as eluent gave 21 as a creamy powder (385 mg, 65%): mp 144-146° C.; IR (KBr) 3100 (arom CH), 2940-2850 (aliph CH), 1720 (C=O), 1670 (C=O), 1615-1560 (arom C=C) cm$^{-1}$; $\delta_H$ (CDCl$_3$, 400 MHz) 1.15 (3H, s, C-18-H$_3$), 1.25-3.01 (11H, m), 2.84-2.89 (2H, m, C-6-H$_2$), 4.91 (1H, d, $J_{BA}$=13.7 Hz, N—CH$_A$H$_B$Ar), 4.98 (1H, d, $J_{AB}$=13.7 Hz, N—CH$_A$H$_B$Ar), 5.03 (2H, s, OCH$_2$Ar), 6.72 (1H, d, $J_{C-2-H,C-4-H}$=2.7 Hz, C-4-H), 6.80 (1H, dd, $J_{C-1-H,C-2-H}$=8.6 Hz and $J_{C-4-H,C-2-H}$=2.7 Hz, C-2-H), 7.21 (1H, d, $J_{C-2-H,C-1-H}$=8.2 Hz, C-1-H) and 7.24-7.43 (10H, m, 2×C$_6$H$_5$); $\delta_C$ (CDCl$_3$, 100.4 MHz) 16.54 (q, C-18), 25.59 (t), 25.80 (t), 29.73 (t), 33.66 (t), 33.75 (t), 38.64 (d), 40.17 (d), 41.54 (s, C-13), 42.48 (d), 43.22 (t, C-1'), 69.93 (t, OCH$_2$Ar), 112.54 (d), 114.48 (d), 126.14 (d), 127.19 (d), 127.29 (d), 127.76 (d), 128.27 (d), 128.39 (d), 128.42 (d), 131.47 (s), 136.98 (s), 137.16 (s), 137.25 (s), 156.80 (s, C-3), 171.39 (s, C=O) and 178.31 (s, C=O); MS m/z (FAB+) 480.2 [52, (M+H)$^+$], 91.1 [100, (CH$_2$Ar)$^+$]; Acc MS m/z (FAB+) 480.25223, C$_{32}$H$_{34}$NO$_3$ requires 480.25387. For HPLC and CHN analysis, a sample was recrystallized from MeOH to give colourless needles. HPLC (methanol/water, 90:10; $\lambda_{max}$=220.0 nm) Rt=5.83 min, 99.0%. Found: C, 80.10; H, 6.91; N, 2.94. C$_{32}$H$_{33}$NO$_3$ requires: C, 80.14; H, 6.94; N, 2.92.

2-3—Deprotection of the Precursors

3-Hydroxy-16,17-seco-estra-1,3,5(10)-triene-16,17-imide (5) (STX 187)

Following the hydrogenation conditions (see 1-4), a suspension of 10 (350 mg, 899 μmol) and Pd—C (10%, 100 mg) in MeOH/THF 1:1 (50 mL) was hydrogenated for 5 hours to give 5 as a white solid (246 mg, 91%). An analytical sample was recrystallized from CHCl$_3$/Hexane 2:1 to give white crystals: mp 297-300° C.; TLC (chloroform/acetone, 8:2) R$_f$ 0.39 cf. R$_f$ 0.58 (10); IR (KBr) 3410 (OH), 3180-3085 (arom CH), 2955-2870 (aliph CH), 1715 (C=O), 1680 (C=O), 1615-1500 (arom C=C) cm$^{-1}$; $\delta_H$ (DMSO-d$_6$, 400 MHz) 1.09 (3H, s, C-18-H3), 1.15-2.66 (11H, m), 2.69-2.73 (2H, m, C-6-H$_2$), 6.44 (1H, d, $J_{C-2-H,C-4-H}$=2.7 Hz, C-4-H), 6.52 (1H, dd, $J_{C-1-H,C-2-H}$=8.4 Hz and $J_{C-4-H,C-2-H}$=2.7 Hz, C-2-H), 7.07 (1H, d, $J_{C-2-H,C-1-H}$=8.6 Hz, C-1-H), 9.05 (1H, s, exchanged with D$_2$O, OH) and 10.63 (1H, s, exchanged with D$_2$O, NH); $\delta_C$ (DMSO-d$_6$, 100.4 MHz) 16.21 (q, C-18), 25.17 (t), 25.38 (t), 29.19 (t), 32.40 (t), 32.77 (t), 38.00 (d), 40.36 (d), 40.53 (s, C-13), 41.45 (d), 112.74 (d), 114.51 (d), 125.88 (d), 129.48 (s), 136.71 (s), 154.81 (s, C-3), 172.16 (s, C=O) and 178.97 (s, C=O); MS m/z (FAB+) 453.1 [17, (M+H+NBA)$^+$], 300.0 [100, (M+H)$^+$], 213.1 [16], 159.1 [20], 133.0 [29], 111.1 [36], 97.1 [60]; MS m/z (FAB−) 605.4 [20, (M+2NBA)$^-$], 451.3 [58, (M−H+NBA)$^-$], 298.2 [100, (M−H)$^-$], 276.1 [21], 188.1 [25], 139.1 [19]; Acc MS m/z (FAB+) 300.15853, C$_{18}$H$_{22}$NO$_3$ requires 300.15997. HPLC (methanol/water, 60:40; $\lambda_{max}$=279.3 nm) Rt=3.06 min, 100%. Found: C, 61.80; H, 5.85; N, 3.86. C$_{18}$H$_{21}$NO$_3$+(CHCl$_3$)$_{1/2}$ requires: C, 61.88; H, 6.04; N, 3.90.

3-Hydroxy-N-methyl-16,17-seco-estra-1,3,5(10)-triene-16,17-imide (22) (STX 188)

Following the hydrogenation conditions (see VI-1-4), a suspension of 11 (400 mg, 992 μmol) and Pd—C (10%, 200 mg) in MeOH/THF 2:1 (30 mL) was hydrogenated for 2 hours to give 22 as a white solid (253 mg, 81%). An analytical sample was recrystallized from ethyl acetate to give white crystals: mp 328-330° C.; IR (KBr) 3460 (OH), 2940-2860 (aliph CH), 1715 (C=O), 1655 (C=O), 1610-1510 (arom C=C) cm$^{-1}$; $\delta_H$ (DMSO-d$_6$, 400 MHz) 1.09 (3H, s, C-18-H$_3$), 1.9-2.97 (11H, m), 2.68-2.73 (2H, m, C-6-H$_2$), 2.98 (3H, s, N—CH$_3$), 6.44 (1H, d, $J_{C-2-H,C-4-H}$=2.3 Hz, C-4-H), 6.52 (1H, dd, $J_{C-1-H,C-2-H}$=8.4 Hz and $J_{C-4-H,C-2-H}$=2.3 Hz, C-2-H), 7.06 (1H, d, $J_{C-2-H,C-1-H}$=8.6 Hz, C-1-H) and 9.05 (1H, s, exchanged with D$_2$O, OH); $\delta_C$ (DMSO-d$_6$, 100.4 MHz) δ 16.32 (q, C-18), 25.19 (t), 26.37 (q, C-1'), 29.11 (t), 32.78 (t), 33.55 (2xt), 37.83 (d), 40.90 (d), 41.86 (d), 112.71 (d), 114.50 (d), 125.81 (d), 129.40 (s), 136.68 (s), 154.80 (s, C-3), 171.35 (s, C=O) and 178.24 (s, C=O); MS m/z (FAB+) 314.1 [78, (M+H)+], 97.1 [100]; Acc MS m/z (FAB+) 314.17487, $C_{19}H_{24}NO_3$ requires 314.17562. HPLC (methanol/water, 70:30; $\lambda_{max}$=279.3 nm) Rt=3.24 min, 100%. Found: C, 72.60; H, 7.16; N, 4.35. $C_{19}H_{23}NO_3$ requires: C, 72.82; H, 7.40; N, 4.47.

*a*C-13 signal is hidden under the solvent peaks

3-Hydroxy-N-ethyl-16,17-seco-estra-1,3,5(10)-triene-16,17-imide (23) (STX 275)

Following the hydrogenation conditions (see VI-1-5), a suspension of 12 (470 mg, 1.13 mmol) and Pd—C (10%, 200 mg) in MeOH/THF 2:1 (30 mL) was hydrogenated for 4.5 hours to give 23 as a white solid (183 mg, 50%). This was washed in acetone to give a white powder (121 mg, 33%): mp 306-308° C.; IR (KBr) 3450 (OH), 2915-2860 (aliph CH), 1715 (C=O), 1655 (C=O), 1610-1505 (arom C=C) cm$^{-1}$; $\delta_H$ (CDCl$_3$, 400 MHz) 1.11 (3H, t, J=7.0 Hz, C-2'-H$_3$), 1.16 (3H, s, C-18-H$_3$), 1.22-2.98 (11H, m), 2.81-2.87 (2H, m, C-6-H$_2$), 3.82 (2H, m, N—CH$_2$), 4.62 (1H, s, exchanged with D$_2$O, OH), 6.57 (1H, d, $J_{C-2-H,C-4-H}$=2.7 Hz, C-4-H), 6.66 (1H, dd, $J_{C-1-H,C-2-H}$=8.6 Hz and $J_{C-4-H,C-2-H}$=2.7 Hz, C-2-H) and 7.17 (1H, d, $J_{C-2-H,C-1-H}$=8.6 Hz, C-1-H); MS m/z (FAB+) 328.2 [100, (M+H)+], 481.2 [13, (M+H+NBA)+]; Acc MS m/z (FAB+) 328.19062, $C_{20}H_{26}NO_3$ requires 328.19127. HPLC (methanol/water, 90:10; $\lambda_{max}$=259.2 nm) Rt=3.90 min, 100%.

Found: C, 72.90; H, 7.68; N, 4.09. $C_{20}H_{25}NO_3$ requires: C, 73.37; H, 7.70; N, 4.28. (slightly out)

3-Hydroxy-N-propyl-16,17-seco-estra-1,3,5(10)-triene-16,17-imide (24) (STX 189)

Following the hydrogenation conditions (see VI-1-5), a suspension of 13 (400 mg, 927 μmol) and Pd—C (10%, 100 mg) in MeOH/THF 2:1 (30 mL) was hydrogenated for 3 hours to give 24 as a white solid (256 mg, 81%). An analytical sample was recrystallized from methanol to give colourless crystals: mp 183-186° C.; IR (KBr) 3445 (OH), 3050 (arom CH), 2940-2860 (aliph CH), 1725 (C=O), 1655 (C=O), 1585-1500 (arom C=C) cm$^{-1}$; $\delta_H$ (CDCl$_3$, 400 MHz) 0.90 (3H, t, J=7.4 Hz, C-3'-H$_3$), 1.17 (3H, s, C-18-H$_3$), 1.30-2.98 (13H, m), 2.82-2.86 (2H, m, C-6-H$_2$), 3.64-3.80 (2H, m, N—CH$_2$), 4.73 (1H, s, exchanged with D$_2$O, OH), 6.58 (1H, d, $J_{C-2-H,C-4-H}$=2.7 Hz, C-4-H), 6.66 (1H, dd, $J_{C-1-H,C-2-H}$=8.6 Hz and $J_{C-4-H,C-2-H}$=2.7 Hz, C-2-H) and 7.17 (1H, d, $J_{C-2-H,C-1-H}$=8.6 Hz, C-1-H); $\delta_C$ (CDCl$_3$, 100.4 MHz) 11.43 (q, C-3'), 16.64 (q, C-18), 21.29 (t), 25.62 (d), 25.76 (t), 29.56 (t), 33.65 (t), 33.75 (t), 38.66 (d), 40.32 (d), 41.51 (s, C-13), 41.63 (t, C-1'), 42.48 (d), 112.97 (d), 114.98 (d), 126.30 (d), 131.15 (s), 137.39 (s), 153.66 (s, C-3), 171.76 (s, C=O) and 178.59 (s, C=O); MS m/z (FAB+) 342.3 [100, (M+H)+], 133.2 [17], 111.2 [23], 97.2 [45]; MS m/z (FAB−) 494.4 [43, (M+NBA)−], 340.3 [100, (M−H)−]; Acc MS 71/z (FAB+) 342.20756, $C_{21}H_{28}NO_3$ requires 342.20692. HPLC (methanol/water, 70:30; $\lambda_{max}$=279.3 nm) Rt=6.55 min, 100%. Found: C, 73.90; H, 7.98; N, 4.20. $C_{21}H_{27}NO_3$ requires: C, 73.87; H, 7.97; N, 4.10.

3-Hydroxy-N-butyl-16,17-seco-estra-1,3,5(10)-triene-16,17-imide (25) (STX 277)

Following the hydrogenation conditions (see VI-1-5), a suspension of 14 (480 mg, 1.08 mmol) and Pd—C (10%, 200 mg) in MeOH/THF 2:1 (30 mL) was hydrogenated for 2 hours to give 25 as a white solid (361 mg, 94%). This was recrystallized from methanol to give colourless needles (193 mg, 50%) and a further crop of the product (49 mg) was obtained from the residue of the mother liquor upon recrystallization from methanol (overall yield 63%): mp 212-214° C.; IR (KBr) 3445 (OH), 2940-2870 (aliph CH), 1715 (C=O), 1655 (C=O), 1585-1500 (arom C=C) cm$^{-1}$; $\delta_H$ (CDCl$_3$, 400 MHz) 0.92 (3H, m, C-4'-H$_3$), 1.16 (3H, s, C-18-H$_3$), 1.26-2.99 (15H, m), 2.81-2.88 (2H, m, C-6-H$_2$), 3.75 (2H, m, N—CH$_2$), 4.75 (1H, s, exchanged with D$_2$O, OH), 6.58 (1H, d, $J_{C-2-H,C-4-H}$=2.7 Hz, C-4-H), 6.66 (1H, dd, $J_{C-1-H,C-2-H}$=8.6 Hz and $J_{C-4-H,C-2-H}$=2.7 Hz, C-2-H) and 7.17 (1H, d, $J_{C-2-H,C-1-H}$=8.6 Hz, C-1-H); 6 (CDCl$_3$, 100.4 MHz) 13.76 (q, C-4'), 16.49 (q, C-18), 20.15 (t), 25.51 (t), 25.66 (t), 29.43 (t), 30.01 (t), 33.54 (t), 33.66 (t), 38.57 (d), 39.83 (t, C-1'), 40.24 (d), 41.39 (s, C-13), 42.37 (d), 112.86 (d), 114.86 (d), 126.16 (d), 131.08 (s), 137.26 (s), 153.54 (s, C-3), 171.54 (s, C=O) and 178.40 (s, C=O); MS m/z (FAB+) 509.3 [5, (M+H+NBA)+], 356.2 [100, (M+H)+]; MS m/z (FAB−) 508.2 [35, (M+NBA)−], 354.2 [100, (M−H)−]; Ace MS m/z (FAB+) 356.22247, $C_{22}H_{30}NO_3$ requires 356.22257. HPLC (methanol/water, 90:10; $\lambda_{max}$=259.2 nm) Rt=3.90 min, 100%. Found: C, 74.20; H, 8.21; N, 3.88. $C_{22}H_{29}NO_3$ requires: C, 74.33; H, 8.22; N, 3.94.

3-Hydroxy-N-pentyl-16,17-seco-estra-1,3,5(10)-triene-16,17-imide (26) (STX 190)

Following the hydrogenation conditions (see VI-1-5), a suspension of 15 (520 mg, 1.13 mmol) and Pd—C (10%, 100 mg) in MeOH/THF 2:1 (30 mL) was hydrogenated for 3 hours to give 26 as a white solid (347 mg, 83%). An analytical sample was recrystallized from methanol to give white crystals: mp 181-184° C.; IR (KBr) 3445 (OH), 2955-2870 (aliph CH), 1715 (C=O), 1660 (C=O), 1610-1505 (arom C=C) cm$^{-1}$; $\delta_H$ (CDCl$_3$, 400 MHz) 0.89 (3H, t, J=7.4 Hz, C-5'-H$_3$), 1.16 (3H, s, C-18-H$_3$), 1.20-2.98 (17H, m), 2.81-2.86 (2H, m, C-6-H$_2$), 3.65-3.82 (2H, m, N—CH$_2$), 4.77-4.79 (1H, m, exchanged with D$_2$O, OH), 6.58 (1H, d, $J_{C-2-H,C-4-H}$=2.7 Hz, C-4-H), 6.65 (1H, dd, $J_{C-1-H,C-2-H}$=8.2 Hz and $J_{C-4-H,C-2-H}$=2.7 Hz, C-2-H) and 7.17 (1H, d, $J_{C-2-H,C-1-H}$=8.2 Hz, C-1-H); $\delta_C$ (CDCl$_3$, 100.4 MHz) 14.10 (q, C-5'), 16.63 (q, C-18), 22.46 (t), 25.64 (t), 25.77 (t), 27.71 (t), 29.15 (t), 29.75 (t), 33.66 (t), 33.76 (t), 38.67 (d), 40.16 (t, C-1'), 40.32 (d), 41.50 (s, C-13), 42.49 (d), 112.97 (d), 114.98 (d), 126.31 (d), 131.19 (s), 137.40 (s), 153.65 (s, C-3), 171.67 (s, C=O) and 178.52 (s, C=O); MS m/z (FAB+) 739.1 [50, (2M+H)+], 523.0 [20, (M+H+NBA)+], 370.1 [100, (M+H)+], 97.0 [15]; MS m/z (FAB−) 737.6 [20, (2M−H)−], 675.4 [8, (M+2NBA)−], 522.4 [30, (M+NBA)−], 368.3 [100, (M−H)−]; Acc MS m/z (FAB+) 370.23940, $C_{23}H_{32}NO_3$ requires 370.23822. HPLC (methanol/water, 80:20; $\lambda_{max}$=279.3 nm) Rt=5.42 min, 100%. Found: C, 74.90; H, 8.38; N, 3.73. $C_{23}H_{31}NO_3$ requires: C, 74.96; H, 8.46; N, 3.79.

3-Hydroxy-N-hexyl-16,17-seco-estra-1,3,5(10)-triene-16,17-imide (27) (STX 276)

Following the hydrogenation conditions (see VI-1-5), a suspension of 16 (540 mg, 1.14 mmol) and Pd—C (10%, 200 mg) in MeOH/THF 2:1 (45 mL) was hydrogenated for 3 hours to give 27 as a white solid (384 mg, 88%). This was recrystallized from methanol to give white crystals (218 mg, 50%) and a further crop of the product (45 mg) was obtained from the residue of the mother liquor upon recrystallization from methanol (overall yield 60%): mp 157-159° C.; IR (KBr) 3435 (OH), 2930-2865 (aliph CH), 1715 (C=O), 1660 (C=O), 1585-1500 (arom C=C) cm$^{-1}$; $\delta_H$ (CDCl$_3$, 400 MHz) 0.87 (3H, t, J=6.8 Hz, C-6'-H$_3$), 1.16 (3H, s, C-18-H$_3$), 1.23-2.98 (19H, m), 2.81-2.87 (2H, m, C-6-H$_2$), 3.74 (2H, m, N—CH$_2$), 4.68 (1H, s, exchanged with D$_2$O, OH), 6.58 (1H, d, $J_{C\text{-}2\text{-}H,C\text{-}4\text{-}H}$=2.3 Hz, C-4-H), 6.66 (1H, dd, $J_{C\text{-}1\text{-}H,C\text{-}2\text{-}H}$=8.2 Hz and $J_{C\text{-}4\text{-}H,C\text{-}2\text{-}H}$=2.7 Hz, C-2-H) and 7.17 (1H, d, $J_{C\text{-}2\text{-}H,C\text{-}1\text{-}H}$=8.6 Hz, C-1-H); $\delta_C$ (CDCl$_3$, 100.4 MHz) 14.00 (q, C-6'), 16.48 (q, C-18), 22.48 (t), 25.46 (t), 25.59 (t), 26.53 (t), 27.82 (t), 29.41 (t), 31.39 (t), 33.49 (t), 33.58 (t), 38.48 (d), 40.06 (t, C-1'), 40.12 (d), 41.33 (s, C-13), 42.31 (d), 112.81 (d), 114.82 (d), 126.16 (d), 130.98 (s), 137.23 (s), 153.48 (s, C-3), 171.58 (s, C=O) and 178.40 (s, C=O); MS m/z (FAB+) 767.6 [48, (2M+H)$^+$], 384.3 [100, (M+H)$^+$]; MS m/z (FAB−) 765.5 [8, (2M−H)$^−$], 536.3 [10, (M+NBA)$^−$], 382.2 [100, (M−H)$^−$]; Ace MS m/z (FAB+) 384.25350, C$_{24}$H$_{34}$NO$_3$ requires 384.25387. HPLC (methanol/water, 90:10; $\lambda_{max}$=259.2 nm) Rt=3.90 min, 100%. Found: C, 75.40; H, 8.65; N, 3.71. C$_{24}$H$_{33}$NO$_3$ requires: C, 75.16; H, 8.67; N, 3.65.

3-Hydroxy-N-bromobutyl-16,17-seco-estra-1,3,5 (10)-triene-16,17-imide(28)(STX235)

Following the hydrogenation conditions (see VI-1-5), a suspension of 17 (210 mg, 381 μmol) and Pd—C (10%, 100 mg) in MeOH/THF 2:1 (30 mL) was hydrogenated for 2 hours to give 28 as a white solid (146 mg, 84%). This was recrystallized from methanol to give white crystals (98 mg, 57%): mp 165-167° C.; IR (KBr) 3450 (OH), 2910-2860 (aliph CH), 1715 (C=O), 1660 (C=O), 1610-1505 (arom C=C) cm$^{-1}$; $\delta_H$ (CDCl$_3$, 400 MHz) 1.18 (3H, s, C-18-H$_3$), 1.29-3.01 (15H, m), 2.82-2.88 (2H, m, C-6-H$_2$), 3.42 (2H, t, J=6.6 Hz, CH$_2$Br), 3.72-3.87 (2H, m, N—CH$_2$), 4.63 (1H, s, exchanged with D$_2$O, OH), 6.58 (1H, d, $J_{C\text{-}2\text{-}H,C\text{-}4\text{-}H}$=2.3 Hz, C-4-H), 6.66 (1H, dd, $J_{C\text{-}1\text{-}H,C\text{-}2\text{-}H}$=8.4 Hz and $J_{C\text{-}4\text{-}H,C\text{-}2\text{-}H}$=2.3 Hz, C-2-H) and 7.17 (1H, d, $J_{C\text{-}2\text{-}H,C\text{-}1\text{-}H}$=8.6 Hz, C-1-H); $\delta_C$ (DMSO-d$_6$, 100.4 MHz) 17.01 (q, C-18), 25.92 (t), 26.09 (t), 27.11 (t), 29.87 (t), 30.51 (t), 33.47 (t), 33.94 (t), 34.06 (t), 38.96 (d), 39.38 (t, C-1'), 40.62 (d), 41.86 (s, C-13), 42.80 (d), 113.29 (d), 115.28 (d), 126.62 (d), 131.53 (s), 137.73 (s), 153.87 (s, C-3), 171.93 (s, C=O) and 178.81 (s, C=O); MS m/z (FAB+) 869.2 [64], 587.1 [46, (M+H+NBA)$^+$], 434.1 [100, (M+H)$^+$]; Ace MS m/z (FAB+) 436.12874, C$_{22}$H$_{29}$$^{81}$BrNO$_3$ requires 436.13103 and 434.12822, C$_{22}$H$_{29}$BrNO$_3$ requires 434.13308. HPLC (methanol/water, 70:30; $\lambda_{max}$=279.3 nm) Rt=7.73 min, 98.3%. Found: C, 61.30; H, 6.60; N, 3.17. C$_{22}$H$_{28}$BrNO$_3$ requires: C, 60.83; H, 6.50; N, 3.22.

3-Hydroxy-N-cyclopropylmethyl-16,17-seco-estra-1, 3,5(10)-triene-16,17-imide (29) (STX 278)

Following the hydrogenation conditions (see VT-1-5), a suspension of 18 (500 mg, 1.13 mmol) and Pd—C (10%, 200 mg) in MeOH/THF 2:1 (45 mL) was hydrogenated for 2.5 hours to give 29 as a white solid (356 mg, 89%). This was recrystallized from methanol to give colourless crystals (181 mg, 45%) and a further crop of the product (73 mg) was obtained from the residue of the mother liquor upon recrystallization from methanol (overall yield 64%): mp 238-240° C.; IR (KBr) 3440 (OH), 2940-2865 (aliph CH), 1715 (C=O), 1655 (C=O), 1610-1505 (arom C=C) cm$^{-1}$; $\delta_H$ (CDCl$_3$, 400 MHz) 0.29-0.34 (2H, m, C-3'-H$_2$), 0.40-0.45 (2H, m, C-4'-H$_2$), 1.13 (1H, m, C-2'-H), 1.19 (3H, s, C-18-H$_3$), 1.30-3.02 (11H, m), 2.82-2.89 (2H, m, C-6-H$_2$), 3.66 (2H, m, N—CH$_2$), 4.70 (1H, s, exchanged with D$_2$O, OH), 6.58 (1H, d, $J_{C\text{-}2\text{-}H,C\text{-}4\text{-}H}$=2.7 Hz, C-4-H), 6.66 (1H, dd, $J_{C\text{-}1\text{-}H,C\text{-}2\text{-}H}$=8.2 Hz and $J_{C\text{-}4\text{-}H,C\text{-}2\text{-}H}$=2.7 Hz, C-2-H) and 7.17 (1H, d, $J_{C\text{-}2\text{-}H,C\text{-}1\text{-}H}$=8.6 Hz, C-1-H); $\delta_C$ (CDCl$_3$, 100.4 MHz) 3.95 (t, C-3'), 4.03 (t, C-4'), 10.51 (d, C-2'), 16.95 (q, C-18), 25.97 (t), 26.10 (t), 29.88 (t), 31.10 (t), 34.00 (t), 39.05 (d), 40.62 (d), 41.88 (s, C-13), 42.81 (d), 44.65 (t, C-1'), 113.30 (d), 115.31 (d), 126.61 (d), 131.56 (s), 137.73 (s), 153.96 (s, C-3), 172.21 (s, C=O) and 179.10 (s, C=O); MS m/z (FAB+) 707.3 [29, (2M+H)$^+$], 507.1 [72, (M+H+NBA)$^+$], 354.1 [100, (M+H)$^+$]; MS m/z (FAB−) 658.3 [13, (M−H+2NBA)$^−$], 505.2 [32, (M−H+NBA)$^−$], 352.1 [100, (M−H)$^−$]; Ace MS m/z (FAB+) 354.20686, C$_{22}$H$_{28}$NO$_3$ requires 354.20692. HPLC (methanol/water, 90:10; Xmax=259.2 nm) Rt=3.90 min, 100%. Found: C,; H,; N, C$_{22}$H$_{27}$NO$_3$ requires: C, 74.76; H, 7.70; N, 3.96.

3-Hydroxy-N-(3-picolyl)-16,17-seco-estra-1,3,5(10)-triene-16,17-imide (30) (STX 234)

Following the hydrogenation conditions (see VI-1-5), a suspension of 19 (190 mg, 395 μmol) and Pd—C (10%, 100 mg) in MeOH/THF 2:1 (30 mL) was hydrogenated for 20 hours to give 30 as a creamy solid (141 mg, 91%). An analytical sample was precipitated from ethyl acetate to give a white powder: mp; IR (KBr) 3380 (OH), 2940-2865 (aliph CH), 1720 (C=O), 1670 (C=O), 1610-1500 (arom C=C) cm$^{-1}$; $\delta_H$ (DMSO-d$_6$, 400 MHz) 1.11 (3H, s, C-18-H$_3$), 1.14-2.94 (11H, m), 2.67-2.75 (2H, m, C-6-H$_2$), 4.82 (1H, d, $J_{BA}$=14.8 Hz, N—CH$_A$H$_B$), 4.87 (1H, d, $J_{AB}$=14.8 Hz, N—CH$_A$H$_B$), 6.44 (1H, d, $J_{C\text{-}2\text{-}H,C\text{-}4\text{-}H}$=2.3 Hz, C-4-H), 6.52 (1H, dd, $J_{C\text{-}1\text{-}H,C\text{-}2\text{-}H}$=8.4 Hz and $J_{C\text{-}4\text{-}H,C\text{-}2\text{-}H}$=2.3 Hz, C-2-H), 7.07 (1H, d, $J_{C\text{-}2\text{-}H,C\text{-}1\text{-}H}$=8.6 Hz, C-1-H), 7.33 (1H, dd, $J_{C\text{-}3''\text{-}H, C\text{-}4''\text{-}H}$=7.8 Hz, $J_{C\text{-}5''\text{-}H, C\text{-}4''\text{-}H}$=4.7 Hz, C-4''-H), 7.59 (1H, m, C-3''-H), 8.42-8.47 (2H, m, C-1''-H and C-5''-H) and 9.05 (1H, s, exchanged with D$_2$O, OH); MS m/z (FAB+) 544.3 [6, (M+H+NBA)$^+$], 391.2 [88, (M+H)$^+$], 273.1 [18], 156.1 [40], 135.1 [46], 119.1 [48], 95.1 [70]; MS m/z (FAB−) 542.3 [50, (M−H+NBA)$^−$], 389.3 [100, (M−H)$^−$], 276.1 [43], 258.1 [37], 195.1 [42], 124.1 [34], 92.0 [27] Acc MS m/z (FAB+) 391.20190, C$_{24}$H$_{27}$N$_2$O$_3$ requires 391.20217.

3-Hydroxy-N-tert-butyl-benzyl-16,17-seco-estra-1,3, 5(10)-triene-16,17-imide (31) (STX 279)

Following the hydrogenation conditions (see VI-1-5), a suspension of 20 (620 mg, 1.16 mmol) and Pd—C (10%, 200 mg) in MeOH/THF 2:1 (30 mL) was hydrogenated for 5 hours to give 31 as a creamy solid (550 mg). This was recrystallized from methanol to give white flaky crystals (417 mg, 81%) and a further crop of the product (31 mg) was obtained from the residue of the mother liquor upon recrystallization from methanol (overall yield 87%): mp 128-130° C.; IR (KBr) 3415 (OH), 2955-2870 (aliph CH), 1725 (C=O), 1655 (C=O), 1610-1505 (arom C=C) cm$^{-1}$; $\delta_H$ (CDCl$_3$, 400 MHz) 1.16 (3H, s, C-18-H$_3$), 1.28 (9H, s, C(CH$_3$)$_3$), 1.30-3.02 (15H, m), 2.81-2.87 (2H, m, C-6-H$_2$), 4.77 (1H, s, exchanged with D$_2$O, OH), 4.88 (1H, d, $J_{BA}$=14.0 Hz, N—CH$_A$H$_B$), 4.95 (1H, d, $J_{AB}$=14.0 Hz, N—CH$_A$H$_B$), 6.57 (1H, d, $J_{C\text{-}2\text{-}H,C\text{-}4\text{-}H}$=2.7 Hz, C-4-H), 6.65 (1H, dd, $J_{C\text{-}1\text{-}H,C\text{-}2\text{-}H}$=8.2 Hz and $J_{C\text{-}4\text{-}H,C\text{-}2\text{-}H}$=2.7 Hz, C-2-H), 7.16 (1H, d, $J_{C\text{-}2\text{-}H,C\text{-}1\text{-}H}$=8.6 Hz, C-1-H) and 7.24-7.32 (4H, m, C-2''-H, C-3''-H, C-5''-H and C-6''-H); $\delta_C$ (CDCl$_3$, 100.4 MHz) 16.93 (q, C-18), 25.94 (t), 26.07 (t), 29.88 (t), 31.74 (3×q, C(CH$_3$)$_3$), 33.99 (t), 34.07 (t), 34.87 (s, C(CH$_3$)$_3$), 38.96 (d), 40.44 (d), 41.90 (s, C-13), 42.76 (d), 43.27 (t, C-1'), 113.30 (d), 115.30 (d), 125.55 (2×d), 126.64 (d), 128.35 (2×d), 131.45 (s), 134.44 (s), 137.71 (s), 150.30 (s), 153.95 (s, C-3), 172.01 (s, C=O) and 178.85 (s, C=O); MS m/z (FAB+) 891.4 [80, (2M+H)$^+$], 599.2 [35, (M+H+NBA)$^+$], 446.2 [100, (M+H)$^+$]; MS m/z (FAB−) 889.5 [42, (2M−H)$^−$], 751.4 [87, (M+2NBA)⁻], 598.3 [30, (M+NBA)⁻], 444.2 [100, (M−H)⁻]; Acc MS m/z (FAB+) 445.26176, $C_{29}H_{35}NO_3$ requires 354.20692. HPLC (methanol/water, 90:10; $\lambda_{max}$=259.2 nm) Rt=3.90 min, 100%. Found: C,; H,; N, $C_{22}H_{27}NO_3$ requires: C, 74.76; H, 7.70; N, 3.96.

3-Hydroxy-N-benzyl-16,17-seco-estra-1,3,5(10)-triene-16,17-imide (32) (STX 233)

Following the hydrogenation conditions (see VI-1-5), a suspension of 21 (230 mg, 479 µmol) and Pd—C (10%, 100 mg) in MeOH/THF 2:1 (30 mL) was hydrogenated for 2 hours to give 32 as a white solid (170 mg, 91%). This was washed with boiling McOH to give a white precipitate (122 mg, 65%): mp 298-301° C.; IR (KBr) 3430 (OH), 2950-2890 (aliph CH), 1720 (C=O), 1655 (C=O), 1610-1505 (arom C=C) cm⁻¹; $\delta_H$ (DMSO-$d_6$, 400 MHz) 1.12 (3H, s, C-18-$H_3$), 1.18-2.92 (11H, m), 2.68-2.75 (2H, m, C-6-$H_2$), 4.79 (1H, d, $J_{BA}$=14.8 Hz, N—$CH_AH_B$), 4.85 (1H, d, $J_{AB}$=14.8 Hz, N—$CH_AHs_B$), 6.45 (1H, d, $\overline{J_{C-2-H,C-4-H}}$=2.3 Hz, C-4-H), 6.53 (1H, dd, $J_{C-1-H,C-2-H}^{-}$=8.4 Hz and $J_{C-4-H,C-2-H}$=2.3 Hz, C-2-H), 7.07 (1H, d, $J_{C-2-H,C-1-H}$=8.6 Hz, C-1-H), 7.17-7.32 (5H, m, $C_6H_5$) and 9.05 (1H, s, exchanged with $D_2O$, OH); $\delta_C$ (DMSO-$d_6$, 100.4 MHZ)[b] 16.27 (q, C-18), 25.16 (2×t), 29.12 (t), 32.88 (t), 33.46 (t), 37.96 (d), 40.98 (s, C-13), 41.75 (d), 42.30 (t, C-1'), 112.72 (d), 114.51 (d), 125.82 (d), 126.63 (d), 126.84 (2×d), 128.08 (2×d), 129.41 (s), 136.69 (s), 137.36 (s), 154.81 (s, C-3), 172.21 (s, C=O) and 177.97 (s, C=O); MS m/z (FAB+) 390.3 [30, (M+H)⁺], 133.2 [43], 111.2 [57], 97.2 [100], 80.1 [23]; Acc MS m/z (FAB+) 390.20622, $C_{25}H_{25}NO_3$ requires 390.20692. HPLC (methanol/water, 90:10; $\lambda_{max}$=259.2 nm) Rt=3.90 min, 100%. Found: C,75.60; H, 7.01; N, 3.34. $C_{25}H_{27}NO_3$+$(H_2O)_{1/2}$ requires: C, 75.35; H, 7.08; N, 3.51. [b]one doublet hidden under solvent peaks
2-4—Synthesis of the N-allyl derivatives

3-tert-butyl-dimethylsilyl-16,17-seco-estra-1,3,5 (10)-triene-16,17-imide (33)

To a stirred solution of 5 (350 mg, 1.17 mmol) in DMF (20 mL) at room temperature under $N_2$ was added imidazole (96 mg, 1.40 mmol) and tert-butyl-dimethylsilyl chloride (194 mg, 1.29 mmol). The reaction mixture was stirred at room temperature under $N_2$ for 2 hours and another 2 eq. of imidazole and TBDMSCI were added to enable completion of the reaction after another 2 hours at room temperature. The mixture was then poured into water (150 mL) and the resulting solution was extracted with ethyl acetate (150 mL). The organic layer was separated, washed with $H_2O$ (4×80 mL), dried ($MgSO_4$), filtered and concentrated under reduced pressure. The white solid obtained was recrystallized from EtOH/$H_2O$ to give 33 as white crystals (336 mg, 70%) and a further crop of the product (40 mg) was obtained from the residue of the mother liquor upon recrystallization from EtOH/$H_2O$ (overall yield 78%): mp 261-264° C.; TLC (chloroform/acetone, 8:2) $R_f$ 0.65 cf. $R_f$ 0.40 (5); IR (KBr) 3210 (NH), 3090 (arom CH), 2950-2860 (aliph CH), 1730 (C=O), 1680 (C=O), 1610-1500 (arom C=C) cm⁻¹; $\delta_H$ (CDCl₃, 400 MHz) 0.19 (6H, s, Si(CH₃)₂), 0.97 (9H, s, C(CH₃)₃), 1.23 (3H, s, C-18-$H_3$), 1.31-2.96 (11H, m), 2.80-2.87 (2H, m, C-6-$H_2$), 6.57 (1H, d, $J_{C-2-H,C-4-H}$=2.3 Hz, C-4-H), 6.64 (1H, dd, $J_{C-1-H,C-2-H}$=8.6 Hz and $J_{C-4-H,C-2-H}$=2.7 Hz, C-2-H), 7.13 (1H, d, $J_{C-2-H,C-1-H}$=8.6 Hz, C-1-H) and 7.72 (1H, s, exchanged with $D_2O$, NH); $\delta_C$ (CDCl₃, 100.4 MHz)-4.23 (2×q, Si(CH₃)₂), 16.55 (q, C-18), 18.28 (s, C(CH₃)₃), 25.37 (t), 25.78 (3×q, C(CH₃)₃), 26.06 (t), 29.55 (t),$\overline{32.84}$ (t), 32.92 (t), 38.55 (d), 41.2$\overline{2}$ (s, C-13), 41.61 (d), 42.67 (d), 117.50 (d), 119.67 (d), 125.97 (d), 131.52 (s), 136.92 (s), 153.53 (s, C-3), 171.61 (s, C=O) and 178.36 (s, C=O); MS m/z (FAB+) 827.6 [50, (2M+H)⁺], 414.2 [100, (M+H)⁺], 356.2 [45, (M-C(CH₃)₃)+], 72.9 [50]; MS 7 m/z (FAB−) 719.4 [10, (M+2NBA)], 565.3 [24, (M−H+NBA)], 412.2 [100, (M−H)⁻]; Acc MS m/z (FAB+) 414.24527, $C_{24}H_{36}NO_5Si$ requires 414.24645. HPLC (methanol/water, 90:10; $\lambda_{max}$=259.2 nm) Rt=3.90 min, 100%. Found: C, 69.60; H, 8.46; N, 3.40. $C_{24}H_{35}NO_5Si$ requires: C, 69.69; H, 8.53; N, 3.39.

3-tert-butyl-dimethylsilyl-N-allyl-16,17-seco-estra-1, 3,5(10)-triene-16,17-imide (34)

Following the alkylation conditions (see VI-1-3), 33 (300 mg, 725 µmol) was treated with NaH (35 mg, 870 µmol) and the subsequent reaction with allyl bromide (126 µL, 1.45 mmol) was complete within 7 hours. Fractionation of the crude product that obtained by flash chromatography with chloroform as eluent gave 34 as a creamy oil (302 mg, 92%): TLC (chloroform/acetone, 8:2) $R_f$ 0.86 cf. $R_f$ 0.66 (33); IR (KBr) 2930-2860 (aliph CH), 1725 (C=O), 1676 (C=O), 1610-1500 (arom C=C) cm⁻¹; $\delta_H$ (CDCl₃, 400 MHz) 0.19 (6H, s, Si(CH₃)₂), 0.98 (9H, s, C(CH₃)₃), 1.19 (3H, s, C-18-$H_3$), 1.29-3.02 (1H, m), 2.80-2.86 (2H, m, C-6-$H_2$), 4.37 (2H, m, N—$CH_2$), 5.16 (2H, m, C-3'-$H_2$), 5.80 (1H, m, C-2'-H), 6.56 (1H, d, $J_{C-2-H,C-1-H}$=2.7 Hz, C-4-H), 6.64 (1H, dd, $J_{C-1-H,C-2-H}$=0.4 Hz and $J_{C-4-H,C-2-H}$=2.7 Hz, C-2-H) and 7.13 (1H, d, $J_{C-2-H,C-1-H}$=8.2 Hz, C-1-H); MS m/z (FAB+) 454.3 [100, (M+H)⁺], 396.2 [35, (M+H—C(CH₃)₃)⁺], 72.9 [54]; MS m/z (FAB−) 606.3 [32, (M+NBA)⁻], 452.2 [100, (M−H)⁻], 412.2 [56, (M−H—$C_3H_4$)⁻]; Acc MS m/z (FAB+) 454.27597, $C_{27}H_{40}NO_5Si$ requires 454.27775. HPLC (methanol/water, 90:10; $\lambda_{max}$=259.2 nm) Rt=3.90 min, 100%. CHN

3-Hydroxy-N-allyl-16,17-seco-estra-1,3,5(10)-triene-16,17-imide (35) (STX 274)

Tetrabutyl ammonium fluoride hydrate (183 mg, 701 µmol) was added to a stirred solution of 34 (265 mg, 584 µmol) in anhydrous DMF (10 mL) at room temperature under an atmosphere of $N_2$. The reaction mixture was stirred at room temperature for 2 hours and another 1.2 eq. of TBAF were added to enable completion of the reaction. After 5 hours, the mix was poured into water (40 mL) and the white precipitate formed was filtered, washed and air dried to give a white powder (I 72 mg, 87%). Purification of the crude product that obtained by recrystallization from ethyl acetate gave 35 as white crystals (101 mg, 51%) and a further crop of the product (13 mg) was obtained from the residue of the mother liquor upon recrystallization from ethyl acetate (overall yield 58%): mp 147-149° C.; TLC (chloroform/acetone, 8:2) $R_f$ 0.63 cf. $R_f$ 0.80 (34); IR (KBr) 3445 (OH), 2920-2860 (aliph CH), 1720 (C=O), 1660 (C=O), 1610-1505 (arom C=C) cm⁻¹; $\delta_H$ (CDCl₃, 400 MHz) 1.18 (3H, s, C-18-$H_3$), 1.30-3.02 (11H, m), 2.82-2.87 (2H, m, C-6-$H_2$), 4.37 (2H, ddt, $^4J_{C-3'-H,C-1'-H}$=1.4 Hz, $^3J_{C-2'-H,C-1'-H}$=5.5 Hz, $^1J_{C-1'-H,C-1'-H}$=14.8 Hz, N—$CH_2$), 4.72 (1H, s, exchanged with $D_2O$, OH), 5.11-5.21 (2H, m, C-3'-$H_2$), 5.80 (1H, m, C-2'-H), 6.58 (1H, d, $J_{C-2-H,C-4-H}$=2.7 Hz, C-4-H), 6.65 (1H, dd, $J_{C-1-H,C-2-H}$=8.4 Hz and $J_{C-4-H,C-2-H}$=2.7 Hz, C-2-H) and 7.17 (1H, d, $J_{C-2-H,C-1-H}$=8.2 Hz, C-1-H); MS m/z (FAB+) 340.2 [100, (M+H)⁺]; MS m/z (FAB−) 491.1 [50, (M−H+NBA)⁻], 338.1 [100, (M−H)⁻]; Acc MS m/z (FAB+) 340.19159, $C_{21}H_{26}NO_5$ requires 340.19127. HPLC (methanol/water, 70:30; $\lambda_{max}$=279.3 nm) Rt=3.91 min, 100%. Found: C, 73.90; H, 7.37; N, 4.11. $C_{21}H_{25}NO_5$ requires: C, 74.31; H, 7.42; N, 4.13.

2-5—Synthesis of the sulfamoylated parent compounds

3-Sulfamoyl-16,17-seco-estra-1,3,5(1(O)-triene-16,17-imide (36) (STX 211)

Following the sulfamoylation conditions (see VI-1-5), reaction of 5 (100 mg, 334 μmol) with sulfamoyl chloride in 1 mL DMA gave after 4 hours the crude product 36 (94 mg). This was washed with boiling acetone and the insoluble white solid was filtered (56 mg, 44%): mp 242-244° C.; TLC (chloroform/acetone, 9:1) $R_f$ 0.09 cf. $R_f$ 0.17 (5); IR (KBr) 3250 ($NH_2$), 3090 (arom CH), 2940-2850 (aliph CH), 1690 (C=O), 1695 (C=O), 1640-1560 (arom C=C), 1370 ($SO_2$), 1170 ($SO_2$) cm$^{-1}$; $\delta_H$ (DMSO-$d_6$, 400 MHz) 1.10 (3H, s, C-18-$H_3$), 1.19-2.72 (11H, m), 2.81-2.85 (2H, m, C-6-$H_2$), 6.98 (1H, d, $J_{C-2-H,C-4-H}$=2.3 Hz, C-4-H), 7.03 (1H, dd, $J_{C-1-H,C-2-H}$=8.6 Hz and $J_{C-4-H,C-2-H}$=2.3 Hz, C-2-H), 7.38 (1H, d, $J_{C-2-H,C-1-H}$=8.6 Hz, C-1-H), 7.91 (2H, s, exchanged with $D_2O$, $NH_2$) and 10.65 (1H, s, exchanged with $D_2O$, NH); $\delta_C$ (DMSO-$d_6$, 100.4 MHz) 16.18 (q, C-18), 24.97 (t), 25.03 (t), 29.05 (t), 32.38 (t), 32.72 (t), 37.50 (d), 40.31 (d), 40.49 (s, C-13), 42.10 (d), 119.19 (d), 121.46 (d), 126.43 (d), 137.54 (s), 137.62 (s), 147.82 (s, C-3), 172.11 (s, C=O) and 178.87 (s, C=O); MS m/z (FAB+) 532.3 [23, (M+H+NBA)$^+$], 379.3 [94, (M+H)$^+$], 157.2 [32], 133.2 [56], 97.2 [100], 82.2 [28]; MS m/z (FAB−) 531.2 [37, (M+NBA)$^-$], 377.2 [100, (M−H)$^-$], 78 [1,7]; Acc MS m/z (FAB+) 379.13314, $C_{18}H_{23}N_2O_5S$ requires 379.13277. HPLC (methanol/water, 50:50; $\lambda_{max}$=266.3 nm) Rt=5.70 min, 100%.

Found: C, 56.80; H, 5.83; N, 7.19. $C_{18}H_{22}N_2O_5S$ requires: C, 57.13; H, 5.86; N, 7.40.

3-Sulfamoyl-N-methyl-16,17-seco-estra-1,3,5(10)-triene-16,17-imide (37) (STX 212)

Following the sulfamoylation conditions (see VI-1-5), reaction of 22 (100 mg, 319 μmol) with sulfamoyl chloride in 1 mL DMA gave after 3 hours the crude product 37 (102 mg). This was recrystallized from chloroform to give 37 as white crystals (60 mg, 48%) and a further crop of the product (24 mg) was obtained from the residue of the mother liquor upon recrystallization from chloroform (overall yield 67%): mp 219-222° C.; IR (KBr) 3300 ($NH_2$), 3230 ($NH_2$), 3100 (arom CH), 2945-2865 (aliph CH), 1710 (C=O), 1655 (C=O), 1605-1500 (arom C=C), 1390 ($SO_2$), 1190 ($SO_2$) cm$^{-1}$; $\delta_H$(CDCl$_3$, 400 MHz) 1.18 (3H, s, C-18-$H_3$), 1.32-3.02 (11H, m), 2.89-2.93 (2H, m, C-6-$H_2$), 3.16 (3H, s, N—CH$_3$), 4.85 (2H, s, exchanged with $D_2O$, $NH_2$), 7.06 (1H, d, $J_{C-2-H,C-4-H}$=2.3 Hz, C-4-H), 7.11 (1H, dd, $J_{C-1-H,C-2-H}$=8.8 Hz and $J_{C-4-H,C-2-H}$=2.3 Hz, C-2-H) and 7.33 (1H, d, $J_{C-2-H,C-1-H}$=8.2 Hz, C-1-H); MS m/z (FAB+) 546.0 [10, (M+H+NBA)$^+$], 393.0 [100, (M+H)$^+$], 313.0 [12, (M+H—NH$_2$SO$_2$)+], 165.0 [25], 133.0 [22], 109.0 [43], 81.0 [64, (SO$_2$NH$_2$+H)$^+$]; MS m/z (FAB−) 783.4 [9, 2M−H)], 545.3 [38, (M+NBA)], 391.2 [100, (M−H)$^-$], 78.0 [16]; Acc MS m/z (FAB+) 393.14718, $C_{19}H_{25}N_2O_5S$ requires 393.14842. HPLC (methanol/water, 60:40; $\lambda_{max}$=266.3 nm) Rt=4.72 min, 100%. Found: C, 58.30; H, 6.17; N, 7.19. $C_{19}H_{24}N_2O_5S$ requires: C, 58.15; H, 6.16; N, 7.14.

3-Sulfamoyl-N-ethyl-16,17-seco-estra-1,3,5(10)-triene-16,17-imide (38) (STX 281)

Following the sulfamoylation conditions (see VI-1-5), reaction of 23 (70 mg, 214 μmol) with sulfamoyl chloride in 1 mL DMA gave after 1.5 hours the crude product 38 (86 mg). This was recrystallized from ethyl acetate/hexane 1:2 to give 38 as creamy crystals (72 mg, 83%): mp 215-217° C.; IR (KBr) 3415 ($NH_2$), 3305 ($NH_2$), 2970-2870 (aliph CH), 1715 (C=O), 1665 (C=O), 1375 ($SO_2$), 1190 ($SO_2$) cm$^{-1}$; $\delta_H$ (CDCl$_3$, 400 MHz) 1.11 (3H, t, J=7.0 Hz, C-2'-$H_3$), 1.17 (3H, s, C-18-$H_3$), 1.24-2.99 (11H, m), 2.88-2.95 (2H, m, C-6-$H_2$), 3.74-3.88 (2H, m, N—CH$_2$), 4.89 (2H, s, exchanged with $D_2O$, $NH_2$), 7.06 (1H, d, Jc-2-H,C-4-H=2.3 Hz, C-4-H), 7.12 (1H, dd, $J_{C-1-H,C-2-H}$=8.4 Hz and $J_{C-4-H,C-2-H}$=2.5 Hz, C-2-H) and 7.33 (1H, d, $J_{C-2-H,C-1-H}$=8.6 Hz, C-1-H); MS m/z (FAB+) 813.2 [40, (2M+H)$^+$], 560.1 [70, (M+H+NBA)$^+$], 407.1 [100, (M+H)$^+$]; MS m/z (FAB−) 811.4 [72, (2M−H)$^-$], 712.3 [47, (M+2NBA)$^-$], 559.2 [30, (M+NBA)$^-$], 405.1 [100, (M−H)$^-$]; Ace MS m/z (FAB+) 407.16455, $C_{20}H_{27}N_2O_5S$ requires 407.16407. HPLC (methanol/water, 90:10; $\lambda_{max}$=259.2 nm) Rt=3.90 min, 100%. Found: C,; H,; N, $C_{20}H_{27}N_2O_5S$ requires: C, 59.09; H, 6.45; N, 6.89.

3-Sulfamoyl-N-propyl-16,17-seco-estra-1,3,5(10)-triene-16,17-imide (39) (STX 213)

Following the sulfamoylation conditions (see VI-1-5), reaction of 24 (100 mg, 293 μmol) with sulfamoyl chloride in 1 mL DMA gave after 6 hours the crude product 39 (156 mg). Fractionation of the crude product that obtained by flash chromatography with chloroform/acetone (95:5) as eluent gave 39 as a white residue (107 mg, 87%). An analytical sample was recrystallized from acetone/hexane (1:2) to give white crystals: mp 202-204° C.; IR (KBr) 3365 ($NH_2$), 3255 ($NH_2$), 3095 (arom CH), 2965-2880 (aliph CH), 1710 (C=O), 1660 (C=O), 1600-1500 (arom C=C), 1380 ($SO_2$), 1180 ($SO_2$) cm$^{-1}$; $\delta_H$ (CDCl$_3$, 400 MHz) 0.90 (3H, t, J=7.4 Hz, C-3'-$H_3$), 1.17 (3H, s, C-18-$H_3$), 1.32-3.00 (13H, m), 2.88-2.93 (2H, m, C-6-$H_2$), 3.64-3.80 (2H, m, N—CH$_2$), 4.90 (2H, s, exchanged with $D_2O$, $NH_2$), 7.06 (1H, d, $J_{C-2-H,C-4-H}$=2.3 Hz, C-4-H), 7.11 (1H, dd, $J_{C-1-H,C-2-H}$=8.6 Hz and $J_{C-4-H,C-2-H}$=2.7 Hz, C-2-H) and 7.33 (1H, d, $J_{C-2-H,C-1-H}$=8.2 Hz, C-1-H); MS m/z (FAB+) 574.0 [8, (M+H+NBA)], 421.0 [100, (M+H)], 341.0 [12, (M+H—NH$_2$SO$_2$)]], 109.0 [52], 97.0 [45], 81.0 [74, (SO$_2$NH$_2$+H)$^+$], 67.0 [60]; MS m/z (FAB−) 573.3 [34, (M+NBA)$^-$], 419.3 [100, (M−H)$^-$], 276.2 [10], 78 [16]; Acc MS m/z (FAB+) 421.18002, $C_{21}H_{29}N_2O_5S$ requires 421.17972. HPLC (methanol/water, 70:30; $\lambda_{max}$=266.3 nm) Rt=4.61 min, 100%. Found: C, 60.00; H, 6.60; N, 6.49. $C_{21}H_{28}N_2O_5S$ requires: C, 59.98; H, 6.71; N, 6.66.

3-Sulfamoyl-N-butyl-16,17-seco-estra-1,3,5(10)-triene-16,17-imide (40) (STX 283)

Following the sulfamoylation conditions (see VI-1-5), reaction of 25 (90 mg, 253 μmol) with sulfamoyl chloride in 1 mL DMA gave after 1.5 hours the crude product 40 (109 mg). The crude product obtained was recrystallized from acetone/hexane 1:2 to give 40 as white crystals (67 mg, 61%) and a further crop of the product (11 mg) was obtained from the residue of the mother liquor upon recrystallization from acetone/hexane 1:2 (overall yield 71%): mp 194-196° C.; IR (KBr) 3335 ($NH_2$), 3250 ($NH_2$), 2940-2870 (aliph CH), 1710 (C=O), 1650 (C=O), 1385 ($SO_2$), 1190 ($SO_2$) cm$^{-1}$; $\delta_H$ (CDCl$_3$, 400 MHz) 0.92 (3H, t, J=7.2 Hz, C-4'-$H_3$), 1.17 (3H, s, C-18-$H_3$), 1.25-2.99 (15H, m), 2.88-2.92 (2H, m, C-6-$H_2$), 3.75 (2H, m, N—CH$_2$), 4.91 (2H, s, exchanged with $D_2O$, $NH_2$), 7.06 (1H, d, $J_{C-2-H,C-4-H}$=2.3 Hz, C-4-H), 7.12 (1H, dd, $J_{C-1-H,C-2-H}$=8.8 Hz and $J_{C-4-H,C-2-H}$=2.3 Hz, C-2-H) and 7.34 (1H, d, $J_{C-2-H,C-1-H}$=8.6 Hz, C-1-H); MS m/z (FAB+) 869.2

[78, (2M+H)+], 588.1 [78, (M+H+NBA)+], 435.1 [100, (M+H)+]; MS m/z (FAB−) 587.2 [32, (M+NBA)-], 433.2 [100, (M−H)−]; Ace MS m/z (FAB+) 435.19598, $C_{22}H_{31}N_2O_5S$ requires 435.19537. HPLC (methanol/water, 90:10; $\lambda_{max}$=259.2 nm) Rt=3.90 min, 100%. Found: C,; H,; N, $C_{22}H_{30}N_2O_5S$ requires: C, 60.81; H, 6.96; N, 6.45.

3-Sulfamoyl-N-pentyl-16,17-seco-estra-1,3,5(10)-triene-16,17-imide (41) (STX 214)

Following the sulfamoylation conditions (see VI-1-5), reaction of 26 (100 mg, 271 μmol) with sulfamoyl chloride in 1 mL DMA gave after 3.5 hours the crude product 41 (120 mg). Fractionation of the crude product that obtained by flash chromatography with chloroform/acetone (95:5) as eluent gave 41 as a white foam (111 mg, 92%). An analytical sample was recrystallized from ethyl acetate/hexane (1:2) to give white crystals: mp 159-161° C.; IR (KBr) 3345, 3255 ($NH_2$), 3095 (arom CH), 2930-2870 (aliph CH), 1720 (C=O), 1655 (C=O), 1600-1500 (arom C=C), 1385 ($SO_2$), 1190 ($SO_2$) $cm^{-1}$; $\delta_H$ ($CDCl_3$, 100 MHz) 0.89 (3H, t, J=7.4 Hz, C-5'-$H_3$), 1.17 (3H, s, C-18-$H_3$), 1.21-2.98 (17H, m), 2.90-2.94 (2H, m, C-6-$H_2$), 3.66-3.81 (2H, s, N—$CH_2$), 4.94 (2H, s, exchanged with $D_2O$, $NH_2$), 7.06 (1H, d, $J_{C-2-H,C-4-H}$=2.7 Hz, C-4-H), 7.11 (1H, dd, $J_{C-1-H,C-2-H}$=8.6 Hz and $J_{C-4-H,C-2-H}$=2.3 Hz, C-2-H) and 7.33 (1H, d, $J_{C-2-H,C-1-H}$=8.6 Hz, C-1-H); $\delta_C$ ($CDCl_3$, 100.4 MHz) 13.95 (q, C-5'), 16.44 (q, C-18), 22.31 (t), 25.33 (2xt), 27.54 (t), 29.00 (t), 29.32 (t), 33.46 (t), 33.55 (t), 38.06 (d), 40.02 (t, C-1'), 40.19 (d), 41.24 (s, C-13), 42.52 (d), 119.02 (d), 121.59 (d), 126.47 (d), 137.98 (s), 138.13 (s), 147.82 (s, C-3), 171.28 (s, C=O) and 178.09 (s, C=O); MS m/z (FAB+) 602.0 [8, (M+H+NBA)1], 449.0 [100, (M+H)+], 369.1 [12, (M+H—$NH_2SO_2$)+], 133.0 [33], 111.0 [32], 97.0 [46]; MS m/z (FAB−) 601.4 [34, (M+NBA)−], 447.3 [100, (M−H)−], 276.2 [18]; Ace MS m/z (FAB+) 449.21109, $C_{23}H_{33}N_2O_5S$ requires 449.21102. HPLC (methanol/water, 80:20; $\lambda_{max}$=266.3 nm) Rt=3.70 min, 97.9%. Found: C, 61.70; H, 7.30; N, 6.22. $C_{23}H_{32}N_2O_5S$ requires: C, 61.58; H, 7.19; N, 6.24.

3-Sulfamoyl-N-hexyl-16,17-seco-estra-1,3,5(10)-triene-16,17-imide (42) (STX 282)

Following the sulfamoylation conditions (see VI-1-5), reaction of 27 (130 mg, 339 μmol) with sulfamoyl chloride in 2.5 mL DMA gave after 2 hours the crude product 42 (157 mg). Fractionation of the crude product that obtained by flash chromatography with chloroform/acetone (9:1) as eluent gave a white foam (127 mg, 81%). This was recrystallized from ethyl acetate/hexane 1:2 to give 42 as colourless crystals (77 mg, 49%): mp 112-115TC; IR (KBr) 3310 ($NH_2$), 3190 ($NH_2$), 2925-2860 (aliph CH), 1720 (C=O), 1655 (C=O), 1390 ($SO_2$), 1185 ($SO_2$) $cm^{-1}$; $\delta_H$ ($CDCl_3$, 400 MHz) 0.88 (3H, t, J=6.6 Hz, C-6'-$H_3$), 1.19 (3H, s, C-18-$H_3$), 1.24-2.99 (19H, m), 2.88-2.94 (2H, m, C-6-$H_2$), 3.66-3.82 (2H, m, N—$CH_2$), 4.91 (2H, s, exchanged with $D_2O$, $NH_2$), 7.06 (1H, d, $J_{C-2-H,C-4-H}$=2.3 Hz, C-4-H), 7.11 (1H, dd, $J_{C-1-H,C-2-H}$=8.6 Hz and $J_{C-4-H,C-2-H}$=2.7 Hz, C-2-H) and 7.33 (1H, d, $J_{C-2-H,C-1-H}$=8.6 Hz, C-1-H); 6 ($CDCl_3$, 100.4 MHz) 14.15 (q, C-6'), 16.58 (q, C-18), 22.63 (t), 25.46 (t), 26.67 (t), 27.95 (t), 29.46 (t), 31.53 (2xt), 33.59 (t), 33.68 (t), 38.18 (d), 40.19 (t, C-1'), 40.32 (d), 41.37 (s, C-13), 42.65 (d), 119.18 (d), 121.74 (d), 126.61 (d), 138.12 (s), 138.26 (s), 147.94 (s, C-3), 171.46 (s, C=O) and 178.24 (s, C=O); MS m/z (FAB+) 925.3 [64, (2M+H)+], 616.2 [20, (M+H+NBA)+], 463.1 [100, (M+H)+]; MS m/z (FAB−) 1077.5 [70, (2M+NBA)−], 615.3 [70, (M+NBA)−], 462.2 [100, M-]; Acc MS m/z (FAB+) 463.22629, $C_{24}H_{35}N_2O_5S$ requires 463.22667. HPLC (methanol/water, 90:10; $\lambda_{max}$=259.2 nm) Rt=3.90 min, 100%. Found: C, 62.60; H, 7.43; N, 6.20. $C_{24}H_{34}N_2O_5S$ requires: C, 62.31; H, 7.41; N, 6.06.

3-Sulfamoyl-N-bromobutyl-16,17-seco-estra-1,3,5(10)-triene-16,17-imide (43) (STX 286)

Sodium hydride (60% dispersion in mineral oil, 14 mg, 359 μmol) was added to a stirred solution of 28 (130 mg, 299 μmol) in anhydrous DMF (2 mL) at 0° C. under an atmosphere of $N_2$. After evolution of hydrogen had ceased, sulfamoyl chloride (6 eq) was added. The reaction mixture was then stirred under $N_2$ for 2 hours in which time it was allowed to warm to room temperature. The mixture was poured into brine (30 mL), and the resulting solution was extracted with ethyl acetate (2×30 mL). The organic layer was separated, washed with brine (5×25 mL), dried ($MgSO_4$), filtered and concentrated under reduced pressure. Fractionation of the crude product that obtained (188 mg) by flash chromatography with chloroform/acetone (9:1) as eluent gave 43 as a white foam (154 mg, 100%). This was recrystallized from ethyl acetate/hexane 1:2 to give white crystals (113 mg, 73%) and a further crop of the product (12 mg) was obtained from the residue of the mother liquor upon recrystallization from ethyl acetate/hexane 1:2 (overall yield 81%): mp 162-165° C.; IR (KBr) 3380 ($NH_2$), 3260 ($NH_2$), 2945-2870 (aliph CH), 1720 (C=O), 1650 (C=O), 1565-1495 (arom C=C), 1388 ($SO_2$), 1180 ($SO_2$) $cm^{-1}$; $\delta_H$ ($CDCl_3$, 400 MHz) 1.18 (3H, s, C-18-$H_3$), 1.22-3.00 (15H, m), 2.86-2.97 (2H, m, C-6-$H_2$), 3.42 (2H, t, J=6.6 Hz, $CH_2$Br), 3.79 (2H, m, N—$CH_2$), 4.89 (2H, s, exchanged with $D_2O$, $NH_2$), 7.06 (1H, d, $J_{C-2-H,C-4-H}$=2.3 Hz, C-4-H), 7.12 (1H, dd, $J_{C-1-H,C-2-H}$=8.6 Hz and $J_{C-4-H,C-2-H}$=2.7 Hz, C-2-H) and 7.33 (1H, d, $J_{C-2-H,C-1-H}$=8.6 Hz, C-1-H); $\delta_C$ ($CDCl_3$, 100.4 MHz) 16.63 (q, C-18), 25.42 (t), 25.46 (t), 26.74 (t), 29.44 (t), 30.14 (t), 33.20 (t), 33.55 (t), 33.66 (t), 38.16 (d), 39.07 (t, C-1'), 40.29 (d), 41.41 (s, C-13), 42.64 (d), 119.18 (d), 121.73 (d), 126.62 (d), 138.09 (s), 138.20 (s), 147.95 (s, C-3), 171.42 (s, C=O) and 178.24 (s, C=O); MS m/z (FAB+) 513.1 [100, (M+H)], 435.2 [46, (M-Br+H)]; Acc MS m/z (FAB+) 513.10382, $C_{22}H_{30}{}^{79}BrN_2O_5S$ requires 513.10588 and 515.10385, $C_{22}H_{30}{}^{81}BrN_2O_5S$ requires 515.10383. HPLC (methanol/water, 90:10; $\lambda_{max}$=259.2 nm) Rt=3.90 min, 100%. Found: C,; H,; N, $C_{22}H_{29}BrN_2O_5S$ requires: C, 51.46; H, 5.69; N, 5.46.

3-Sulfamoyl-N-cyclopropylmethyl-16,17-seco-estra-1,3,5(10)-triene-16,17-imide (44) (STX 284)

Following the sulfamoylation conditions (see VI-1-5), reaction of 29 (100 mg, 283 μmol) with sulfamoyl chloride in 1 mL DMA gave after 1.5 hours the crude product 44 (127 mg). This was recrystallized from acetone/hexane 1:2 to give 44 as white crystals (84 mg, 69%) and a further crop of the product (28 mg) was obtained from the residue of the mother liquor upon recrystallization from acetone/hexane 1:2 (overall yield 92%): mp 202-204° C.; IR (KBr) 3280 (br, $NH_2$), 2960 (aliph CH), 1700 (C=O), 1660 (C=O), 1395 ($SO_2$), 1185 ($SO_2$) $cm^{-1}$; $\delta_H$ ($CDCl_3$, 400 MHz) 0.29-0.34 (2H, m, C-3'-$H_2$), 0.40-0.45 (2H, m, C4'-$H_2$), 1.08-1.16 (1H, m, C-1'-H), 1.19 (3H, s, C-18-$H_3$), 1.32-3.02 (11H, m), 2.88-2.96 (2H, m, C-6-$H_2$), 3.66 (2H, m, N—$CH_2$), 4.93 (2H, s, exchanged with $D_2O$, $NH_2$), 7.07 (1H, d, $J_{C-2-H,C-4-H}$=2.3 Hz, C-4-H), 7.12 (1H, dd, $J_{C-1-H,C-2-H}$=8.6 Hz and $J_{C-4-H,C-2-H}$=2.7 Hz, C-2-H) and 7.34 (1H, d, $J_{C-2-H,C-1-H}$=8.6 Hz, C-1-H); MS m/z (FAB+) 865.1 [55, (2M+H)+], 586.1 [45, (M+H+NBA)$^+$], 433.0 [100, (M+H)$^+$]; MS m/z (FAB−) 863.4 [13, (2M−H)$^-$], 585.2 [30, (M+NBA)$^-$], 431.2 [100, (M−H)$^-$]; Acc MS m/z (FAB+) 433.17944, $C_{22}H_{29}N_2O_5S$ requires 433.17972. HPLC (methanol/water, 90:10; $\lambda_{max}$=259.2 nm) Rt=3.90 min, 100%. Found: C, 61.00; H, 6.85; N, 5.91. $C_{22}H_{28}N_2O_5S$ requires: C, 61.09; H, 6.52; N, 6.48.

3-Sulfamoyl-N-(3-picolyl)-16,17-seco-estra-1,3,5 (10)-triene-16,17-imide (45) (STX 237)

Following the sulfamoylation conditions (see VI-1-5), reaction of 30 (55 mg, 154 µmol) with sulfamoyl chloride in 0.5 mL DMA gave after 2 hours the crude product 45 (50 mg). Fractionation of the crude product that obtained by flash chromatography with chloroform/acetone (7:3) as eluent gave 45 as a white powder (27 mg, 41%). This was washed with boiling acetone and the white precipitate was filtered (10 mg, 15%): mp 215-218° C.; IR, $\delta_H$ (DMSO-d$_6$, 400 MHz) 1.10 (3H, s, C-18-H$_3$), 1.15-2.97 (11H, m), 2.79-2.84 (2H, m, C-6-H$_2$), 4.81 (1H, d, $J_{BA}$=14.8 Hz, N—CH$_A$H$_B$), 4.86 (1H, d, $J_{AB}$=14.8 Hz, N—CH$_A$H$_B$), 6.96 (1H, d, $J_{C-2-H,C-4-H}$=2.7 Hz, C-4-H), 7.01 (1H, dd, $J_{C-1-H,C-2-H}$=8.6 Hz and $J_{C-4-H,C-2-H}$=2.7 Hz, C-2-H), 7.31 (1H, dd, $J_{C-3''-H,C-4''-H}$=7.8 Hz, $J_{C-5''-H,C-4''-H}$=4.7 Hz, C-4''-H), 7.36 (1H, d, $J_{C-2-H,C-1-H}$=8.6 Hz, C-1-H), 7.57 (1H, m, C-3''-H), 7.89 (2H, s, exchanged with D$_2$O, NH$_2$) and 8.41-8.44 (2H, m, C-1''-H and C-5''-H); MS m/z (FAB+) 470.3 [48, (M+H)$^+$], 133.2 [38], 111.2 [52], 97.1 [100]; MS m/z (FAB−) 622.3 [52, (M+NBA)$^-$], 468.3 [100, (M−H)$^-$], 276.2 [62], 198 [48], 139.1 [46], 93.1 [40]; Acc MS m/z (FAB+) 470.17666, $C_{24}H_{28}N_3O_5S$ requires 470.17497. HPLC (methanol/water, 60:40; $\lambda_{max}$=260.4 nm) Rt=4.84 min, 100%. Found: C, 60.00; H, 5.86; N, 8.57. $C_{24}H_{27}N_3O_5S+(H_2O)_{1/2}$ requires: C, 60.03; H, 5.90; N, 8.78.

3-Sulfamoyl-N-tert-butyl-benzyl-16,17-seco-estra-1,3,5(10)-triene-16,17-imide (46) (STX 285)

Following the sulfamoylation conditions (see VI-1-5), reaction of 31 (200 mg, 449 mmol) with sulfamoyl chloride in 2 mL DMA gave after 6.5 hours the crude product 46 (235 mg). This was recrystallized from ethyl acetate/hexane 1:2 to give 46 as white crystals (199 mg, 85%): mp 227-230° C.; IR (KBr) 3320 (NH$_2$), 3240 (NH$_2$), 2960-2870 (aliph CH), 1720 (C=O), 1660 (C=O), 1385 (SO$_2$), 1180 (SO$_2$) cm$^{-1}$; $\delta_H$ (CDCl$_3$, 400 MHz) 1.16 (3H, s, C-18-H$_3$), 1.29 (9H, s, C(CH$_3$)$_3$), 1.30-3.02 (H, m), 2.87-2.93 (2H, m, C-6-H$_2$), 4.87 (2H, s, exchanged with D$_2$O, NH$_2$), 4.87-4.96 (2H, m, N—CH$_A$H$_B$) 7.06 (1H, d, $J_{C-2-H,C-4-H}$=2.3 Hz, C-4-H), 7.11 (1H, dd, $J_{C-1-H,C-2-H}$=8.6 Hz and $J_{C-4-H,C-2-H}$=2.7 Hz, C-2-H) and 7.24-7.34 (5H, m, C-1-H, C-2''-H, C-3''-H, C-5''-H and C-6''-H); $\delta_C$ (CDCl$_3$, 100.4 MHz) 16.39 (q, C-18), 25.31 (t), 25.28 (t), 29.29 (t), 31.24 (3×q, C(H$_3$)$_3$), 33.46 (t), 33.53 (t), 34.39 (s, C(CH$_3$)$_3$), 38.02 (d), 40.02 (d), 41.31 (s, C-13), 42.47 (d), 42.78 (t, C-1'), 119.03 (d), 121.58 (d), 125.07 (2×d), 126.46 (d), 127.84 (2×d), 133.93 (s), 137.94 (s), 138.07 (s), 147.80 (s), 149.85 (s, C-3), 171.23 (s, C=O) and 178.06 (s, C=O); MS m/z (FAB+) 1049.3 [70, (2M+H)$^+$], 678.1 [20, (M+H+NBA)$^+$], 525.1 [100, (M+H)$^+$]; MS m/z (FAB−) 1047.5 [80, (2M−H)$^-$], 677.3 [22, (M+NBA)$^-$], 523.2 [100, (M−H)$^-$]; Acc MS m/z (FAB+) 524.23309, $C_{29}H_{36}N_2O_5S$ requires 524.23449. HPLC (methanol/water, 90:10; $\lambda_{max}$=259.2 nm) Rt=3.90 min, 100%. Found: C,; H,; N, $C_{29}H_{36}N_2O_5S$ requires: C, 66.39; H, 6.92; N, 5.34.

3-Sulfamoyl-N-benzyl-16,17-seco-estra-1,3,5(10)-triene-16,17-imide (47) (STX 236)

Following the sulfamoylation conditions (see VI-1-5), reaction of 32 (150 mg, 385 µmol) with sulfamoyl chloride in 1.5 mL DMA gave after 3 hours the crude product 47 (205 mg). Fractionation of the crude product that obtained by flash chromatography with chloroform/acetone (9:1) as eluent gave 47 as a white powder (151 mg, 84%). This was recrystallized from acetone/hexane 1:2 to give white crystals (133 mg, 74%): mp 208-210° C.; IR (KBr) 3340 (NH$_2$), 3230 (NH$_2$), 3100-3050 (arom CH), 2950-2870 (aliph CH), 1715 (C=O), 1655 (C=O), 1610-1495 (arom C=C), 1385 (SO$_2$), 1195 (SO$_2$) cm$^{-1}$; $\delta_H$ (DMSO-d$_6$, 400 MHz) 1.13 (3H, s, C-18-H$_3$), 1.17-2.96 (11H, m), 2.81-2.87 (2H, m, C-6-H$_2$), 4.80 (1H, d, $J_{BA}$=14.8 Hz, N—CH$_A$H$_B$), 4.86 (1H, d, $J_{AB}$=14.4 Hz, N—CH$_A$H$_B$), 6.99 (1H, d, $J_{C-2-H,C-4-H}$=2.3 Hz, C-4-H), 7.04 (1H, dd, $J_{C-1-H,C-2-H}$=8.4 Hz and $J_{C-4-H,C-2-H}$=2.3 Hz, C-2-H), 7.19-7.40 (6H, m, C$_6$H$_5$ and C-1-H) and 7.92 (2H, s, exchanged with D$_2$O, NH$_2$); MS m/z (FAB+) 469.2 [100, (M+H)$^+$], 389.2 [7, (M+H—SO$_2$NH$_2$)+], 97.1 [17]; MS m/z (FAB−) 935.3 [10, (2M−H)$^-$], 621.3 [38, (M+NBA)$^-$], 467.2 [100, (M−H)$^-$]; Acc MS m/z (FAB+) 469.17892, $C_{25}H_{29}N_2O_5S$ requires 469.17972. HPLC (methanol/water, 70:30; $\lambda_{max}$=266.3 nm) Rt=5.14 min, 100%. Found: C, 63.90; H, 6.12; N, 5.86. $C_{25}H_{28}N_2O_5S$ requires: C, 64.08; H, 6.02; N, 5.98.

3-Sulfamoyl-N-allyl-16,17-seco-estra-1,3,5(10)-triene-16,17-imide (48) (STX 280)

Following the sulfamoylation conditions (see VI-1-5), reaction of 35 (150 mg, 345 µmol) with sulfamoyl chloride in 2 mL DMA gave after 3 hours the crude product 48 (85 mg). Fractionation of the crude product that obtained by flash chromatography with chloroform/acetone (9:1) as eluent gave 48 as a white foam (85 mg, 99%). This was recrystallized from acetone/hexane 1:2 to give white crystals (75 mg, 87%): mp 210-213° C.; TLC (chloroform/acetone, 9:1) R$_f$ 0.33 cf. R$_f$ 0.52 (35); IR (KBr) 3385 (NH$_2$), 3275 (NH$_2$), 2935-2870 (aliph CH), 1715 (C=O), 1670 (C=O), 1600-1495 (arom C=C), 1385 (SO$_2$), 185 (SO$_2$) cm$^{-1}$; $\delta_H$ (DMSO-d$_6$, 400 MHz) 1.13 (3H, s, C-18-H$_3$), 1.25-2.89 (1H, m), 2.81-2.87 (2H, m, C-6-H$_2$), 4.24 (2H, m, N—CH$_2$), 4.97-5.08 (2H, m, C-3'-H$_2$), 5.75 (1H, m, C-2'-H), 6.99 (1H, d, $J_{C-2-H,C-4-H}$=2.3 Hz, C-4-H), 7.04 (1H, dd, $J_{C-1-H,C-2-H}$=8.6 Hz and $J_{C-4-H,C-2-H}$=2.7 Hz, C-2-H), 7.38 (1H, d, $J_{C-2-H,C-1-H}$=8.6 Hz, C-1-H) and 7.91 (2H, s, exchanged with D$_2$O, NH$_2$); $\delta_C$ (DMSO-d$_6$, 100.4 MHz)$^c$ 16.33 (q, C-18), 24.85 (t), 25.04 (t), 29.04 (t), 32.83 (t), 33.46 (t), 37.45 (d), 40.93 (s, C-13), 41.08 (t, C-1'), 41.99 (d), 115.58 (t, C-3'), 119.22 (d), 121.51 (d), 126.44 (d), 132.75 (d), 137.49 (s), 137.63 (s), 147.83 (s, C-3), 170.81 (s, C=O) and 177.56 (s, C=O); MS m/z (FAB+) 837.4 [48, (2M+H)$^+$], 725.3 [12, (M+H+2NBA)$^+$], 572.2 [68, (M+H+NBA)$^+$], 419.1 [100, (M+H)$^+$], 80.9 [18, (SO$_2$NH$_2$+H)$^+$]; MS m/z (FAB−) 571.1 [30, (M+NBA)$^-$], 417.1 [100, (M−H)$^-$]; Acc MS m/z (FAB+) 419.16347, $C_{21}H_{27}N_2O_5S$ requires 419.16407. HPLC (methanol/water, 70:30; $\lambda_{max}$=266.3 nm) Rt=3.25 min, 100%. Found: C, 60.30; H, 6.32; N, 6.56. $C_{21}H_{26}N_2O_5S$ requires: C, 60.27; H, 6.26; N, 6.69. $^c$one doublet hidden under solvent peaks 2-6—Synthesis of the sulfamoylated parent compounds

2-Iodo-estrone (49)

To a stirred solution of oestrone (10 g, 36.98 mmol) in a mixture of acetic acid (570 mL) and tetrahydrofurane (280 mL) warmed to 55° C. was added mercuric acetate (5.89 g, 18.49 mmol). After 15 minutes, iodine (8.70 g, 34.37 mmol) was added to give a clear orange solution which was stirred for two hours at room temperature. The resulting light yellow mixture was then concentrated under reduced pressure and a solution of potassium iodide (5% aqueous, 300 mL) was added. The organic fraction was extracted with ethyl acetate (2×300 mL), washed with aqueous sodium thiosulfate (3×200 mL) and brine (1×200 mL), dried (MgSO$_4$), filtered and evaporated in vacuo. The crude brown solid that obtained was first recrystallized from acetic acid to give 49 as a blue solid (6.42 g, 44%) and a further crop of the product (3.00 g) was obtained from the residue of the mother liquor upon recrystallization from ethanol (overall 'crude' yield 64%). Both crops were further recrystallized from ethanol to give light grey flaky crystals (8.20 g, overall yield 56%): mp 213-215° C. (dec) (lit. ° C.); [43] $\delta_H$ (CDCl$_3$, 400 MHz) 0.91 (3H, s, C-18-H$_3$), 1.36-2.57 (13H, m), 2.83-2.86 (2H, m, C-6-H$_2$), 5.09 (1H, s, exchanged with D$_2$O, OH), 6.74 (1H, s, C-4-H) and 7.52 (1H, s, C-1-H).

2-Methoxy-estrone (50)

2-Iodoestrone 49 (4 g, 10.09 mmol) and copper chloride (452 mg, 3.365 mmol) were stirred at room temperature under an atmosphere of N$_2$ in anhydrous pyridine (35 mL) for 30 minutes. A freshly prepared 5.1 M solution of sodium methoxide (0.101 mot, 19.7 mL) was then added to the mixture and the blue solution was refluxed for 45 minutes under N$_2$. After cooling, the resulting orange solution was poured into ice and acidified with 5M HCl. The organic layer was extracted with ethyl acetate (3×200 mL), washed with a saturated solution of sodium hydrogenocarbonate (2×200 mL) and brine (2×200 mL), dried (MgSO$_4$), filtered and evaporated in vacuo. Fractionation of the crude product that obtained by flash chromatography with ethyl acetate/hexane (3:17 to 5:15) as eluent gave 50 as a creamy residue (2.58 g, 78%): mp 167-170° C. (lit. ° C.); [43] $\delta_H$ (CDCl$_3$, 400 MHz) 0.92 (3H, s, C-18-H$_3$), 1.38-2.54 (13H, m), 2.80-2.84 (2H, m, C-6-H$_2$), 3.86 (3H, s, OCH$_3$), 5.45 (1H, s, exchanged with D$_2$O, OH), 6.66 (1H, s, C-4-H) and 6.79 (1H, s, C-1-H).

2-Methoxy-3-benzyloxy-estrone (51)

To a stirred solution of 50 (1.91 g, 6.36 mmol) in DMF (20 mL) at 0° C. under an atmosphere of N$_2$, potassium tert-butoxide (1.07 g, 9.54 mmol) was added portion wise. The resulting orange suspension was stirred under N$_2$ for two hours, in which time it was allowed to warm to room temperature. Benzyl bromide (1.13 mL, 9.54 mmol) was then added and the mixture was stirred at room temperature, under N$_2$ for two hours. The resulting orange solution was poured into water (50 mL) and the organic fraction was extracted with ethyl acetate (2×50 mL), washed with water (2×50 mL), brine (2×50 mL), dried (MgSO$_4$), filtered and evaporated in vacuo. The crude product obtained was recrystallized from ethanol to give a 51 as a light orange powder (2.3 g). This was further recrystallized from ethanol to give a creamy powder (1.52 g, 61%) and a further crop of the product (0.29 g) was obtained from the residue of the mother liquor upon recrystallization from ethanol (overall yield 73%): mp 120-123° C. (lit. ° C.); [43] $\delta_H$ (CDCl$_3$, 400 MHz) 0.92 (3H, s, C-18-H3), 1.36-2.55 (13H, m), 2.74-2.85 (2H, m, C-6-H$_2$), 3.86 (3H, s, OCH$_3$), 5.11 (2H, s, OCH$_2$Ar), 6.64 (1H, s, C-4-H), 6.84 (1H, s, C-1-H) and 7.29-7.46 (5H, m, C$_6$H$_5$); MS m/z (FAB+) 495.2 [10, (M+H+NBA)$^+$], 342.1 [100, (M+H)$^+$], 299.1 [40, (M+H-Ac)+]; MS m/z (FAB−) 647.3 [12, (M+2NBA)$^-$], 493.2 [34, (M−H+NBA)$^-$], 340.1 [100, (M−H)$^-$]; Acc MS m/z (FAB+) 342.17046, C$_{20}$H$_{24}$NO$_4$ requires 342.17053.

2-Methoxy-3-benzyloxy-marrianolic acid (52)

This was prepared in a similar manner to that of benzyl marrianolic acid 9. A solution of iodine (2.81 g, 11.07 mmol) in 35 mL of MeOH and a solution of KOH (5.05 g) in 10 mL of water and 22 mL of MeOH were added dropwise and alternatively to a stirred solution of 2-Methoxy-3-benzyloxy-estrone (51) (1.52 g, 3.89 mmol) in MeOH (700 mL). The resulting crude orange foam (1.80 g) was then dissolved in a solution of KOH (2.8 g) in MeOH/H$_2$O (1:2, 84 mL) and heated to reflux for 4 hours. The orange residue (4.32 g) that obtained was fractionated by flash chromatography with chloroform/methanol (95:5) as eluent and gave 52 as an orange residue (311 mg, 18%): $\delta_H$ (CDCl$_3$, 400 MHz) 1.02 (3H, s, C-18-H$_3$), 1.21-2.38 (11H, m), 2.64-2.70 (2H, m, C-6-H$_2$), 3.72 (3H, s, OCH$_3$), 5.01 (2H, s, OCH$_2$Ar), 6.70 (1H, s, C-4-H), 6.85 (1H, s, C-1-H), 7.30-7.45 (5H, m, C$_6$H$_5$) and 12.20 (2H, br. s, exchanged with D$_2$O, CO$_2$H); MS m/z (FAB+) 495.2 [10, (M+H+NBA)$^+$], 342.1 [100, (M+H)$^+$], 299.1 [40, (M+H-Ac)+]; MS m/z (FAB−) 647.3 [12, (M+2NBA)$^-$], 493.2 [34, (M−H+NBA)$^-$], 340.1 [100, (M−H)$^-$]; Ace MS m/z (FAB+) 342.17046, C$_{20}$H$_{24}$NO$_4$ requires 342.17053.

2-Methoxy-3-Benzyloxy-16,17-seco-estra-1,3,5(10)-triene-16,17-imide (53)

This was prepared in a similar manner to that of 10 by reaction of 2-Methoxy-3-benzyloxy-marrianolic acid (52) (300 mg, 684 mmol) with urea (300 mg, 4.99 mmol) at 180° C. Fractionation of the crude product that obtained by flash chromatography with chloroform/acetone (95:5) as eluent gave 53 as a light yellow powder (170 mg, 59%): mp 84-87° C.; $\delta_H$ (DMSO-d$_6$, 400 MHz) 1.10 (3H, s, C-18-H$_3$), 1.14-2.66 (11H, m), 2.67-2.72 (2H, m, C-6-H$_2$), 3.73 (3H, s, OCH$_3$), 5.02 (2H, s, OCH$_2$Ar), 6.73 (1H, s, C-4-H), 6.86 (1H, s, C-1-H), 7.30-7.46 (5H, m, C$_6$H$_5$) and 10.64 (1H, s, exchanged with D$_2$O, NH); MS m/z (FAB+) 495.2 [10, (M+H+NBA)$_j$], 342.1 [100, (M+H)], 299.1 [40, (M+H-Ac)$_j$]; MS m/z (FAB−) 647.3 [12, (M+2NBA)$^-$], 493.2 [34, (M−H+NBA)$^-$], 340.1 [100, (M−H)$^-$]; Acc MS m/z (FAB+) 342.17046, C$_{20}$H$_{24}$NO$_4$ requires 342.17053.

2-Methoxy-3-hydroxy-16,17-seco-estra-1,3,5(10)-triene-16,17-imide (54) (STX 325)

Following the hydrogenation conditions (see VI-1-4), a suspension of 53 (150 mg, 357 µmol) and Pd—C (10%, 80 mg) in MeOH/THF 2:1 (15 mL) was hydrogenated for 4 hours to give 54 as a light yellow powder (I 15 mg, 97%). An analytical sample was recrystallized from methanol to give white crystals: mp 202-205° C.; $\delta_H$ (DMSO-d$_6$, 400 MHz) 1.10 (3H, s, C-18-H$_3$), 1.13-2.42 (11H, m), 2.63-2.69 (2H, m, C-6-H$_2$), 3.71 (3H, s, OCH$_3$), 6.45 (1H, s, C-4-H), 6.78 (1H, s, C-1-H), 8.67 (1H, s, exchanged with D$_2$O, OH) and 10.63 (1H, s, exchanged with D$_2$O, NH); MS 711/z (FAB+) 495.2 [10, (M+H+NBA)+], 342.1 [100, (M+H)$^+$], 299.1 [40, (M+H-Ac)+]; MS m/z (FAB−) 647.3 [12, (M+2NBA)-], 493.2 [34, (M−H+NBA)$^-$], 340.1 [100, (M−H)$^-$]; Acc MS m/z (FAB+) 342.17046, C$_{20}$H$_{24}$NO$_4$ requires 342. 7053.

2-Methoxy-3-Sulfamoyl-16,17-seco-estra-1,3,5(10)-triene-16,17-imide (55) (STX 326)

Sodium hydride (60% dispersion in mineral oil, 8 mg, 200 µmol) was added to a stirred solution of 54 (55 mg, 167 µmol)

in anhydrous DMF (1 mL) at 0° C. under an atmosphere of N$_2$. After evolution of hydrogen had ceased, sulfamoyl chloride (6 eq) was added. The reaction mixture was then stirred under N$_2$ overnight in which time it was allowed to warm to room temperature. The mixture was poured into brine (20 mL), and the resulting solution was extracted with ethyl acetate (2×20 mL). The organic layer was separated, washed with brine (4×20 mL), dried (MgSO$_4$), filtered and concentrated under reduced pressure. Fractionation of the crude product that obtained by flash chromatography with chloroform/acetone (8:2) as eluent gave 55 as a white foam (30 mg, 48%). This was recrystallized from acetone/hexane 1:2 to give white crystals (23 mg, 37%): mp 225-230° C.; $\delta_H$ (DMSO-d$_6$, 400 MHz) 1.11 (3H, s, C-18-H$_3$), 1.21-2.47 (11H, m), 2.71-2.75 (2H, m, C-6-H$_2$), 3.77 (3H, s, OCH$_3$), 7.00 (1H, s, C-4-H or C-1-H), 7.02 (1H, s, C-1-H or C-4-H), 7.84 (2H, s, exchanged with D$_2$O, NH$_2$) and 10.65 (1H, s, exchanged with D$_2$O, NH); MS m/z (FAB+) 495.2 [10, (M+H+NBA)$^+$], 342.1 [100, (M+H)$^+$], 299.1 [40, (M+H-Ac)$^+$]; MS m/z (FAB−) 647.3 [12, (M+2NBA)$^-$], 493.2 [34, (M−H+NBA)$^-$], 340.1 [100, (M−H)$^-$]; Acc MS m/z (FAB+) 342.17046, C$_{20}$H$_{24}$NO$_4$ requires 342.17053.

All publications and patents and patent applications mentioned in the above specification are herein incorporated by reference.

Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biology or related fields are intended to be within the scope of the following claims.

ABBREVIATIONS

Å Angstrom
Ac Acetyl
Acc MS accurate mass spectrometry
Adiol androstenediol
Adione androstenedione
AG aminogluthethimide
aq aqueous
Ar aryl
arom aromatic
BMA 3-benzyl-marrianolic acid
Bn benzyl
br broad
° C. degrees Celsius
$^{13}$C NMR carbon NMR
ca approximately
cm centimeters
COUMATE 4-methylcoumarin-7-O-sulfamate
δ chemical shift in ppm
d doublet
dd doublet of doublets
DHEA dehydroepiandrosterone
DMF N,N-dimethylformamide
DMSO dimethylsulfoxide
E 1 oestrone
E2 oestradiol
EMATE estrone-3-O-sulfamate
ER estrogen receptor
eq equivalent
FAB fast atom bombardment
g gram(s)
h hour(s)
hER human estrogen receptor
1H NMR proton NMR
HPLC high pressure liquid chromatography
17β-HSD 17β-hydroxysteoid dehydrogenase
Hz Hertz
IC$_{50}$ concentration causing 50% inhibition
IR infrared
J coupling constant in Hz
$\lambda_{max}$ wavelength of maximum absorption
lit. literature reference
μ micro
m multiplet
M mol per liter
m-NBA meta-nitrobenzyl alcohol
m-RNA messenger ribonucleic acid
MHz megahertz
min minute
mmol millimole
mol mole
mp melting point
MS mass spectrometry
m/z mass to charge ratio
NADPH nicotinamide adenine dinucteotide phosphate
nM nanomole
NMR nuclear magnetic resonance
ppm parts per million
R$_f$ retention factor
r.t. room temperature
S. D. standard deviation Pd—C palladium-charcoal
TBAF tetrabutylammonium fluoride
   TBDMS tert-butyl-dimethylsityl
THF tetrahydrofuran
TLC thin layer chromatography
TMS tetramethylsilane
v frequency of a signal in Hz
vs versus

REFERENCES (1) Saunders, C. M.; Baum, M. Management of early breast cancer. *Oncol. in Pract.* 1994, 3, 4-8

(2) Nicholls P. J. Breast cancer management: science and care together. *Pharm. J.* 1997, 259, 459-470

(3) Miller, B. A.; Kolonel, L. N.; Bernstein, L.; Young, Jr. J. L.; Swanson, G. M.; West, D.; Key, C. R.; Liff, J. M.; Glover, C. S.; Alexander, G. A.; et al. (eds). Racial/Ethnic patterns of cancer in the united states 1988-1992. *National Cancer Institute* 1996

(4) (a) Kaae, S, and Johansen, H. Does simple mastectomy followed by irradiation offer the survival comparable to radical procedures? *International Journal of Radiation Oncology, Biology, Physics.* 1977, 2, 1163-1166 (b) Holli, K.; Saaristo, R.; Isola, J.; Joensuu, H. and Hakama, M. Lumpectomy with or without postoperative radiotherapy for breast cancer with favourable prognostic features: results of a randomised study. *Br. J. Cancer* 2001, 84(2), 164-169

(5) Early Breast Cancer Trialists Collaborative Group. Effects of adjuvant Tamoxifen and of cytotoxic therapy on mortality in early breast cancer. *N. Eng. J. Med.* 1988, 319, 1681-1692

(6) Gorski, J.; Toft, D.; Shyamala, G.; Smith, D.; Notides, A. Hormones receptors: studies on the interaction of estrogens with the uterus. *Recent Prog. Horm. Res.* 1968, 24, 45-80

(7) Gorski, J. and Gannon F. Current models of steroid hormone action: a critique. *Ann. Rev. Physiol.* 1976, 38, 425-450
(8) Coulson, C. J. Steroid biosynthesis and action, 2$^{nd}$ edition. *Molecular Mechanism of Drug Action.* 1994, 95-122
(9) (a) Horwitz, K. B. and McGuire, W. L. Nuclear mechanism of estrogen action: effects of oestradiol and antiestrogens on estrogens receptors and nuclear receptor processing. *J. Biol. Chem.* 1978, 253, 8185-8191 (b) Horwitz, K. B.; Koseki, Y. and McGuire, W. L. Oestrogen control of progesterone receptor in human breat cancer: role of oestradiol and antiestrogen. *Endocrinology* 1978, 103, 1742-1751
(10) (a) Jordan, V. C. The strategic use of antiestrogens to control the development and growth of breast cancer. *Cancer.* 1992, 70, 977-982 (b) Powles, T. J. Breast cancer prevention *Breast Cancer Res.* 2000, 2, 10-12
(11) Wakeling, A. E.; Bowler, J. Steroidal pure antiestrogens. *J. Endocrinol.* 1987, 112, R7-R10
(12) Sexton, M. J.; Gherman, R. B. Selective estrogen receptor modulators: the ideal estrogen replacement? *Prim. Care. Update Ob/Gyns* 2001, 8(1), 25-30
(13) Agnusdei, D.; Liu-Leage, S.; Augendre-Ferrante, B. *Ann. Endocrinol.* 1999, 60(3), 242-246
(14) John Smith, H.; Nicholls, P. J.; Simons, C.; Le Lain, R. Inhibitors of steroidogenesis as agents for the treatment of hormone-dependent breast cancer. *Exp. Opin. Ther. Patents* 2001, 11, 789-824
(15) (a) Castiglione-Gertsch, M. New aromatase inhibitors: more selectivity, less toxicity, unfortunately, the same activity. *Eur. J. Cancer* 1996, 32A, 393-395 (b) Miller, W. R. Aromatase inhibitors—where are we now? *Br. J. Cancer* 1996, 73, 415-417
(16) Santner, S. J.; Feil, P. D and Santen, R. J. In situ estrogen production via the oestrone sulphatase pathway in breast tumour: relative importance vs the aromatase pathway. *J. Clin. Endocrin. Metab.* 1984, 59, 29-33
(17) Purohit, A. Williams, G. J.; Howarth, N. M.; Potter, B. V. L. and Reed, M. J. Inactivation of steroid sulphatase by an active site-directed inhibitor, estrone-3-O-sulfamate. *Biochem.* 1995, 34, 11508-11514
(18) Purohit, A.; Williams, G. J.; Roberts, C. J.; Potter, B. V. L.; Reed, M. J. In vivo inhibition of oestrone sulphatase and dehydroepiandrosterone sulphatase by estrone-3-O-sulfamate. *Int. J. Cancer* 1995, 62, 106-111
(19) Woo, L. W. L.; Howarth, N. M.; Purohit, A.; Hejaz, H. A. M.; Reed, M. J. and Potter, B. V. L. Steroidal and nonsteroidal sulfamates as potent inhibitors of steroid sulphatase. *J. Med. Chem.* 1998, 41, 1068-1083
(20) Purohit, A.; Woo, L. W. L.; Singh, A.; Winterborn, C. J.; Potter, B. V. L. and Reed, M. J. In vivo activity of 4-methylcoumarin-7-O-sulfamate, a non steroidal, non estrogenic steroid sulphatase inhibitor. *Cancer Res.* 1996, 56, 4950-4955
(21) (a) Woo, L. W. L.; Purohit, A.; Malini, B.; Reed, M. J. and Potter, B. V. L. Potent active site-directed inhibition of steroid sulphatase by tricyclic coumarin-based sulfamates. *Chemistry & Biology* 2000, 7, 773-791 (b) Malini, B.; Purohit, A.; Ganeshapillai, D.; Woo, L. W. L.; Potter, B. V. L.; Reed, M. J. Inhibition of steroid sulphatase activity by tricyclic coumarin sulfamates. *J. Steroid Biochem. Molec. Biol.* 2000, 75, 253-25 (c) Purohit, A.; Woo, L. W. L.; Barrow, D.; Hejaz, H. A. M.; Nicholson, R. I.; Potter, B. V. L.; Reed, M. J. Non-steroidal and steroidal sulfamates: new drugs for cancer therapy. *Mol. Cell. Endocrinol.* 2001, 171, 129-135
(22) Purohit, A.; Woo, L. W. L.; Potter, B. V. L.; Reed, M. J. In vivo inhibition of oestrone sulphatase activity and growth of nitrosomethylurea-induced mammary tumours by 667 COUMATE. *Cancer Res.* 2000, 60, 3394-3396
(23) Claussner, A.; Nédelec, L.; Nique, F.; Philibert, D.; Teush, G.; Van de Velde, P. 110-Amidoalkylestradiols as new series of pure anti-estrogens. *J. Steroid. Biochem.* 1992, 41, 609-614
(24) Li, P-K.; Chu, G-C.; Guo, J. P.; Selcer, K. W. Development of potent non-estrogenic oestrone sulphatase inhibitors. *Steroids* 1998, 63, 425-432
(25) (a) Jin, J-Z.; Lin, S-X. Human estrogenic 17β-hydroxysteroid dehydrogenase: predominance of oestrone reduction and its induction by NADPH. *Biochem. Biophys. Res.* 1999, 259, 489-493 (b) Penning, T. M. Molecular endocrinology of hydroxysteroid dehydrogenases. *Endocrine Reviews* 1997, 18, 281-305
(26) (a) Labrie, F. At the cutting edge. Intracrinology. *Mol. Cell. Endocrinol.* 1991, 78, C113-C118 (b) Poulin, R.; Labrie, F. Stimulation of cell proliferation and estrogenic response by adrenal $C_{19}$-?$^5$-steroids in the ZR-75-1 Human Breast Cancer Cell Line. *Cancer Res.* 1986, 46, 4933-4937
(27) (a) Peltoketo, H.; Luu-The, V.; Simard, J.; Adamski, J. 17β-hydroxysteroid dehydrogenase (HSD)/17-ketosteroid reductase (KSR) family; nomenclature and main characteristics of the 17 HSD/KSR enzymes. *J. Mol. Endocrinol.* 1999, 23, 1-11 (b) Peltoketo, H.; Isomaa, V.; Maentausta, O.; Vihko, R. Complete amino acid sequence of human placental 17β-hydroxysteroid dehydrogenase deduced from cDNA. *FEBS Lett.* 1988, 239, 73-77 (c) Wu, L.; Einstein, M.; Geissler, W. M.; Chan, H. K.; Elliston, K. O.; Andersson, S. Expression cloning and characterization of human 17β-hydroxysteroid dehydrogenase type 2, a microsomal enzyme possessing 20α-hydroxysteroid dehydrogenase activity. *J. Biol. Chem.* 1993, 268, 12964-12969 (d) Geissler, W. M.; Davis, D. L.; Wu, L.; Bradshaw, K. D.; Patel, S.; Mendonca, B. B.; Elliston, K. O.; Wilston, J. D.; Russell, D. W.; Andersson, S. Male pseudohermaphroditism caused by mutation of testicular 17β-hydroxysteroid dehydrogenase 3. *Nat. Genet.* 1994, 7, 34-39 (e) Adamski, J.; Normand, T.; Leenders F.; Monte, D.; Begue, A.; Stehelin, D.; Jungblut, P. W.; de Launoit, Y. Molecular cloning of a novel widely expressed human 80 kDa 17β-hydroxysteroid dehydrogenase IV. *Biochem. J.* 1995, 311, 437-443 (f) Deyashiki, Y.; Ohshima, K.; Nakanishi, M.; Sato, K.; Matsuura, K.; Hara, A. Molecular cloning and characterization of mouse oestradiol 17β-dehydrogenase (A-specific), a member of the aldoketoreductase family. *J. Biol. Chem.* 1995, 270, 10461-10467
(28) Tremblay, M. R.; Auger, S, and Poirier, D. Synthesis of 16-(bromoalkyl)-estradiols having inhibitory effect on human placental oestradiol 17β-hydroxysteroid dehydrogenase (17β-HSD type 1). *Bioorg. Med. Chem.* 1995, 3, 505-523
(29) Tremblay, M. R.; Poirier, D. Overview of a rational approach to design type 117β-hydroxysteroid dehydrogenase inhibitors without estrogenic activity: chemical synthesis and biological evaluation. *J. Steroid. Biochem.* 1998, 66, 179-191
(30) Collins, B. M.; Mac Lachlan, J. A.; Arnold, S. F. The estrogenic and anti-oestrogenic activities of phytochemicals with the human estrogen receptor expressed in yeast. *Steroids* 1997, 62, 365-372
(31) (a) Makela, S.; Poutanen, M.; Kostian, M. L.; Lehtimaki, N.; Strauss, L.; Santti, R.; Vihko, R. Inhibition of 17 beta-

(32) LeBail, J. C.; Laroche, T.; Marre-Fournier, F.; Habrioux, G. Aromatase and 17β-hydroxysteroid dehydrogenase inhibition by flavonoids. *Cancer Lett.* 1998, 133, 101-106

(33) Coldham, N. G.; James, V. H. T. A possible mechanism for increased breast cell proliferation by progestins through increased reductive 17β-hydroxysteroid dehydrogenase activity. *Int. J. Cancer* 1990, 45, 174-178

(34) Purohit, A.; Hejaz, H. A. M.; Walden, J.; MacCarthy-Marrogh, L.; Packam, G.; Potter, B. V. L.; Reed, M. J. The effect of 2-methoxyestrone-3-O-sulphamate on the growth of breast cancer cells and induced mammary tumours. *Int. J. Cancer* 2000, 85,

(35) Heer, J.; Miescher, K. Ober Steroide. Marrianol-und Doisynolsäure. Über oestrogene carbonsäjuren II. *Helv. Chim. Acta* 1945, 28, 156-165

(36) (a) Matkovics, B.; Taródi, B.; Baláspiri, L. Rearrangement of steroids, VII. Schmidt reaction and Beckmann rearrangement of oestrone and its derivatives. *Acta Chim. Acad. Scien. Hung.* 1974, 80, 79-87 (b) Regan, B. M.; Newton Hayes, F. 17- and 17-Aza-D-homosteroids. *J. Am. Chem. Soc.* 1956, 78, 639-643

(37) Gupta, R. and Jindal, D. P. Synthesis and biological activity of some D-ring modified oestrone derivatives. *Ind. J. Chem.* 1999, 38B, 563-571

(38) Love, B. and Dawson, C. R. Alkylphenols related to the poison ivy principle. An improved method of synthesis involving the Na-Butanol cleavage of benzyl ethers. *J. Am. Chem. Soc.* 1956, 78, 6095-6101

(39) Okada, M.; Iwashita, S.; Koizumi, N. Efficient general method for sulfamoylation of a hydroxyl group. *Tet. Lett.* 2000, 41, 7047-7051.

(40) C. A. Hioruchi & J. Y. Satoh, Regioselective 2-Iodination of Estradiol, Estriol & Oestrone, J. Chem. Soc., Chem. Commun., 1982, 671-672.

(41) M. Numazawa and Y. Ogura, J. Chem. Soc., Chem. Commun. 1983, 9, 533.

(42) Williams, G. J.; Woo, L. W. L.; Mahon, M. F.; Purohit, A.; Reed, M. J.; Potter, B. V. L. X-ray crystal structure and mechanism of action of oestrone 3-O-sulphamate, a synthetic active site-directed inhibitor of oestrone sulphatase. *Pharm. Sci.* 1996, 2, 11-16

(43) Ghosh, D.; Pletnev, V. Z.; Zhu, D-W. et al. Structure of the human estrogenic 17 beta-hydroxysteroid dehydrogenase at 2.20 Å resolution. *Structure*, 1995, 3, 503-513

(44) (a) Lin, S. X.; Han, Q.; Azzi, A.; Zhu, D-W.; Gongloff, A.; Campbell, R. L. 3D structure of human estrogenic 17β-HSD: binding with various steroids. *J. Steroid Biochem. Mol. Biol.* 1999, 69, 425-429 (b) Puranen, T.; Poutanen, M.; Ghosh, D.; Vihko, R. and Vihko, P. Origin of substrate specificity of human and rat 17β-hydroxysteroid dehydrogenase Type 1, using chimeric enzymes and site-directed substitutions. *Endocrinology* 1997, 138, 3532-3539

(45) Breton, R.; Housset, D.; Mazza, C.; Fontecilla-Camps, J. C. The structure of a complex of human 17β-hydroxysteroid dehydrogenase with oestradiol and NADP+ identifies two principal targets for the design of inhibitors. *Structure (Lond)* 1996, 4, 905-915

(46) Apel, R.; Berger, G. Über das hydrazidosulfamid *Chem. Ber.* 1958, 91, 1339-1341

(47) Woo, L. W. W.; Lightowler, M.; Purohit, A.; Reed, M. J.; Potter, B. V. L. Heteroatom-substituted analogues of the active-site directed inhibitor estra-1,3,5(10)-trien-17-one-3-sulphamate inhibit oestrone sulphatase by different mechanism. *J. Steroid Biochem Mol. Biol.* 1996, 57, 79-88

(48) Duncan, L.; Purohit, A.; Howarth, N. M.; Potter, B. V. L.; Reed, M. J. Inhibition of oestrone sulphatase activity by estrone-3-methyl-thiophosphonate: a potential therapeutic agent in breast cancer *Cancer Res.* 1993, 53, 298-303

The invention claimed is:

1. A compound having a formula

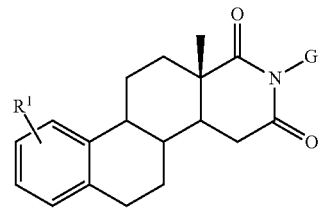

where $R^1$ is a sulphamate group
wherein G is H, OH or a hydrocarbyl group
wherein the compound is optionally substituted at at least position 2 by one or more substituents selected from hydroxyl, alkyl, alkoxy, alkynyl, and halogen.

2. A compound according to claim 1 having a formula

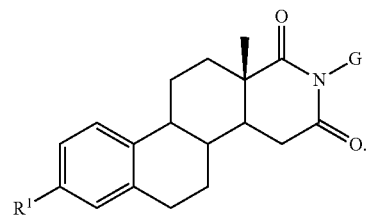

3. A compound according to claim 1 wherein the hydrocarbyl group is an optionally substituted hydrocarbon group.

4. A compound according to claim 1 wherein the hydrocarbyl group is an optionally substituted alkyl group.

5. A compound according to claim 1 wherein the hydrocarbyl group is $C_1$-$C_{10}$ alkyl group.

6. A compound according to claim 1 wherein the hydrocarbyl group is $C_1$-$C_{10}$ haloalkyl group.

7. A compound according to claim 1 wherein the hydrocarbyl group is selected from —$(CH_2)_{1-10}$ aryl and $(CH_2)_{1-10}$-Ph-$C_{1-10}$ alkyl.

8. A compound according to claim 1 wherein the hydrocarbyl group is selected from —$(CH_2)_{1-10}$ cycloalkyl and —$(CH_2)_{1-10}$—$C_{3-10}$cycloalkyl.

9. A compound according to claim 1 wherein the hydrocarbyl group is an alkene group.

10. A compound according to claim 1 wherein the hydrocarbyl group is $C_1$-$C_{10}$ alkene group.

11. A compound according to claim 1 wherein G is H.

12. A compound according to claim 1 wherein $R^1$ or the sulphamate group is of the formula

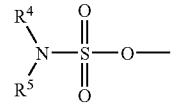

wherein R⁴ and R⁵ are independently selected from H, alkyl, cycloalkyl, alkenyl and aryl, or combinations thereof, or together represent alkylene.

13. A compound according to claim 12 wherein at least one of R⁴ and R⁵ is H.

14. A compound according to claim 13 wherein R⁴ and R⁵ are H.

15. A compound according to claim 1 having the formula

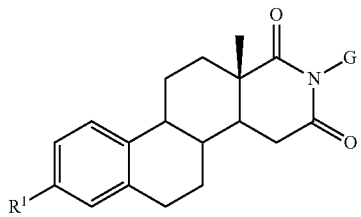

wherein G is selected from H, OH, $C_1$-$C_{10}$ alkyl, $C_1$-$C_{10}$ haloalkyl, —$(CH_2)_{1-10}$-aryl, —$(CH_2)_{1-10}$-cycloalkyl, and $C_1$-$C_{10}$ alkene;

wherein R¹ is a sulphamate group of the formula

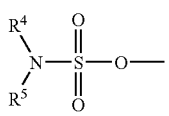

wherein R⁴ and R⁵ are independently selected from H, alkyl, cycloalkyl, alkenyl and aryl, or combinations thereof, or together represent alkylene.

16. A pharmaceutical composition comprising a compound according to claim 1 optionally admixed with a pharmaceutically acceptable carrier, diluent, excipient or adjuvant.

17. A method of inhibiting steroid sulphatase (STS) activity in breast cancer cells, endometrial cancer cells, or ovarian cancer cells, comprising administering the compound according to claim 1.

18. A compound according to claim 1 wherein the compound is optionally substituted by one or more substituents selected from more hydroxy, methyl, ethyl, n-propyl, isopropyl, n-butyl, sec-butyl, tert-butyl, n-pentyl, methoxy, ethoxy, propoxy, ethinyl and fluoro.

19. A compound according to claim 1 wherein the compound is of formula

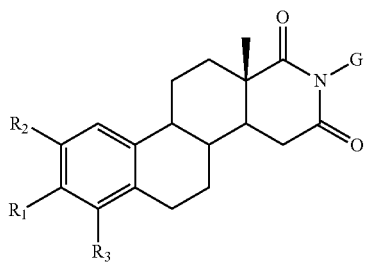

wherein $R_2$ and $R_3$ are independently selected from H, alkyl and alkoxy, wherein at least one of $R_2$ and $R_3$ is an alkyl or alkoxy group.

20. A compound according to claim 19 wherein $R_2$ is selected from alkyl and alkoxy and $R_3$ is H.

21. A compound according to claim 1 wherein the compound is

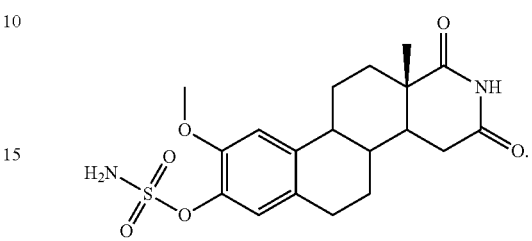

22. A compound according to claim 5 wherein the $C_1$-$C_{10}$ alkyl group is selected from $C_1$-$C_6$ alkyl group and $C_1$-$C_3$ alkyl group.

23. A compound according to claim 6 wherein the $C_1$-$C_{10}$ haloalkyl group is a $C_1$-$C_{10}$ bromoalkyl group.

24. A compound according to claim 6 wherein the $C_1$-$C_{10}$ haloalkyl group is selected from $C_1$-$C_6$ haloalkyl group and $C_1$-$C_3$ haloalkyl group.

25. A compound according to claim 23 wherein the $C_1$-$C_{10}$ bromoalkyl group is selected from $C_1$-$C_6$ bromoalkyl group and $C_1$-$C_3$ bromoalkyl group.

26. A compound according to claim 7 wherein —$(CH_2)_{1-10}$-aryl is $(CH_2)_{1-10}$-Ph.

27. A compound according to claim 26 wherein the —$(CH_2)_{1-10}$-Ph is selected from —$(CH_2)_{1-5}$-Ph, —$(CH_2)_{1-3}$-Ph, and —$CH_2$-Ph.

28. A compound according to claim 7 wherein the $(CH_2)_{1-10}$-Ph-$C_{1-10}$ alkyl is selected from $(CH_2)_{1-5}$-Ph-$C_{1-5}$ alkyl, $(CH_2)_{1-3}$ alkyl, and —$CH_2$-Ph-$C(CH_3)_3$.

29. A compound according to claim 8 wherein the $(CH_2)_{1-10}$—$C_{3-10}$cycloalkyl is selected from —$(CH_2)_{1-7}$—$C_{3-7}$cycloalkyl, —$(CH_2)_{1-5}$—$C_{3-5}$cycloalkyl, —$(CH_2)_{1-3}$—$C_{3-5}$cycloalkyl, and —$CH_2$—$C_3$cycloalkyl.

30. A compound according to claim 10 wherein $C_1$-$C_{10}$ alkene group is selected from $C_1$-$C_6$ alkene group and $C_1$-$C_3$ alkene group.

31. A compound according to claim 12 wherein the alkyl or cycloalkyl or alkenyl contain one or more hetero atoms or groups.

32. A compound according to claim 12 wherein each alkyl, cycloalkyl and alkenyl contain one or more hetero atoms or groups.

33. A compound according to claim 15 wherein the alkyl, cycloalkyl and alkenyl contain one or more hetero atoms or groups.

34. A compound according to claim 15 wherein each alkyl, cycloalkyl and alkenyl contain one or more hetero atoms or groups.

* * * * *